(12) United States Patent
Sano et al.

(10) Patent No.: US 10,537,379 B2
(45) Date of Patent: Jan. 21, 2020

(54) IRREVERSIBLE ELECTROPORATION USING TISSUE VASCULATURE TO TREAT ABERRANT CELL MASSES OR CREATE TISSUE SCAFFOLDS

(71) Applicant: Virginia Tech Intellectual Properties, Inc., Blacksburg, VA (US)

(72) Inventors: Michael B. Sano, Blacksburg, VA (US); Rafael V. Davalos, Blacksburg, VA (US); John L. Robertson, Floyd, VA (US); Paulo A. Garcia, Blacksburg, VA (US); Robert E. Neal, Richmond, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 15/843,888

(22) Filed: Dec. 15, 2017

(65) Prior Publication Data
US 2018/0125565 A1 May 10, 2018

Related U.S. Application Data

(60) Division of application No. 13/989,175, filed as application No. PCT/US2011/062067 on Nov. 23, (Continued)

(51) Int. Cl.
*A61B 18/14* (2006.01)
*A61K 48/00* (2006.01)
(Continued)

(52) U.S. Cl.
CPC .......... *A61B 18/14* (2013.01); *A61K 48/0075* (2013.01); *A61M 5/00* (2013.01);
(Continued)

(58) Field of Classification Search
CPC . A61B 18/12; A61B 18/1206; A61B 18/1266; A61B 18/14; A61B 18/1466;
(Continued)

(56) References Cited

U.S. PATENT DOCUMENTS

| 1,653,819 A | 12/1927 | Northcott |
| 3,730,238 A | 5/1973 | Butler |

(Continued)

FOREIGN PATENT DOCUMENTS

| AU | 2002315095 A1 | 12/2002 |
| AU | 2003227960 A1 | 12/2003 |

(Continued)

OTHER PUBLICATIONS

Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
(Continued)

*Primary Examiner* — Michael F Peffley
*Assistant Examiner* — Khadijeh A Vahdat
(74) *Attorney, Agent, or Firm* — New River Valley IP Law, PC; Michele L. Mayberry

(57) ABSTRACT

The present invention relates to the field of medical treatment of diseases and disorders, as well as the field of biomedical engineering. Embodiments of the invention relate to the delivery of Irreversible Electroporation (IRE) through the vasculature of organs to treat tumors embedded deep within the tissue or organ, or to decellularize organs to produce a scaffold from existing animal tissue with the existing vasculature intact. In particular, methods of administering non-thermal irreversible electroporation (IRE) in vivo are provided for the treatment of tumors located in vascularized tissues and organs. Embodiments of the inven-
(Continued)

tion further provide scaffolds and tissues from natural sources created using IRE ex vivo to remove cellular debris, maximize recellularization potential, and minimize foreign body immune response. The engineered tissues can be used in methods of treating subjects, such as those in need of tissue replacement or augmentation.

14 Claims, 19 Drawing Sheets

Related U.S. Application Data 2011, now Pat. No. 9,867,652, which is a continuation-in-part of application No. 12/491,151, filed on Jun. 24, 2009, now Pat. No. 8,992,517, and a continuation-in-part of application No. 12/432,295, filed on Apr. 29, 2009, now Pat. No. 9,598,691.

(60) Provisional application No. 61/171,564, filed on Apr. 22, 2009, provisional application No. 61/167,997, filed on Apr. 9, 2009, provisional application No. 61/075,216, filed on Jun. 24, 2008, provisional application No. 61/125,840, filed on Apr. 29, 2008, provisional application No. 61/416,534, filed on Nov. 23, 2010.

(51) Int. Cl.
*A61M 5/00* (2006.01)
*A61N 1/32* (2006.01)
*A61B 18/00* (2006.01)

(52) U.S. Cl.
CPC . *A61B 18/1492* (2013.01); *A61B 2018/00613* (2013.01); *A61B 2018/1472* (2013.01); *A61B 2218/002* (2013.01); *A61N 1/327* (2013.01)

(58) Field of Classification Search
CPC ...... A61B 18/1492; A61B 2018/00613; A61B 2018/1472; A61B 2218/002; A61K 48/0075; A61M 5/00; A61N 1/327; H05K 999/99
USPC ................................................. 606/28–50
See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |

(56) References Cited

U.S. PATENT DOCUMENTS

| | | |
|---|---|---|
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll et al. |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |

(56) References Cited

U.S. PATENT DOCUMENTS

| | | |
|---|---|---|
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 * | 9/2005 | Johnson ............... A61F 2/958 606/194 |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |

(56) References Cited

U.S. PATENT DOCUMENTS

| | | |
|---|---|---|
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,484 B2 | 6/2013 | Davalos et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,867,652 B2 | 1/2018 | Sane et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Arena et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |

(56) References Cited

U.S. PATENT DOCUMENTS

| | | |
|---|---|---|
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1* | 10/2006 | Demarais ............... A61N 1/327 607/2 |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1 | 6/2007 | Demarais et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326436 A1 | 12/2009 | Rubinsky et al. |
| 2009/0326570 A1 | 12/2009 | Brown |
| 2010/0004623 A1* | 1/2010 | Hamilton, Jr. ...... A61B 18/1492 604/501 |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |

(56) References Cited

U.S. PATENT DOCUMENTS

| | | |
|---|---|---|
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0106221 A1 | 5/2011 | Robert et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320488 A1 | 11/2015 | Moshe et al. |
| 2015/0327944 A1 | 11/2015 | Robert et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338761 A1 | 11/2016 | Chornenky et al. |
| 2016/0354142 A1 | 12/2016 | Pearson et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0360326 A1 | 12/2017 | Davalos |
| 2018/0125565 A1 | 5/2018 | Sane et al. |
| 2018/0161086 A1 | 6/2018 | Davalos et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0133671 A1 | 5/2019 | Davalos et al. |
| 2019/0175248 A1 | 6/2019 | Neal, II |
| 2019/0175260 A1 | 6/2019 | Davalos |

FOREIGN PATENT DOCUMENTS

| | | |
|---|---|---|
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| DE | 863111 | 1/1953 |
| DE | 4000893 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2381829 A1 | 11/2011 |
| EP | 2413833 A1 | 2/2012 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |

(56) References Cited

FOREIGN PATENT DOCUMENTS

| | | |
|---|---|---|
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 A | 7/2011 |
| JP | 2012510332 A | 5/2012 |
| JP | 2012515018 A | 7/2012 |
| JP | 2012521863 A | 9/2012 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |

OTHER PUBLICATIONS

Salmanzadeh et al., "Sphingolipid Metabolites Modulate Dielectric Characteristics of Cells in a Mouse Ovarian Cancer Progression Model." Integr. Biol., 5(6), pp. 843-852 (2013).

Sano et al., "Contactless Dielectrophoretic Spectroscopy: Examination of the Dielectric Properties of Cells Found in Blood." Electrophoresis, 32, pp. 3164-3171, 2011.

Sano et al., "In-vitro bipolar nano- and microsecond electro-pulse bursts for irreversible electroporation therapies." Bioelectrochemistry vol. 100, pp. 69-79 (2014).

Sano et al., "Modeling and Development of a Low Frequency Contactless Dielectrophoresis (cDEP) Plafform to Sort Cancer Cells from Dilute Whole Blood Samples." Biosensors & Bioelectronics, 8 pages (2011).

Sang, M. B., et al., "Towards the creation of decellularized organ constructs using irreversible electroporation and active mechanical perfusion", Biomedical Engineering Online, Biomed Central Ltd, London, GB, vol. 9, No. 1, Dec. 10, 2010, p. 83.

Saur et al., "CXCR4 expression increases liver and lung metastasis in a mouse model of pancreatic cancer." Gastroenterology, vol. 129, pp. 1237-1250 (2005).

Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.

Schoenbach et al., "Intracellular effect of ultrashort electrical pulses." Bioelectromagnetics, 22 (2001) pp. 440-448.

Seibert et al., "Clonal variation of MCF-7 breast cancer cells in vitro and in athymic nude mice." Cancer Research, vol. 43, pp. 2223-2239 (1983).

Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).

Sel, D. et al. Sequential finite element model of tissue electropermeabilization. IEEE Transactions on Biomedical Engineering 52, 816-827, doi:10.1109/tbme.2005.845212 (2005).

Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).

Sersa, et al., Reduced Blood Flow and Oxygenation in SA-1 Tumours after Electrochemotherapy with Cisplatin, British Journal of Cancer, 87, 1047-1054, 2002.

Sersa, et al., Tumour Blood Flow Modifying Effects of Electrochemotherapy: a Potential Vascular Targeted Mechanism, Radiol. Oncol., 37(1): 43-8, 2003.

Sharma, A., et al., "Review on Thermal Energy Storage with Phase Change Materials and Applications", Renewable Sustainable Energy Rev. 13(2), 318-345 (2009).

Sharma, et al., Poloxamer 188 Decreases Susceptibility of Artificial Lipid Membranes to Electroporation, Biophysical Journal, vol. 71, No. 6, pp. 3229-3241, Dec. 1996.

Shiina, S., et al, Percutaneous ethanol injection therapy for hepatocellular carcinoma: results in 146 patients. AJR, 1993, 160: p. 1023-8.

Szot et al., "3D in vitro bioengineered tumors based on collagen I hydrogels." Biomaterials vol. 32, pp. 7905-7912 (2011).

Talele, S., et al., "Modelling single cell electroporation with bipolar pulse parameters and dynamic pore radii". Journal of Electrostatics, 68(3): p. 261-274 (2010).

Tekle, Ephrem, R. Dean Astumian, and P. Boon Chock, Electroporation by using bipolar oscillating electric field: An Improved method

(56) References Cited

OTHER PUBLICATIONS for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson, K. R., et al., "Investigation of the Safety of Irreversible Electroporation in Humans" J. Vascular Int. Radiol. 22 (5), 611-621 (2011).
TUNA—Suggested Local Anesthesia Guidelines, no date available.
Verbridge et al., "Oxygen-Controlled Three-Dimensional Cultures to Analyze Tumor Angiogenesis." Tissue Engineering, Part A vol. 16, pp. 2133-2141 (2010).
Vernier, P.T., et al., "Nanoelectropulse-driven membrane perturbation and small molecule permeabilization", Bmc Cell Biology, 7 (2006).
Vidamed, Inc., Transurethral Needle Ablation (TUNA): Highlights from Worldwide Clinical Studies, Vidamed's Office TUNA System, 2001.
Weaver et al., "A brief overview of electroporation pulse strength-duration space: A region where additional Intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Co-Pending U.S. Appl. No. 14/017,210, Response to Dec. 15, 2016 Non-Final Office Action dated Mar. 20, 2017, 9 pages.
Co-Pending U.S. Appl. No. 14/017,210, Response to May 1, 2017 Final Office Action dated Aug. 1, 2017, 10 pages.
Co-Pending U.S. Appl. No. 14/017,210, Response to Oct. 25, 2017 Non-Final Office Action dated Jan. 25, 2018, 11 pages.
Co-Pending U.S. Appl. No. 14/017,210, Response to Sep. 8, 2015 Non-Final Office Actioni, dated Mar. 8, 2016, 57 pages.
Co-Pending U.S. Appl. No. 14/017,210, filed Sep. 3, 2013.
Co-Pending U.S. Appl. No. 14/017,210, Non-Final Office Action dated Sep. 8, 2015, 8 pages.
Co-Pending U.S. Appl. No. 14/627,046, Amendment dated Jun. 29, 2017, 8 pages.
Co-Pending U.S. Appl. No. 14/627,046, filed Feb. 20, 2015.
Co-Pending U.S. Appl. No. 14/627,046, Final Office Action dated Sep. 14, 2017, 11 pages.
Co-Pending U.S. Appl. No. US 14/627,046, Interview Summary dated dated Apr. 27, 2018, 3 pages.
Co-Pending U.S. Appl. No. 14/627,046, Non-Final Office Action dated Feb. 15, 2018, 12 pages.
Co-Pending U.S. Appl. No. 14/627,046, Non-Final Office Action dated Mar. 29, 2017, 9 pages.
Co-Pending U.S. Appl. No. 14/627,046, Notice of Allowance dated Sep. 19, 2018, 7 pages.
Co-Pending U.S. Appl. No. 14/627,046, Response to Mar. 29, 2017 Non-Final Office Action, dated Jun. 29, 2017, 8 pages.
Co-Pending U.S. Appl. No. 14/627,046, Response to Sep. 14, 2017 Final Office Action dated Dec. 14, 2017, 7 pages.
Co-Pending U.S. Appl. No. 14/627,046, Rule 132 Affidavit and Response to Feb. 15, 2018 Non-Final Office Action, dated Jun. 15, 2018, 13 pages.
Co-Pending U.S. Appl. No. 14/686,380, filed Apr. 14, 2015.
Co-Pending U.S. Appl. No. 14/940,863, filed Nov. 13, 2015 and Published as US 2016/0066977 on Mar. 10, 2016.
Co-Pending U.S. Appl. No. 15/011,752, filed Feb. 1, 2016.
Co-pending U.S. Appl. No. 16/152,743, filed Oct. 5, 2018.
Co-pending European Application No. 10 824 248.8, Invitation Pursuant to rule 62a(1) EPC (Sep. 25, 2013).
Corovic, S., et al., "Analytical and numerical quantification and comparison of the local electric field in the tissue for different electrode configurations," Biomed Eng Online, 6, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, et al ., Theoretical Analysis of the Thermal Effects During In Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, R.V., et al., "Electrical impedance tomography for imaging tissue electroporation," IEEE Transactions on Biomedical Engineering, 51, 761-767, 2004.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
De Vuyst, E, et al., "In situ bipolar Electroporation for localized cell loading with reporter dyes and investigating gap functional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.

(56) References Cited

OTHER PUBLICATIONS

Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd, J., et al. In-Vivo Results of a New Focal Tissue Ablation Technique: Irreversible Electroporaton, IEEE Trans. Biomed. Eng. 53 (2006) p. 1409-1415.
Edd, J.F, et al., 2007, "Mathematical modeling of irreversible electroporation for treatment planning.", Technology in Cancer Research and Treatment., 6:275-286.
Elis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields". Technology in Cancer Research & Treatment, 8(4): p. 289-306 (2009).
Extended European Search Report. May 11, 2012. PCT/US2009042100 from EP 09739678.2.
A.I. Daud et al., "Phase I Trial of Interleukin-12 Plasmid Electroporation in Patients With Metastatic Melanoma," Journal of Clinical Oncology, 26, pp. 5896-5903, 2008.
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Al-Sakere, B. et al., 2007, "Tumor ablation with irreversible electroporation." PLoS ONE 2.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L, et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)-Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Ben-David, E.,et al., "Characterization of Irreversible Electroporation Ablation in In Vivo Procine Liver" Am. J. Roentgenol. 198(1), W62-W68 (2012).
Blad, et al., Impedance Spectra of Tumour Tissue in Comparison with Normal Tissue; a Possible Clinical Application for Electrical or Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Boone, K., Barber, D. & Brown, B. Review—Imaging with electricity: report of the European Concerted Action on Impedance Tomography. J. Med. Eng. Technol. 21, 201-232 (1997).
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.

(56) References Cited

OTHER PUBLICATIONS

Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of be International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W.,et al., "The Electrical Discharge of the Electric Eel, Electrophorous Electricus," Zoologica, 1937, 22(1), pp. 1-32.
Cook et al., ACT3: A High-Speed, High-Precision Electrical Impedance Tomograph, IEEE Transactions on Biomedical Engineering, vol. 41, No. 8, Aug. 1994.
Co-pending U.S. Appl. No. 10/571,162, filed Oct. 18, 2006 (published as 2007/0043345 on Feb. 22, 2007).
Co-Pending U.S. Appl. No. 12/432,295, Notice of Allowance and Interview Summary dated Nov. 3, 2016, 9 pages.
Co-Pending U.S. Appl. No. 12/432,295, Advisory Action and Examiner Interview Summary dated Feb. 9, 2016, 5 pages.
Co-Pending U.S. Appl. No. 12/432,295, Amendment with RCE dated Oct. 19, 2016, 9 pages.
Co-Pending U.S. Appl. No. 12/432,295, Appeal Brief and Appendices dated Jul. 25, 2016, 94 pages.
Co-Pending U.S. Appl. No. 12/432,295, filed Apr. 29, 2009.
Co-Pending U.S. Appl. No. 12/432,295, Final Rejection dated Jun. 16, 2014, 14 pages.
Co-Pending U.S. Appl. No. 12/432,295, Final Rejection dated Mar. 21, 2012, 14 pages.
Co-Pending U.S. Appl. No. 12/432,295, Non-Final Office Action dated Nov. 26, 2013, 15 pages.
Co-Pending U.S. Appl. No. 12/432,295, Non-Final Rejection dated Nov. 10, 2011, 10 pages.
Co-Pending U.S. Appl. No. 12/432,295, Requirement for Restriction/Election dated Aug. 9, 2011, 7 pages.
Co-Pending U.S. Appl. No. 12/432,295, Response to Jun. 16, 2014 Final Rejection filed Oct. 16, 2014, 13 pages.
Co-Pending U.S. Appl. No. 12/432,295, Response to Non-Final Office Action, dated Apr. 28, 2014, 14 pages.
Co-Pending U.S. Appl. No. 12/432,295, Response to Non-Final Rejection dated Jan. 23, 2012, 9 pages.
Co-Pending U.S. Appl. No. 12/432,295, Response to Requirement for Restriction/Election dated Sep. 2, 2011, 2 pages.
Co-Pending U.S. Appl. No. 12/432,295, Response with RCE to Final Rejection dated Jul. 23, 2012, 13 pages.
Co-Pending U.S. Appl. No. 12/491,151, Final Rejection dated Apr. 20, 2012, 8 pages.
Co-Pending U.S. Appl. No. 12/491,151, Non-Final Rejection dated Apr. 4, 2014, 12 pages.
Co-Pending U.S. Appl. No. 12/491,151, Non-Final Rejection dated Dec. 28, 2011, 7 pages.
Co-Pending U.S. Appl. No. 12/491,151, Official Notice of Allowance dated Nov. 6, 2014, 15 pages.
Co-Pending U.S. Appl. No. 12/491,151, Requirement for Restriction/Election dated Dec. 2, 2011, 6 pages.
Co-Pending U.S. Appl. No. 12/491,151, Response to Apr. 4, 2014 Non-Final Rejection dated Aug. 22, 2014, 12 pages.
Co-Pending U.S. Appl. No. 12/491,151, Response to Non-Final Rejection dated Mar. 28, 2012, 10 pages.
Co-Pending U.S. Appl. No. 12/491,151, Response to Requirement for Restriction/Election dated Dec. 13, 2011, 2 pages.
Co-Pending U.S. Appl. No. 12/491,151, Response with RCe to Final Rejection dated Aug. 20, 2012, 14 pages.
Co-Pending U.S. Appl. No. 12/491,151, Supplemental Amendment dated Dec. 17, 2012, 6 pages.
Co-Pending U.S. Appl. No. 12/609,779, filed Oct. 30, 2009.
Co-Pending U.S. Appl. No. 12/609,779, Final Rejection dated Oct. 26, 2012, 20 pages.
Co-Pending U.S. Appl. No. 12/609,779, Non-Final Rejection dated May 23, 2012, 17 pages.
Co-Pending U.S. Appl. No. 12/609,779, Notice of Allowance dated Feb. 12, 2013, 7 pages.
Co-Pending U.S. Appl. No. 12/609,779, Notice of Allowance dated May 23, 2013, 2 pages.
Co-Pending U.S. Appl. No. 12/609,779, Response to Non-Final Rejection dated Sep. 24, 2012, 37 pages.
Co-Pending U.S. Appl. No. 12/609,779, Response with RCE to Final Rejection dated Dec. 18, 2012, 20 pages.
Co-Pending U.S. Appl. No. 12/751,826, filed Mar. 31, 2010 (published as 2010/0250209 on Sep. 30, 2010).
Co-pending U.S. Appl. No. 12/751,854, filed Mar. 31, 2010 (published as 2010/0249771 on Sep. 30, 2010).
Co-Pending U.S. Appl. No. 12/757,901, filed Apr. 9, 2010.
Co-Pending U.S. Appl. No. 12/906,923, filed Oct. 18, 2010.
Co-Pending U.S. Appl. No. 13/989,175, Notice of Allowance dated Sep. 1, 2017, 7 pages.
Co-Pending U.S. Appl. No. 13/989,175, Office Actions and Responses through Aug. 30, 2017, 172 pages.
Co-Pending U.S. Appl. No. 13/989,175, Supplemental Notice of Allowability, dated Dec. 6, 2017, 4 pages.
Co-Pending U.S. Appl. No. 13/989,175, Supplemental Notice of Allowability, dated Nov. 30, 2017, 4 pages.
Co-Pending U.S. Appl. No. 14/558,631, filed Dec. 2, 2014.
Co-Pending U.S. Appl. No. 14/686,380, filed Apr. 14, 2015 and Published as US 2015/0289923 on Oct. 15, 2015.
Co-Pending U.S. Appl. No. 14/808,679, filed Jul. 24, 2015 and Published as U.S. Publication No. 2015/0327944 on Nov. 19, 2015.
Co-pending U.S. Appl. No. 15/186,653, filed Jun. 20, 2016.
Co-Pending U.S. Appl. No. 15/310,114, filed Nov. 10, 2016.
Co-Pending U.S. Appl. No. 15/423,986, filed Feb. 3, 2017.
Co-pending U.S. Appl. No. 15/424,335, filed Feb. 3, 2017.
Co-pending U.S. Appl. No. 15/881,414, filed Jan. 26, 2018.
Co-pending U.S. Appl. No. 16/177,745, filed Nov. 1, 2018.
Co-pending Application No. EP 11842994, Extended European Search Report, dated Apr. 9, 2014, 34 pages.
Co-Pending Application No. EP 11842994.3, Communication Pursuant to Rules 70(2) and 70a(2) EPC dated Apr. 28, 2014, 1 page.
Co-Pending Application No. EP 11842994.3, Extended European Search Report dated Apr. 9, 2014, 34 pages.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US10/53077, filed Oct. 18, 2010.
Co-Pending Application No. PCT/US11/62067, filed Nov. 23, 2011.
Co-Pending Application No. PCT/US11/66239, filed Dec. 20, 2011.
Faroja, M., et al., "Irreversible Electroporation Ablation: Is the entire Damage Nonthermal?", Radiology, 266(2), 462-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.

(56) References Cited

OTHER PUBLICATIONS

Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed, Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.

Gowrishankar T.R., et al., "Microdosimetry for conventional and supra-electroporation in cells with organelles". Biochem Biophys Res Commun, 341(4): p. 1266-76 (2006).
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. ii114.
Ho, et al., Electroporation of Cell Membranes: A Review, Critical Reviews in Biotechnology, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
IvanušA, et al., MRI Macromolecular Contrast Agents as Indicators of Changed Tumor Blood Flow, Radiol. Oncol. 2001; 35(2): 139-47.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than

(56) References Cited

OTHER PUBLICATIONS determined by 18FFDG-microPET or external caliper." BMC medical Imaging vol. 8:16, 9 Pages (2008).

Jossinet et al., Electrical Impedance Endo-Tomography: Imaging Tissue From Inside, IEEE Transactions on Medical Imaging, vol. 21, No. 6, Jun. 2002, pp. 560-565.

Kingham et al., "Ablation of perivascular hepatic malignant tumors with irreversible electroporation." Journal of the American College of Surgeons, 2012. 215(3), p. 379-387.

Kinoshita and Tsong, "Formation and resealing of pores of controlled sizes in human erythrocyte membrane." Nature, vol. 268 (1977) pp. 438-441.

Kinosita and Tsong, "Voltage-induced pore formation and hemolysis of human erythrocytes." Biochimica et Biophysica Acta (BBA)-Biomembranes, 471 (1977) pp. 227-242.

Kinosita et al., "Electroporation of cell membrane visualized under a pulsed-laser fluorescence microscope." Biophysical Journal, vol. 53, pp. 1015-1019 (1988).

Kinosita, et al., Hemolysis of Human Erythrocytes by a Transient Electric Field, Proc. Natl. Acad. Sci. USA, vol. 74, No. 5, pp. 1923-1927, 1977.

Kirson et al., "Alternating electric fields arrest cell proliferation in animal tumor models and human brain tumors." Proceedings of the National Academy of Sciences vol. 104, pp. 10152-10157 (2007).

Kotnik and Miklavcic, "Theoretical evaluation of voltage inducement on internal membranes of biological cells exposed to electric fields." Biophysical Journal, vol. 90(2), pp. 480-491 (2006).

Kotnik et al., "Sensitivity of transmembrane voltage induced by applied electric fields—A theoretical analysis", Bioelectrochemistry and Bioenergetics,vol. 43, Issue 2, 1997, pp. 285-291.

Kotnik, T. and D. Miklavcic, "Theoretical evaluation of the distributed power dissipation in biological cells exposed electric fields", Bioelectromagnetics, 21(5): p. 385-394 (2000).

Kotnik, T., et al., "Cell membrane electropermeabilization by symmetrical bipolar rectangular pulses. Part II. Reduced electrolytic contamination", Bioelectrochemistry, 54(1): p. 91-5 (2001).

Kotnik, T., et al., "Role of pulse shape in cell membrane electropermeabilization", Biochimica Et Biophysica Acta-Biomembranes, 1614(2): p. 193-200 (2003).

Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).

Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).

Laufer et al., "Electrical impedance characterization of normal and cancerous human hepatic tissue." Physiological Measurement, vol. 31, pp. 995-1009 (2010).

Lebar et al., "Inter-pulse interval between rectangular voltage pulses affects electroporation threshold of artificial lipid bilayers." IEEE Transactions on NanoBioscience, vol. 1 (2002) pp. 116-120.

Lee, E. W. et al. Advanced Hepatic Ablation Technique for Creating Complete Cell Death : Irreversible Electroporation. Radiology 255, 426-433, doi:10.1148/radiol.10090337 (2010).

Lee, E.W., et al., "Imaging guided percutaneous irreversible electroporation: ultrasound and immunohistological correlation", Technol Cancer Res Treat 6: 287-294 (2007).

Li, W., et al., "The Effects of Irreversible Electroporation (IRE) on Nerves" PloS One, Apr. 2011, 6(4), e18831.

Liu, et al. Measurement of Pharyngeal Transit Time by Electrical Impedance Tomography, Clin. Phys. Physiol. Meas., 1992, vol. 13, Suppl. A, pp. 197-200.

Long, G., et al., "Targeted Tissue Ablation With Nanosecond Pulses". Ieee Transactions on Biomedical Engineering, 58(8) (2011).

Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.

Lurquin, Gene Transfer by Electroporation, Molecular Biotechnology, vol. 7, 1997.

Lynn, et al., A New Method for the Generation and Use of Focused Ultrasound in Experimental Biology, The Journal of General Physiology, vol. 26, 179-193, 1942.

Maček Lebar and Miklavčič, "Cell electropermeabilization to small molecules in vitro: control by pulse parameters." Radiology and Oncology, vol. 35(3), pp. 193-202 (2001).

Mahmood, F., et al., "Diffusion-Weighted MRI for Verification of Electroporation-Based Treatments", Journal of Membrane Biology 240: 131-138 (2011).

Mahnic-Kalamiza, S., et al., "Educational application for visualization and analysis of electric field strength in multiple electrode electroporation," BMC Med Educ, vol. 12, p. 102, 2012.

Malpica et al., "Grading ovarian serous carcinoma using a two-tier system." The American Journal of Surgical Pathology, vol. 28, pp. 496-504 (2004).

Maor et al., The Effect of Irreversible Electroporation on Blood Vessels, Tech. in Cancer Res. and Treatment, vol. 6, No. 4, Aug. 2007, pp. 307-312.

Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.

Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.

Marszalek et al., "Schwan equation and transmembrane potential induced by alternating electric field." Biophysical Journal, vol. 58, pp. 1053-1058 (1990).

Martin, n.R.C.G., et al., "Irreversible electroporation therapy in the management of locally advanced pancreatic adenocarcinoma." Journal of the American College of Surgeons, 2012. 215(3): p. 361-369.

Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.

Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.

Miklavčič, et al., The Importance of Electric Field Distribution for Effective in Vivo Electroporation of Tissues, Biophysical Journal, vol. 74, May 1998, pp. 2152-2158.

Miller, L., et al., Cancer cells ablation with irreversible electroporation, Technology in Cancer Research and Treatment 4 (2005) 699-706.

Mir et al., "Mechanisms of Electrochemotherapy" Advanced Drug Delivery Reviews 35:107-118 (1999).

Mir, et al., Effective Treatment of Cutaneous and Subcutaneous Malignant Tumours by Electrochemotherapy, British Journal of Cancer, vol. 77, No. 12, pp. 2336-2342, 1998.

Mir, et al., Electrochemotherapy Potentiation of Antitumour Effect of Bleomycin by Local Electric Pulses, European Journal of Cancer, vol. 27, No. 1, pp. 68-72, 1991.

Mir, et al., Electrochemotherapy, a Novel Antitumor Treatment: First Clinical Trial, C.R. Acad. Sci. Paris, Ser. III, vol. 313, pp. 613-618, 1991.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, L.M., et al., Electric Pulse-Mediated Gene Delivery to Various Animal Tissues, in Advances in Genetics, Academic Press, 2005, p. 83-114.

Mir, Therapeutic Perspectives of In Vivo Cell Electropermeabilization, Bioelectrochemistry, vol. 53, pp. 1-10, 2000.

Mulhall et al., "Cancer, pre-cancer and normal oral cells distinguished by dielectrophoresis." Analytical and Bioanalytical Chemistry, vol. 401, pp. 2455-2463 (2011).

(56) References Cited

OTHER PUBLICATIONS

Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Co-Pending Application No. PCT/US15/30429, filed May 12, 2015.
Co-Pending Application No. PCT/US15/30429, International Search Report and Written Opinion dated Oct. 16, 2015, 19 pages.
Co-pending Application No. PCT/US2010/029243, filed Mar. 30, 2010, published as WO 2010/117806 on Oct. 14, 2010.
Co-Pending Application No. PCT/US2015/030429, Published on Nov. 19, 2015 as WO 2015/175570.
Co-Pending U.S. Appl. No. 12/432,295, Response to Jun. 23, 2015 Non-Final Office Action dated Oct. 23, 2015, 46 pages.
Co-Pending U.S. Appl. No. 12/432,295, Final Office Action dated Nov. 25, 2015, 14 pages.
Co-Pending U.S. Appl. No. 12/432,295, Non-Final Office Action dated Jun. 23, 2015, 12 pages.
Co-Pending U.S. Appl. No. 12/432,295, Response to Nov. 25, 2015 Final Office Action, filed Jan. 25, 2016, 12 pages.
Co-Pending U.S. Appl. No. 12/432,295, Supplemental Response After RCE, filed Nov. 17, 2014, 9 pages.
Co-Pending U.S. Appl. No. 12/491,151, filed Jun. 24, 2009.
Co-Pending U.S. Appl. No. 13/332,133, filed Dec. 20, 2011.
Co-Pending U.S. Appl. No. 13/550,307, filed Aug. 13, 2018 Applicant-Initiated Interview Summary, 3 pages.
Co-Pending U.S. Appl. No. 13/550,307, Final Office Action dated Dec. 5, 2018, 17 pages.
Co-Pending U.S. Appl. No. 13/550,307, Final Office Action dated May 23, 2017, 13 pages.
Co-Pending U.S. Appl. No. 13/550,307, Final Office Action dated Oct. 23, 2015, 10 pages.
Co-Pending U.S. Appl. No. 13/550,307, Interview Summary and Misc. Internal Document dated Dec. 23, 2016, 4 pages.
Co-Pending U.S. Appl. No. 13/550,307, Non-Final Office Action dated Apr. 15, 2015, 10 pages.
Co-Pending U.S. Appl. No. 13/550,307, Non-Final Office Action dated Aug. 26, 2016, 12 pages.
Co-Pending U.S. Appl. No. 13/550,307, Office Actions and Responses through Mar. 2018, 133 pages.
Co-Pending U.S. Appl. No. 13/550,307, Response to Aug. 26, 2016 Non-Final Office Action, filed Nov. 28, 2016, 14 pages.
Co-Pending U.S. Appl. No. 13/550,307, Response to Final Office Action filed Feb. 23, 2016, 9 pages.
Co-Pending U.S. Appl. No. 13/550,307, Response to Mar. 14, 2018 Non-Final Office Action dated Jul. 16, 2018, 12 pages.
Co-Pending U.S. Appl. No. 13/550,307, Response to May 23, 2017 Final Office Action dated Aug. 23, 2017, 11 pages.
Co-Pending U.S. Appl. No. 13/550,307, Response to Non-Final Office Action filed Jul. 15, 2015, 9 pages.
Co-Pending U.S. Appl. No. 13/550,307, Response to Restriction Requirement filed Mar. 9, 2015, 3 pages.
Co-Pending U.S. Appl. No. 13/550,307, Restriction Requirement dated Jan. 7, 2015, 8 pages.
Co-Pending U.S. Appl. No. 13/550,307, Supplemental Amendment filed Dec. 21, 2016, 9 pages.
Co-Pending U.S. Appl. No. 13/550,307, filed Jul. 16, 2012.
Co-Pending U.S. Appl. No. 13/919,640, filed Jun. 17, 2013.
Co-Pending U.S. Appl. No. 13/958,152, Final Office Action dated Dec. 22, 2017, 19 pages.
Co-Pending U.S. Appl. No. 13/958,152, Interview and Supplemental Response to Office Action Mar. 2-3, 2017, 12 pages.
Co-Pending U.S. Appl. No. 13/958,152, Interview Summary dated Mar. 2, 2017, 4 pages.
Co-Pending U.S. Appl. No. 13/958,152, Non-Final Office Action dated Jun. 15, 2017, 18 pages.
Co-Pending U.S. Appl. No. 13/958,152, Non-Final Office Action dated Oct. 18, 2018, 20 pages.
Co-Pending U.S. Appl. No. 13/958,152, Office Actions and Responses from Jan. 2015 through Oct. 21, 2016.
Co-Pending U.S. Appl. No. 13/958,152, Response to Jun. 15, 2017 Non-Final Office Action dated Sep. 15, 2017, 10 pages.
Co-Pending U.S. Appl. No. 13/958,152, Response to Oct. 21, 2016 Non-Final Office Action, filed Jan. 23, 2017, 25 pages.
Co-Pending U.S. Appl. No. 13/958,152, filed Aug. 2, 2013.
Co-Pending U.S. Appl. No. 14/012,832, filed Aug. 28, 2013.
Co-Pending U.S. Appl. No. 14/017,210, Acceptance of 312 Amendment dated Sep. 12, 2018, 1 page.
Co-Pending U.S. Appl. No. 14/017,210, AFCP datead Aug. 13, 2018, 9 pages.
Co-Pending U.S. Appl. No. 14/017,210, Final Office Action dated Apr. 11, 2018, 10 pages.
Co-Pending U.S. Appl. No. 14/017,210, Final Office Action dated Aug. 30, 2016, 11 pages.
Co-Pending U.S. Appl. No. 14/017,210, Final Office Action dated May 1, 2017, 11 pages.
Co-Pending U.S. Appl. No. 14/017,210, Non-Final Office Action dated Dec. 15, 2016, 8 pages.
Co-Pending U.S. Appl. No. 14/017,210, Non-Final Office Action dated Oct. 25, 2017, 9 pages.
Co-Pending U.S. Appl. No. 14/017,210, Notice of Allowance dated Sep. 12, 2018, 7 pages.
Co-Pending U.S. Appl. No. 14/017,210, Priority Petition Dec. 11, 2015, 5 pages.
Co-Pending U.S. Appl. No. 14/017,210, RCE dated Aug. 1, 2017, 13 pages.
Co-Pending U.S. Appl. No. 14/017,210, Response to Aug. 30, 2016 Final Office Action, dated Nov. 30, 2016, 10 pages.
Co-pending U.S. Appl. No. 16/275,429, filed Feb. 14, 2019.
Co-pending U.S. Appl. No. 16/280,511, filed Feb. 20, 2019.
Neal II, R. E., et al., "Experimental characterization and numerical modeling of tissue electrical conductivity during pulsed electric fields for irreversible electroporation treatment planning," IEEE Trans Biomed Eng., vol. 59:4, pp. 1076-1085. Epub 2012 Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).

(56) References Cited

OTHER PUBLICATIONS

Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Paszek et al., "Tensional homeostasis and the malignant phenotype." Cancer Cell, vol. 8, pp. 241-254 (2005).
Pavselj, N. et al. The course of tissue permeabilization studied on a mathematical model of a subcutaneous tumor in small animals. IEEE Trans Biomed Eng 52, 1373-1381 (2005).
PCT International Preliminary Report on Patentability of Corresponding International Application No. PCT/2011/062067, dated May 28, 2013.
PCT International Preliminary Report on Patentability of Corresponding International Application No. PCT/2011/066239, dated Jun. 25, 2013.
PCT International Search Report (dated Aug. 2, 2011), Written Opinion (dated Aug. 2, 2011), and International Preliminary Report on Patentability (dated Apr. 17, 2012) of PCT/US10/53077.
PCT International Search Report (dated Aug. 22, 2012), and Written Opinion (dated Aug. 22, 2012) of PCT/US11/66239.
PCT International Search Report (dated Aug. 26, 2005), Written Opinion (dated Aug. 26, 2005), and International Preliminary Report on Patentability (dated Jun. 26, 2006) of PCT/US2004/043477.
PCT International Search Report (dated Jan. 19, 2010), Written Opinion (dated Jan. 19, 2010), and International Preliminary Report on Patentability (dated Jan. 4, 2010) of PCT/US09/62806, 15 pgs.
PCT International Search Report (dated Jul. 15, 2010), Written Opinion (dated Jul. 15, 2010), and International Preliminary Report on Patentability (dated Oct. 11, 2011) from PCT/US2010/030629.
PCT International Search Report (dated Jul. 9, 2009), Written Opinion (dated Jul. 9, 2009), and International Preliminary Report on Patentability (dated Nov. 2, 2010) of PCT/US2009/042100.
PCT International Search Report and Written Opinion (dated Jul. 25, 2012) of PCT/US2011/062067.
PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.
PCT IPRP for PCT/US15/30429, dated Nov. 15, 2016.
Phillips, M., Maor, E. & Rubinsky, B. Non-Thermal Irreversible Electroporation for Tissue Decellularization. J. Biomech. Eng, doi:10.1115/1.4001882 (2010).
Piñero et al., Apoptotic and Necrotic Cell Death Are Both Induced by Electroporation in HL60 Human Promyeloid Leukaemia Cells, Apoptosis, vol. 2, No. 3, 330-336, Aug. 1997.

Polak et al., "On the Electroporation Thresholds of Lipid Bilayers: Molecular Dynamics Simulation Investigations." The Journal of Membrane Biology, vol. 246, pp. 843-850 (2013).
Precision Office Tuna System, When Patient Satisfaction is Your Goal, VidaMed 2001.
Pucihar et al., "Numerical determination of transmembrane voltage induced on irregularly shaped cells." Annals of Biomedical Engineering, vol. 34, pp. 642-652 (2006).
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," Automatika 52(2011) 1, 12-19.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." the Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
SAI Infusion Technologies, "Rabbit Ear Vein Catheters", https://www.sai-infusion.com/products/rabbit-ear-catheters, Aug. 10, 2017 webpage printout, 5 pages.
Salford, L.G., et al., "A new brain tumour therapy combining bleomycin with in vivo electropermeabilization", Biochem. Biophys. Res. Commun., 194(2): 938-943 (1993).
Salmanzadeh et al., "Investigating dielectric properties of different stages of syngeneic murine ovarian cancer cells" Biomicrofluidics 7, 011809 (2013), 12 pages.
Co-Pending U.S. Appl. No. 13/958,152, Response to Dec. 22, 2017 Final Office Action, filed Mar. 22, 2018, 10 pages.
Co-Pending U.S. Appl. No. 13/958,152, Response to Oct. 18, 2018 Non-Final Office Action, filed Jan. 18, 2019, 11 pages.
Co-Pending U.S. Appl. No. 14/017,210, Notice of Allowance (after Dec. 12, 2018 RCE) dated Jan. 9, 2019, 5 pages.
Co-Pending U.S. Appl. No. 14/017,210, Petition dated Dec. 11, 2015, 5 pages.
Co-Pending U.S. Appl. No. 14/017,210, Petition Decision dated Aug. 12, 2016, 9 pages.
Co-Pending U.S. Appl. No. 14/017,210, Petition Decision dated Aug. 2, 2016, 5 pages.
Co-Pending U.S. Appl. No. 14/017,210, RCE dated Nov. 30, 2016, 13 pages.
Co-Pending U.S. Appl. No. 14/017,210, RCE filed Aug. 1, 2017, 13 pages.
Co-Pending U.S. Appl. No. 14/017,210, Response to Non-Final Office Action dated Mar. 8, 2016, 16 pages.
Co-pending U.S. Appl. No. 13/550,307 Notice of panel decision from pre-appeal brief review dated May 16, 2019, 2 pages.
Co-pending U.S. Appl. No. 13/550,307 Pre-appeal brief request for review dated Apr. 4, 2019, 7 pages.
Co-pending U.S. Appl. No. 16/372,520, filed Apr. 2, 2019.
Co-pending U.S. Appl. No. 16/375,878, filed Apr. 5, 2019.

(56) References Cited

OTHER PUBLICATIONS

Co-pending U.S. Appl. No. 16/404,392, filed May 6, 2019.
Co-Pending U.S. Appl. No. 13/958,152, Final Office Action dated May 2, 2019, 17 pages.

\* cited by examiner

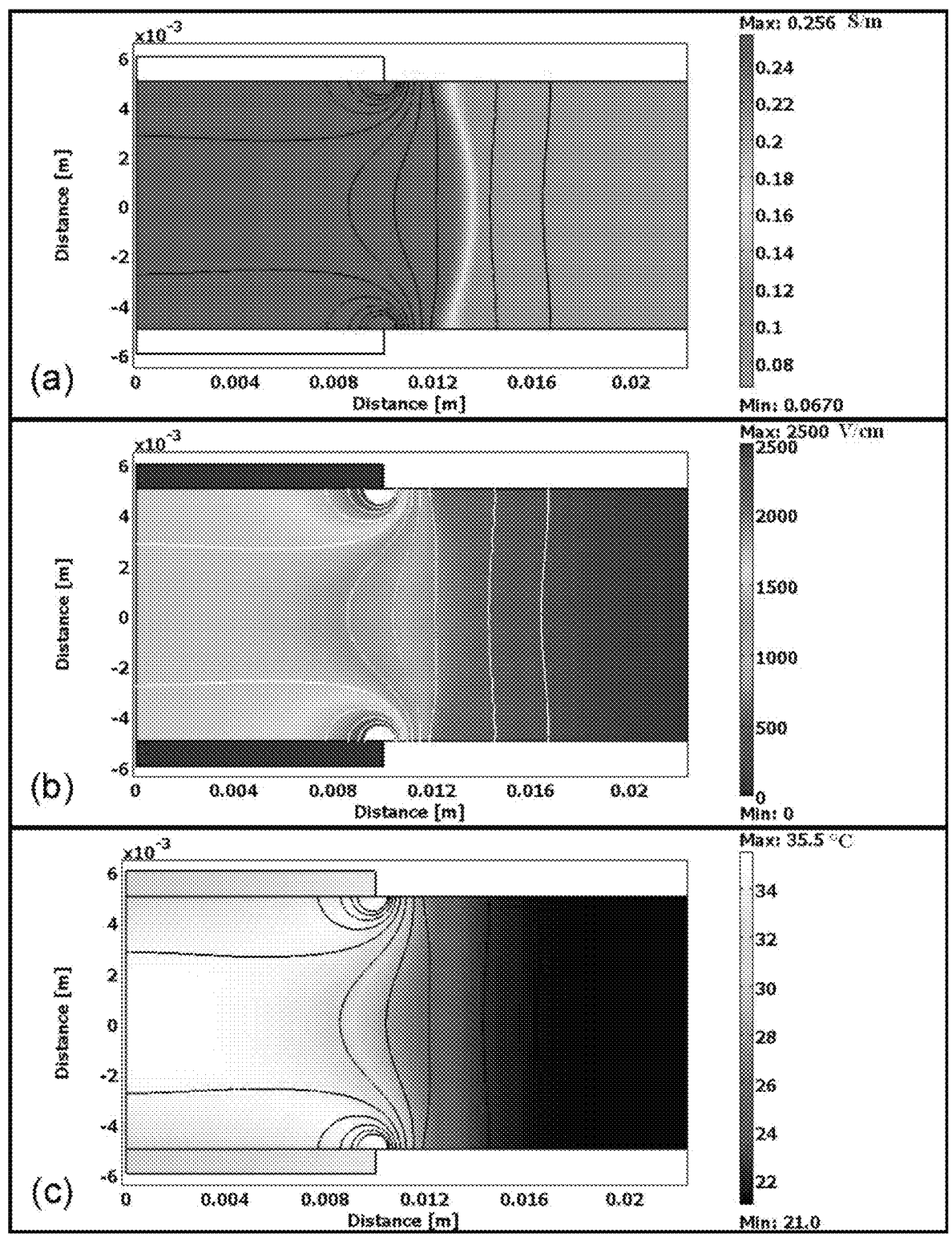
FIGS. 6A-C

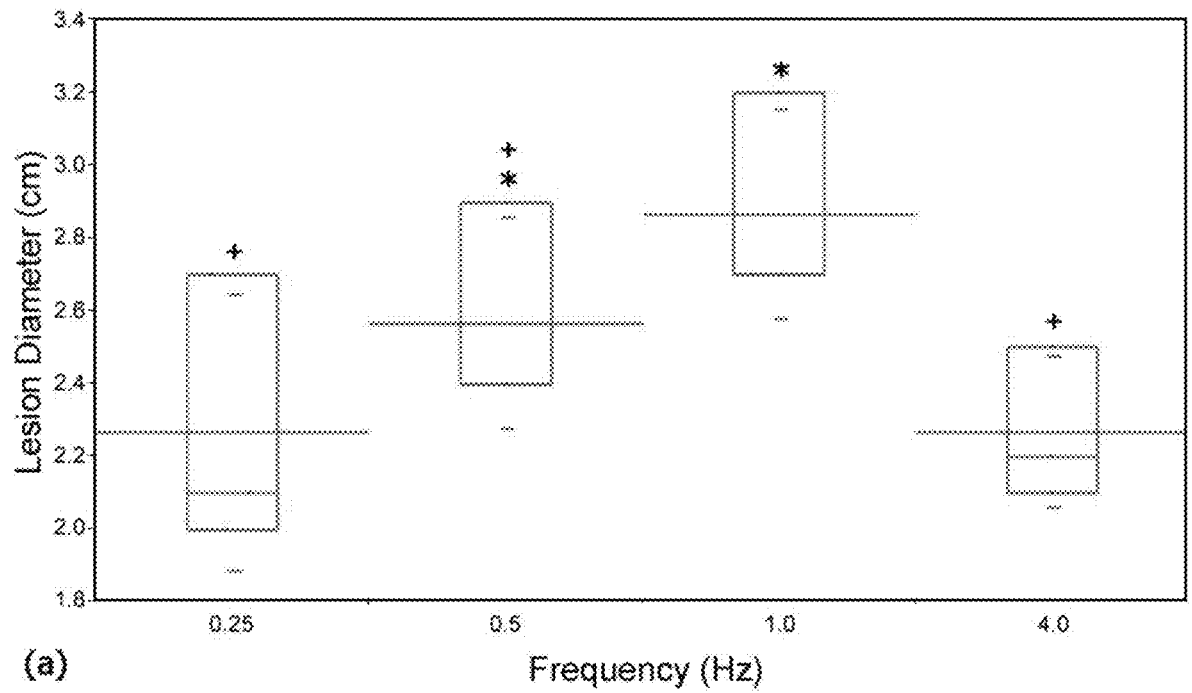
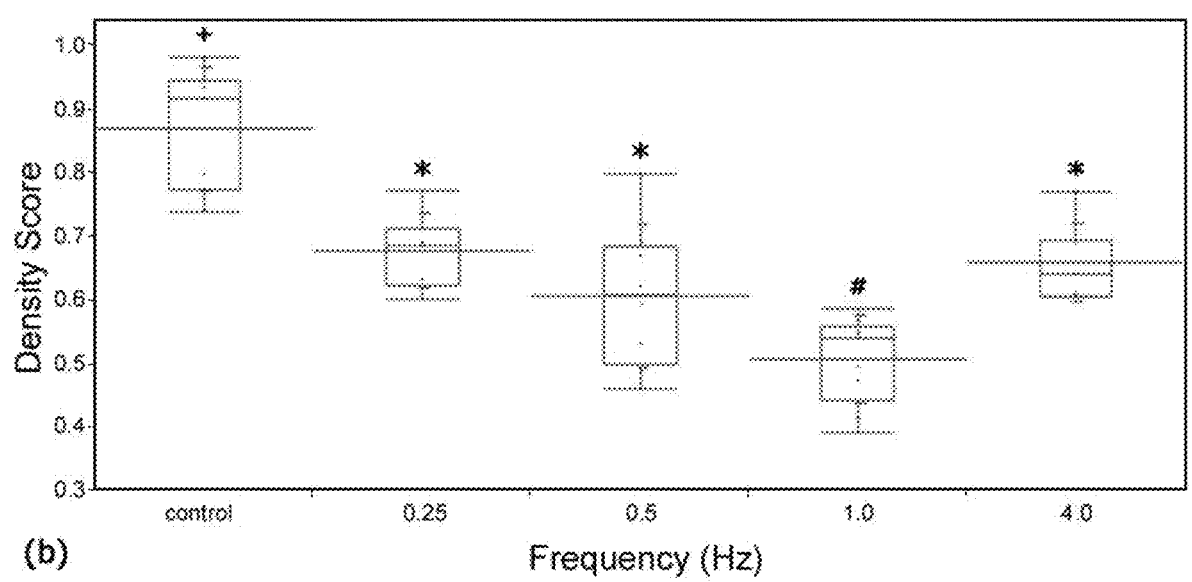
FIGS. 7A-B

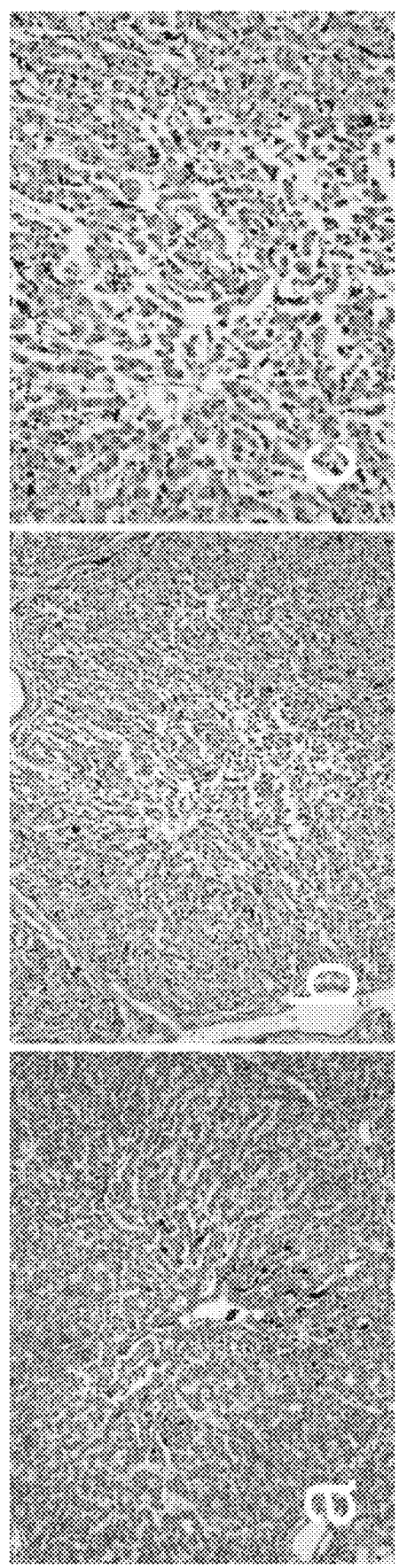

IRREVERSIBLE ELECTROPORATION USING TISSUE VASCULATURE TO TREAT ABERRANT CELL MASSES OR CREATE TISSUE SCAFFOLDS

CROSS-REFERENCE TO RELATED APPLICATIONS

This application claims priority to and is a Divisional Application of U.S. patent application Ser. No. 13/989,175, filed May 23, 2013, which published as U.S. Patent Application Publication No. 2013/0253415 on Sep. 26, 2013, and which issued as U.S. Pat. No. 9,867,652 on Jan. 16, 2018. The '175 application is a National Stage Application under 35 USC § 371 of International Application No. PCT/US11/62067, filed Nov. 23, 2011, which published as International Publication No. WO 2012/071526 on May 31, 2012. The '067 application relies on and claims the benefit of the filing date of U.S. Provisional Patent Application No. 61/416,534, filed Nov. 23, 2010 and is a Continuation-In-Part (CIP) application of U.S. patent application Ser. No. 12/491,151, filed Jun. 24, 2009, which published as U.S. Patent Application Publication No. 2010/0030211 on Feb. 4, 2010, and which issued as U.S. Pat. No. 8,992,517 on Mar. 31, 2015. The '151 application relies on and claims the benefit of the filing date of U.S. Provisional Patent Application Nos. 61/075,216, filed Jun. 24, 2008; 61/125,840, filed Apr. 29, 2008; 61/171,564, filed Apr. 22, 2009; and 61/167,997, filed Apr. 9, 2009. The '067 application is also a CIP application of U.S. patent application Ser. No. 12/432,295, filed Apr. 29, 2009, which published as U.S. Patent Application Publication No. 2009/0269317 on Oct. 29, 2009, and issued as U.S. Pat. No. 9,598,691 on Mar. 21, 2017. The '295 application relies on and claims the benefit of the filing date of U.S. Provisional Patent Application No. 61/125,840, filed Apr. 29, 2008. The entire disclosures of all of these patent applications are hereby incorporated herein by reference in their entireties.

BACKGROUND OF THE INVENTION

Field of the Invention

The present invention relates to the field of medical treatment of diseases and disorders, as well as the field of biomedical engineering. Embodiments of the invention relate to the delivery of Irreversible Electroporation (IRE) through the vasculature of organs to treat tumors embedded deep within the tissue or organ, or to decellularize organs to produce a scaffold from existing animal tissue, such as human tissue, with the existing vasculature intact. In addition, embodiments of the invention may be used in the treatment of malignant and benign diseases through the enhanced administration of therapeutic drugs or gene constructs by facilitating reversible electroporation. Further, vascular electrical conduits may be used to administer other therapies that rely on the delivery of electrical energy to a targeted region of the body or organ tissue with the existing vasculature intact.

Description of Related Art

The ablation of unwanted soft tissue can be achieved by many means, including surgical excision, application of excessive amount of ionizing radiation or other forms of energy (excessive heating and cooling), exposure to cytotoxic chemicals, or by a combination of these means. It is common to use these means to destroy neoplasms. Treatments known in the art involve surgical intervention to physically remove the aberrant cell mass, radiation to kill the cells of the aberrant cell mass, exposure of aberrant cells to toxic chemicals (i.e., chemotherapy), or a combination of such techniques. While each treatment modality has shown significant effectiveness in treatment of various cell proliferative diseases, no one technique has been shown to be highly effective at treating all types of cell proliferative diseases and disorders.

While surgical intervention is effective at removal of solid tumors on tissues and organs that are physically accessible and capable of sustaining physical damage or capable of regeneration, surgical intervention can be difficult to perform on tumors that are not readily accessible or on organs that do not regenerate. In these cases, surgical intervention can often involve substantial physical damage to the patient, requiring extensive recuperation times and follow-on treatments. At other times, the extensive growth of the neoplasm prevents removal, since attempts at removal would likely kill the patient. Likewise, treatment with radiation can result in collateral damage to tissue surrounding the tumor, and can cause long-lasting side-effects, which can lower the quality of life of the patient. Chemotherapeutic treatments can cause systemic damage to the patient, and can result in significant side effects that might require a long recuperation period or cause permanent damage to tissues and organs.

Recent work by the inventors has focused on the ablation of unwanted soft tissue (malignant tumors) by application of excessive electrical energy, using a technique termed Irreversible Electroporation (IRE). Successful control and/or ablation of soft tissue sarcoma and malignant glioma have been achieved. Irreversible electroporation (IRE) involves placing electrodes within or near the targeted region to deliver a series of low energy, microsecond electric pulses. These pulses permanently destabilize the cell membranes of the targeted tissue (e.g., tumor), thereby killing the cells. When applied with precision, IRE does not damage major blood vessels, does not require the use of drugs and non-thermally kills neoplastic cells in a controllable manner, without significantly damaging surrounding tissue.

Other methods of treating disease involve replacing diseased tissue or organs. Over the past twenty years, organ transplantation has become a standard care for patients diagnosed with end stage diseases like cirrhosis, renal failure, etc. The extraordinary success of liver transplantation, with 90% and 75% survival rates after 1 and 5 years, respectively, has led to a progressively increasing number of patients awaiting transplant. Chan, S. C. et al., A decade of right liver adult-to-adult living donor liver transplantation—The recipient mid-term outcomes. *Annals of Surgery* 248, 411-418, doi: 10.1097/SLA.0b013e31818584e6 (2008) ("Chan 2008").

According to the United Network of Organ Sharing (UNOS), there are over 108,000 candidates in the US alone currently waiting for organ transplants including kidney, liver, heart, lung, and many others. Of those, there are over 16,000 candidates in immediate (one year) need of a liver transplant, and at least 100,000 additional patients with advanced liver disease who would benefit from one. In 2009, there were fewer than 7,000 liver transplants from both living and deceased donors. *United Network of Organ Sharing*, <http://www.unos.org> (2010).

Standard liver transplantation in the US is usually predicated on organ removal from the donor coincident with the onset of brainstem death. See Kootstra. G., Daemen. J. H. C. & Oomen. A. P. A. Categories of Non-Heart-Beating Donors, *Transplant. Proc.* 27, 2893-2894 (1995); Rigotti, P. et al. Non-Heart-beating Donors—An Alternative Organ Source in Kidney Transplantation. *Transplant. Proc.* 23, 2579-2580 (1991); and Balupuri, S. et al. The trouble with kidneys derived from the non heart-beating donor: A single center 10-year experience. *Transplantation* 69, 842-846 (2000).

Despite advances in transplant surgery and general medicine, the number of patients awaiting transplant organs continues to grow, while the supply of organs does not. The growing discrepancy between organ supply and clinical demand is due to a number of factors including an increase in population age, an increasing incidence of diseases requiring liver transplants (hepatocellular carcinoma and infection with hepatitis viruses), rapid organ degradation (hours) after donation, mismatches created by histocompatibility and other immunologic phenomena, and size mismatches between organs and potential recipients (including pediatric patients), transplantation is the only workable treatment for patients suffering end stage liver disease (Murray, K. F. & Carithers, R. L. AASLD practice guidelines: Evaluation of the patient for liver transplantation. *Hepatology* 41, 1407-1432, doi: 10.1002/hep.20704 (2005)); increased incidence of non-alcoholic fatty liver disease (Amarapurkar. D. N. et al. How common is non-alcoholic fatty liver disease in the Asia-Pacific region and are there local differences? *J. Gastroenterol. Hepatol.* 22, 788-793, doi: 10.1111/j.1440-1746.2007.05042.x (2007)): and acceptance of transplantation for patients with metabolic or congenital diseases (Miro. J. M., Laguno, M., Moreno, A., Rimola, A. & Hosp Clin, O. L. T. H. I. V. W. G. Management of end stage liver disease (ESLD): What is the current role of orthotopic liver transplantation (OLT)? *J. Hepatol.* 44, S140-S145, doi: 10.1016/j.jhep.2005.11.028 (2006)).

Organ supply is constrained by obstacles that impede acquisition. For example, the requirement for organ removal coincident with brainstem death necessitates the use of hospital resources to maintain artificial life support. As a result, organ donation may be problematic when intensive care resources are strained. Fabre. Report of the British Transplantation Society Working Party on Organ Donation. (1995). Use of life support for preservation of potential organ donations has been ethically debated (See Feest, T. G. et al., Protocol for Increasing Organ Donation After Cerebrovascular Deaths in a District General Hospital, *Lancet* 335, 1133-1135 (1990); and Riad, H. & Nicholls, A., An Ethical Debate Elective Ventilation of Potential Organ Donors, *Br. Med. J.* 310, 714-715 (1995)), and donation refusal is common in regions where social, cultural, and religious pressures place constraints on organ procurement.

The increasing gap between organ donation and supply to patients has caused an increased interest in alternative organ sources. Perera, M., Mirza. D. F. & Elias, E. Liver transplantation: Issues for the next 20 years. *J. Gastroenterol. Hepatol.* 24, S124-S131, doi: 10.1111/j.1440-1746.2009.06081.x (2009). Developing engineered materials to replicate the structure and function of organs has been met with limited success. Large volumes of poorly-organized cells and tissues cannot be implanted due to the initial limited diffusion of oxygen, nutrients and waste. Folkman, J. Self-Regulation of Growth In 3 Dimensions. *Journal of Experimental Medicine* 338 (1973); and Kaufman, D. S., Hanson, E. T., Lewis, R. L., Auerbach, R. & Thomson, J. A. Hematopoietic colony-forming cells derived from human embryonic stem cells. *Proc. Natl. Acad. Sci. U.S.A.* 98, 10716-10721 (2001).

Despite this, researchers have made some progress toward partial organ regeneration. For instance, mouse renal cells, grown on decellularized collagen matrices and implanted into athymic mice, developed nephron-like structures after 8 weeks. Atala, A. Engineering organs. *Curr. Opin. Biotechnol.* 20, 575-592, doi: 10.1016/j.copbio.2009.10.003 (2009) ("Atala 2009"). In addition, five millimeter thick porous polyvinyl-alcohol (PVA) constructs, implanted in mice and then injected with hepatocytes, developed liver-like morphology over the course of one year. Kaufmann, P. M. et al. Long-term hepatocyte transplantation using three-dimensional matrices. *Transplant. Proc.* 31, 1928-1929 (1999) ("Kaufmann 1999"). Cell survival and proliferation in each of these structures was limited to a few millimeters from a nutrient source.

For the development and differentiation of full organs suitable for human transplantation, structures that provide microvasculature needed for the delivery of nutrients throughout the tissue and a physical semirigid matrix for cellular organization and anchorage must be developed. See Atala 2009: Kaufmann 1999: and Atala, A. Experimental and clinical experience with tissue engineering techniques for urethral reconstruction. *Urologic Clinics of North America* 29, 485-+(2002). Traditional top-down manufacturing techniques are currently unable to produce a hierarchical vascular structure which, in human organs, ranges in size from a several centimeters (vena cava, for example) down to only a few micrometers (most capillaries), a scale spanning more than four orders of magnitude. Microfabrication techniques can replicate some features of the complex architecture of mammalian microvasculature, but current processes fail to extend into the macro-scale. Structures which have features spanning multiple length scales are currently only fabricated through biological mechanisms and the relatively new field of biofabrication has developed, with the goal of utilizing and manipulating these processes.

Bioengineered tissues have been fabricated through a number of schemes, including direct printing and biospraying, in which cells and a supporting matrix are simultaneously deposited to form a complex network. See Mironov, V. et al. Organ printing: Tissue spheroids as building blocks. *Biomaterials* 30, 2164-2174, doi: 10.1016/j.biomaterials.2008.12.084 (2009); Nakamura. M. et al. Biocompatible inkjet printing technique for designed seeding of individual living cells. *Tissue Engineering* 11, 1658-1666 (2005); and Campbell, P. G. & Weiss, L. E. Tissue engineering with the aid of inkjet printers. *Expert Opin. Biol. Ther.* 7, 1123-1127, doi: 10.1517/14712598.7.8.1123 (2007). Centrifugal forces have been employed to create cross-linked hydrogels, with dense embedded cellular networks in tubular structures. Kasyanov, V. A. et al. Rapid biofabrication of tubular tissue constructs by centrifugal casting in a decellularized natural scaffold with laser-machined micropores. *J. Mater. Sci.-Mater. Med.* 20, 329-337, doi: 10.1007/s10856-008-3590-3 (2009). Dielectrophoretic (Albrecht. D. R., Sah, R. L. & Bhatia, S. N. Geometric and material determinants of patterning efficiency by dielectrophoresis. *Biophys. J.* 87, 2131-2147, doi: 10.1529/biophysj.104.039511 (2004)) and magnetic forces (Mironov, V., Kasvanov, V. & Markwald, R. R. Nanotechnology in vascular tissue engineering: from nanoscaffolding towards rapid vessel biofabrication. *Trends Biotechnol.* 26, 338-344, doi: 10.1016/j.tibtech.2008.03.001 (2008)) have been employed to guide the arrangement of cells within synthetic matrices and cells embedded in a bio-polymer have been electrospun into tissue constructs (Stankus, J. J., Guan, J. J., Fujimoto, K. & Wagner, W. R. Microintegrating smooth muscle cells into a biodegradable, elastomeric fiber matrix. *Biomaterials* 27, 735-744, doi: 10.1016/j.biomaterials.2005.06.020 (2006)). These techniques attempt to distribute cells within a suitable synthetically-fabricated network, leaving the embedded cells to reorganize into an optimal structure.

Decellularization of existing tissues extends the concept of biofabrication by taking advantage of the body's natural programming to create a complete tissue, including a functional vascular network. Rat liver extracellular matrix constructs have been created using chemical decellularization and reseeding. Baptista, P. M. et al. *Generation of a Three-Dimensional Liver Bioscaffold with an Intact Vascular Network for Whole Organ Engineering* (Wake Forest Institue for Regnerative Medicine Harvard-MIT Division of Health, Science, and Technology Rice University, 2009). Decellularized rat hearts, reseeded with multiple cell types, can contract and have the ability to generate pumping pressures. Ott, H. C. et al. Perfusion-decellularized matrix: using nature's platform to engineer a bioartificial heart. *Nature Medicine* 14, 213-221, doi: 10.1038/nm1684 (2008). Challenges to chemical decellularization techniques include the potential for detergents to damage ECM components, the potential to create and deposit toxins, and the inherent difficulty of scaling these techniques up from small rat organs to larger organs. These challenges must be overcome before decellularized organs can successfully be translated to the clinical setting.

Xenotransplantation, or the transplantation of animal organs, is one potential solution to future organ shortages. Keeffe, E. B. Liver transplantation: Current status and novel approaches to liver replacement. Gastroenterology 120, 749-762, doi: 10.1053/gast.2001.22583 (2001). Porcine xenotransplants have shown considerable potential, but have failed to become widely accepted or used. Transplantation of porcine pancreatic islets has recently been shown to temporarily reverse diabetes mellitus (See Cardona, K. et al. Long-term survival of neonatal porcine islets in nonhuman primates by targeting costimulation pathways. *Nature Medicine* 12, 304-306, doi: 10.1038/nm1375 (2006); and Hering, B. J. et al. Prolonged diabetes reversal after intraportal xenotransplantation of wild-type porcine islets in immunosuppressed nonhuman primates. *Nature Medicine* 12, 301-303, doi: 10.1038/nm1369 (2006)) and the use of T-cell tolerance protocols have demonstrated the potential for long-term kidney transplantation in nonhuman primates. Yamada, K. et al. Marked prolongation of porcine renal xenograft survival in baboons through the use of alpha 1,3-galactosyltransferase gene-knockout donors and the cotransplantation of vascularized thymic tissue. *Nature Medicine* 11, 32-34, doi: 10.1038/nm1 172 (2005).

Additionally, porcine livers have demonstrated the ability to clear ammonium and restore coagulation while under short term perfusion of human plasma. Chari, R. S. et al. Brief Report—Treatment of Hepatic Failure with ex-vivo Pig Liver Perfusion Followed by Liver Transplantation, *N. Engl. J. Med.* 331, 234-237 (1994); and Makowka, L. et al., The Use of a Pig Liver Zenograft for Temporary Support of a Patient with Fulminant Hepatic Failure, *Transplantation* 59, 1654-1659 (1995). Unfortunately, the mechanisms of graft loss and rejection in these transplants are still not well understood, and immunological rejection remains the most significant barrier to successful transplantation. Yang, Y. G. & Sykes, M. Xenotransplantation: current status and a perspective on the future. *Nat. Rev. Immunol.* 7, 519-531, doi: 10.1038/nri2099 (2007).

Tissue engineering holds great promise for treating some of the most devastating diseases of our time. Because engineered tissue and organ replacements can be developed in a laboratory, therapies can potentially be delivered on a large scale, for multiple disease states with dramatic reduction in waiting times for patients. The concept of engineering tissue using selective cell transplantation has been applied experimentally and clinically for a variety of disorders, including the successful use of engineered bladder tissue for bladder reconstruction, engineered injectable chondrocytes for the treatment of vesicoureteral reflux and urinary incontinence, and vascular grafts. For clinical use for humans, the process involves the in vitro seeding and attachment of human cells onto a scaffold. Once seeded, the cells proliferate, migrate into the scaffold, and differentiate into the appropriate cell type for the specific tissue of interest while secreting the extracellular matrix components required to create the tissue. The three dimensional structure of the scaffold, and in particular the size of pores and density of the scaffold, is important in successful proliferation and migration of seeded cells to create the tissue of interest. Therefore, the choice of scaffold is crucial to enable the cells to behave in the required manner to produce tissues and organs of the desired shape and size.

To date, scaffolding for tissue engineering has usually consisted of natural and synthetic polymers. Methods known in the art for forming scaffolds for tissue engineering from polymers include solvent-casting, particulate-leaching, gas foaming of polymers, phase separation, and solution casting. Electrospinning is another popular method for creating scaffolds for engineered tissues and organs, but widely used techniques suffer from fundamental manufacturing limitations that have, to date, prevented its clinical translation. These limitations result from the distinct lack of processes capable of creating electrospun structures on the nano-, micro-, and millimeter scales that adequately promote cell growth and function.

Of fundamental importance to the survival of most engineered tissue scaffolds is gas and nutrient exchange. In nature, this is accomplished by virtue of microcirculation, which is the feeding of oxygen and nutrients to tissues and removing waste at the capillary level. However, gas exchange in most engineered tissue scaffolds is typically accomplished passively by diffusion (generally over distances less than 1 mm), or actively by elution of oxygen from specific types of material fibers. Microcirculation is difficult to engineer, particularly because the cross-sectional dimension of a capillary is only about 5 to 10 micrometers ($\mu m$; microns) in diameter. As yet, the manufacturing processes for engineering tissue scaffolds have not been developed and are not capable of creating a network of blood vessels. Currently, there are no known tissue engineering scaffolds with a circulation designed into the structure for gas exchange. As a result, the scaffolds for tissues and organs are limited in size and shape.

In addition to gas exchange, engineered tissue scaffolds must exhibit mechanical properties comparable to the native tissues that they are intended to replace. This is true because the cells that populate native tissues sense physiologic strains, which can help to control tissue growth and function. Most natural hard tissues and soft tissues are elastic or viscoelastic and can, under normal operating conditions, reversibly recover the strains to which they are subjected. Accordingly, engineered tissue constructs possessing the same mechanical properties as the mature extracellular matrix of the native tissue are desirable at the time of implantation into the host, especially load bearing structures like bone, cartilage, or blood vessels.

There are numerous physical, chemical, and enzymatic ways known in the art for preparing scaffolds from natural tissues. Among the most common physical methods for preparing scaffolds are snap freezing, mechanical force (e.g., direct pressure), and mechanical agitation (e.g., sonication). Among the most common chemical methods for preparing scaffolds are alkaline or base treatment, use of non-ionic, ionic, or zwitterionic detergents, use of hypo- or hypertonic solutions, and use of chelating agents. Common enzymatic methods for preparing scaffolds include the use of trypsin, endonucleases, or exonucleases. Currently, it is recognized in the art that, to fully decellularize a tissue to produce a scaffold, two or more of the above-noted ways, and specifically two or more ways from different general classes (i.e., physical, chemical, enzymatic), should be used. Unfortunately, the methods used must be relatively harsh on the tissue so that complete removal of cellular material can be achieved. The harsh treatments invariable degrade the resulting scaffold, destroying vasculature and neural structures.

The most successful scaffolds used in both pre-clinical animal studies and in human clinical applications are biological (natural) and made by decellularizing organs of large animals (e.g., pigs). In general, removal of cells from a tissue or an organ for preparation of a scaffold should leave the complex mixture of structural and functional proteins that constitute the extracellular matrix (ECM). The tissues from which the ECM is harvested, the species of origin, the decellularization methods and the methods of terminal sterilization for these biologic scaffolds vary widely. However, as mentioned above, the decellularization methods are relatively harsh and result in significant destruction or degradation of the extracellular scaffold. Once the scaffold is prepared, human cells are seeded so they can proliferate, migrate, and differentiate into the specific tissue. The intent of most decellularization processes is to minimize the disruption to the underlying scaffold and thus retain native mechanical properties and biologic properties of the tissue. However, to date this intent has not been achieved. Snap freezing has been used frequently for decellularization of tendinous, ligamentous, and nerve tissue. By rapidly freezing a tissue, intracellular ice crystals form that disrupt cellular membranes and cause cell lysis. The rate of temperature change must be carefully controlled to prevent the ice formation from disrupting the ECM as well. While freezing can be an effective method of cell lysis, it must be followed by processes to remove the cellular material from the tissue.

Cells can be lysed by applying direct pressure to tissue, but this method is only effective for tissues or organs that are not characterized by densely organized ECM (e.g., liver, lung). Mechanical force has also been used to delaminate layers of tissue from organs that are characterized by natural planes of dissection, such as the small intestine and the urinary bladder. These methods are effective, and cause minimal disruption to the three-dimensional architecture of the ECM within these tissues. Furthermore, mechanical agitation and sonication have been utilized simultaneously with chemical treatment to assist in cell lysis and removal of cellular debris. Mechanical agitation can be applied by using a magnetic stir plate, an orbital shaker, or a low profile roller. There have been no studies performed to determine the optimal magnitude or frequency of sonication for disruption of cells, but a standard ultrasonic cleaner appears to be effective. As noted above, currently used physical treatments are generally insufficient to achieve complete decellularization, and must be combined with a secondary treatment, typically a chemical treatment. Enzymatic treatments, such as trypsin, and chemical treatment, such as ionic solutions and detergents, disrupt cell membranes and the bonds responsible for intercellular and extracellular connections. Therefore, they are often used as a second step in decellularization, after gross disruption by mechanical means.

Although advances have been made recently in the field of IRE and the concept of treatment of tumors with IRE has been established, the present inventors have recognized that there still exists a need in the art for improved devices and methods for ablating diseased tissues using IRE. More specifically, the inventors employ the vascular bed of tissues as a physiologic electrode ("Physiologic Vascular Electrode" or "PVE") to selectively ablate cells in soft tissue. Application of this technique ex vivo and in vivo to ablate unwanted cells can be useful for treatment of aggressive, infiltrative and circumscribed neoplasms, as well as a wide variety of applications in tissue engineering, tissue regeneration, and organ transplantation employing biologically-derived tissue constructs.

SUMMARY OF THE INVENTION

The present invention provides novel applications of irreversible and reversible electroporation through the use of existing vasculature within tissues as the conduit for pulse delivery. This methodology results in the separation of "electrodes" of just a few microns, reducing the energy necessary to induce non-thermal ablation of cells and tissues to drastically improve preservation of the extracellular matrix for the development of vascularized tissue constructs. Also provided are clinical implications in the treatment of solid tumors and other in vivo applications, including ones that harness the reversible realm of electroporation, where the electrical fields temporarily increase the permeability of the cells without killing them, facilitating the intracellular transport of exogenous agents.

Use of IRE to decellularize tissue provides a controlled, precise way to destroy cells of a tissue or organ, while leaving the underlying extracellular matrix (ECM), including vascularization and other gross morphological features of the original tissue, intact. The decellularized scaffolds are then suitable for seeding with cells of the appropriate organism.

Where the process is performed ex vivo, the seeded tissue is suitable for implantation into the organism as replacement tissue. In addition to methods of producing scaffolds, the invention also provides the decellularized scaffolds themselves, as well as methods of fabrication of engineered tissues and organs built from such scaffolds. Furthermore, the invention provides for use of the engineered scaffolds and the engineered tissues and organs built from such scaffolds.

More specifically, IRE can be used to focally ablate tissue while leaving the microvasculature intact, using active perfusion of the organ, optionally in combination with administering IRE using the organ vasculature as a pathway for the electrical field. This innovative methodology of using the vasculature as a pathway for IRE pulse delivery is a promising solution for treating tumors embedded deep within tissue (e.g., treating from the inside out) or for full organ scaffold generation.

It is known that plate electrodes and needle type electrodes can be used to deliver IRE to treat tissues and organs. In some cases, however, plate electrodes may not be a preferred solution in ablating tumors or treating organs deep within the organ. For example, plate electrodes are generally placed on an external surface of the organ and may cause unwanted damage to healthy tissue located between the tumor and the outside surface of the organ. Needle electrodes are a viable alternative, as the needles are inserted into the organ to treat a more internal portion of the organ. The needle electrodes, while appearing to be most effective at delivering treatments, must puncture the organ. Additionally, the low thermal dose requirement limits the maximum treated area for each set of treatments and a large number of needle punctures would normally be required to treat the entire organ. Even further, these punctures provide an alternative path for fluids thus compromising perfusion of downstream organ sections. Plate electrodes can be employed to mitigate some of these issues, but introduce limitations of their own. Large plate electrodes can be used to treat considerable sections of liver in one treatment. However, the voltage to distance ratio of an applied treatment will vary greatly over the treated area due to changes in tissue depth. Protocols involving these delivery systems typically lead to compromises which may result in inadequate treatment of the organ.

As an alternative to plate and needle type electrodes, the inventors provide devices, systems, and methods for delivering electrical pulses through the vasculature of a mechanically perfused organ to induce non-thermal cell death in bulk tissue (e.g., liver tissue).

A representative device for administering IRE directly into the vasculature of an organ is shown in FIG. 1, which is a schematic diagram of an embodiment of an IRE mechanical perfusion connection device 10 according to the invention. Connections to the vasculature 15 and the perfusion system can be made through the use of Luer lock connections 20. A one way valve 25 inside the device can be used to prevent back-flow and electrically isolate the organ between mechanically simulated heart beats. The device can comprise electrode 30 and an external electrode 40. Accordingly, such electroporation systems can be connected internally to blood vessels and conductance structures (example: the hepatic vein, hepatic artery, portal vein, and/or bile duct of a liver) such that it does not impede continuous mechanical perfusion. In such preferred focal ablation systems, the protocols can induce cell death of 95% of cells while preserving the extracellular basement membrane of lobule units.

Application of electrical energy through the vascular bed of ex vivo and in vivo tissues can be used to ablate unwanted cells as a means to treat disease and create useful biologically-derived tissue constructs. In addition, this technique can be used to deliver electrical or thermal energy to entire organs (or specific regions) to facilitate other phenomenon. Other therapeutic treatments that can also be applied through the vasculature include reversible electroporation for electro-chemotherapy and electro-gene-therapy, radio frequency ablation, RF induced hyperthermia, and pulsed nanosecond electric fields. Indeed, any therapy that requires a conductive path to deliver energy can be adapted by applying the inventive principles disclosed in this specification.

Embodiments of the invention provide methods wherein the application of varying amounts of energy (both reversible and irreversible electroporation) (e.g., using the vasculature of an organ as conductive pathways) can be modulated to produce a wide range of desirable tissue ablation effects, including selective removal of normal and neoplastic cells.

Application of varying amounts of energy using the vasculature of the organ as conducive pathways can be used for other therapeutic modalities (e.g., electrochemotherapy (ECT), electrogenetherapy (EGT), nanosecond pulsed electric fields (nsPEF), High-frequency Irreversible Electroporation (H-FIRE), radio frequency ablation, or acute hyperthermia) to achieve desirable therapeutic effects.

According to the invention, the effects of energy application (e.g., using the vasculature of an organ as conductive pathways) can be controlled and manipulated by varying the pulse shape, voltage, amperage, duration, repetition rate, and frequency of the energy and/or by the design and positioning of the energizing system.

Other aspects of the invention include controlling and manipulating the effects of energy application (e.g., using the vasculature of an organ as conductive pathways) through the design and use of sophisticated, precision-controlled vascular perfusion systems.

Methods of controlling the effects of energy application, e.g., through pulsed electric fields, according to the invention can include varying the physiology-emulating characteristics of sophisticated, precision-controlled vascular perfusion systems.

Even further, the effects of energy application, e.g., through pulsed electric fields, can be controlled by varying conditions of perfusion and preservation of ex vivo organs and tissues.

Energy application using IRE, e.g., through pulsed electric fields, and its resultant effects can be controlled by varying the conditions of perfusion and preservation of in vivo organs and tissues according to embodiments of the present invention.

The invention also includes methods of controlling the effects of energy application, e.g., using the vasculature of the organ as conductive pathways, by varying the composition of intravascular fluids that function partially or wholly as extensions of the energy application system and protocols.

More particularly, aspects of embodiments of the invention include the following aspects, or combinations thereof. In a first aspect, included is a method of ablating cells comprising: placing one or more electrode in, on, or near an organ or tissue; mechanically perfusing the tissue or organ with a perfusate; and administering an electrical field into the tissue or organ for a sufficient time and at sufficient power to cause electroporation of target cells. In a second aspect, such methods can comprise: inserting the electrode(s) into vasculature of an organ or tissue; mechanically perfusing the tissue or organ with a perfusate through the vasculature; and administering an electrical field into the vasculature for a sufficient time and at sufficient power to cause electroporation of target cells.

In a third aspect, such methods can comprise inserting a first electrode into an artery of the organ and a second electrode into a vein of the organ and electroplating tissue or cells between the electrodes through the vasculature of the organ. Additionally or alternatively, other physiological pathways, such as the ureter or common bile duct can be used to apply energy. Such methods can comprise non-thermal irreversible electroporation of target cells.

A fifth aspect includes any of aspects 1-4, further comprising removing cellular debris from the tissue or organ by mechanical perfusion, physiological perfusion, or physical, chemical, or enzymatic techniques, or any combination thereof.

In a sixth aspect, a tissue scaffold formed from ablation of target cells from a natural tissue source by administering irreversible electroporation to the target cells during perfusion of the tissue is provided by embodiments of the invention. In a seventh aspect, such scaffold of aspect 6 can comprise electroporation administered through vasculature of the tissue. In an eighth aspect, the scaffold of aspect 6 or 7 can comprise an extracellular matrix and vascular structure of a natural tissue source. In a ninth aspect, the scaffold of any of aspects 6-8 can result in the tissue scaffold having a thickness in at least one dimension of about 1-8 cm, or 5-10 cm.

A tenth aspect includes an engineered tissue formed from ablation of target cells from a natural tissue source by administering irreversible electroporation to the target cells during perfusion of the tissue to obtain a tissue scaffold, and reseeding the scaffold with living cells under conditions that permit growth of the living cells on or in the scaffold.

In an eleventh aspect, the engineered tissue of aspect 10 can comprise electroporation administered within vasculature of the natural tissue. In a twelfth aspect, the engineered tissue scaffold of aspect 10 or 11 can comprise a tissue scaffold from an animal (any animal including human) and living cells from a human. A thirteenth aspect includes the engineered tissue scaffold of any of aspects 10-12, wherein the tissue scaffold comprises an extracellular matrix and vascular structure of a natural tissue source. A fourteenth aspect includes the engineered tissue scaffold of any of aspects 10-13, wherein the engineered tissue scaffold has a thickness in at least one dimension of about 1-10 cm. A fifteenth aspect can comprise the engineered tissue scaffold of any of aspects 10-14, which is a heart, a lung, a liver, a kidney, a pancreas, a spleen, a gastrointestinal tract, a urinary bladder, a prostate, an ovary, a brain, an ear, an eye, or skin, or a portion thereof, or any other organ or portion thereof.

In a sixteenth aspect of the invention, included is a device for ablating target cells of a tissue or organ comprising: a perfusion system adapted for delivering a perfusate from an artery to a vein of the tissue or organ vasculature; a first and second electrode each adapted for insertion respectively into the artery and the vein of the tissue or organ vasculature; and a voltage source in operable communication with the electrodes for applying a voltage between the first and second electrodes during perfusion at a voltage and for a time sufficient to perform electroporation of target cells disposed between the first and second electrodes. In a seventeenth aspect of the invention, the device of aspect 16 can comprise electroporation that is non-thermal irreversible electroporation. In an eighteenth aspect of the invention, the device of aspect 16 or 17 can comprise electroporation that is reversible in conjunction with adjuvant macromolecules in the perfusate (either in vivo in a patient's blood or ex vivo in a synthetic perfusate) to promote secondary effects to the electroporated cells.

In a nineteenth aspect, the electrodes can be inserted as described in aspect 3 in living tissue where the electrical energy parameters applied through the targeted region are set to intentionally induce an increase in temperature to induce transport as in mild hyperthermia or thermal destruction of the tissue (radiofrequency ablation).

In a twentieth aspect of embodiments of the invention, any aspect of the invention can be adapted to be performed in a living animal or organ under mechanical perfusion wherein electric pulses are administered to induce an electrical field through the vasculature for a sufficient time and at sufficient power to cause electroporation of target cells to facilitate the introduction of therapeutic gene constructs to treat a disease occurring within the targeted region. Such therapies would be helpful in terms of administering gene therapy, e.g., for islets of pancreas in Type I diabetics to spur production of insulin (diseased tissue, non-cancerous).

In a twenty-first aspect of the invention, any aspect of the invention can be adapted to be performed in a living animal or organ under mechanical perfusion wherein electric pulses are administered to induce an electrical field through the vasculature for a sufficient time and at sufficient power to cause electroporation of target cells to facilitate the introduction of gene constructs to alter the cells to treat a systemic disease. Such therapies are applicable in the context of immunomodulation by introducing genes into tissue such as muscle to produce desired antibodies (healthy tissue used as vessel for therapy).

In a twenty-second aspect of the invention, any aspect of the invention can be adapted to be performed in a living animal or organ under mechanical perfusion wherein electric pulses are administered to induce an electrical field through the vasculature for a sufficient time and at sufficient power to cause electroporation of target cells to facilitate the introduction of therapeutic macromolecules to treat a disease, either within the targeted region or a systemic disease. Such therapies are useful for increasing drug uptake to treat any range of diseases—not just to kill cancer cells, but also any other drugs that could treat a non-cancerous disease. This aspect is similar to aspects 20 and 21, but with drugs instead of genes.

In a twenty-third aspect of the invention, any aspect of the invention can be adapted to be performed in a living animal or organ under mechanical perfusion wherein administration of alternating electric fields through the vasculature produces thermal ablation of a targeted region or entirety of an organ.

In a twenty-fourth aspect, any of the methods of aspects 1-23 can include a therapy selected from electrochemotherapy (ECT), electrogenetherapy (EGT), nanosecond pulsed electric fields (nsPEF), High-frequency Irreversible Electroporation (H-FIRE), radio frequency ablation, or acute hyperthermia.

A twenty-fifth aspect includes methods of any other aspect described herein, comprising or further comprising administering an energy into the vasculature for a sufficient time and at sufficient power to cause death of target cells.

A twenty-sixth aspect is a method of any other aspect described herein, wherein a first electrode is inserted into a blood vessel of the organ and a second electrode is inserted into another blood vessel of the organ and electroporation is administered between the electrodes through the vasculature of the organ.

Likewise, a twenty-seventh aspect is a method of any other aspect described herein, wherein a first electrode is inserted into a blood vessel of the organ and a second electrode is inserted into a fluid duct of the organ and electroporation is administered between the electrodes through the vasculature of the organ.

Even further, a twenty-eighth aspect of the invention is a method of any other aspect described herein, wherein a first electrode is inserted into a blood vessel of the organ, a second electrode is inserted into another blood vessel of the organ, with a treatment region of the organ disposed between the first and second blood vessel, and electroporation is administered between the electrodes through the vasculature of the organ.

A twenty-ninth aspect includes a method of any aspect described herein, wherein a first electrode is inserted into a blood vessel of the organ and a second external grounding pad, plate electrode, or conductive gel external to the organ is used as a second electrode and electroporation is administered between the electrodes through the vasculature of the organ.

Aspects of the invention can comprise electroporation to induce non-thermal irreversible electroporation of target cells. Any aspect of the invention can be adapted to comprise removing cellular debris from the tissue or organ by mechanical perfusion, physiological perfusion, or physical, chemical, or enzymatic techniques, or any combination thereof. Even further, any aspect of the invention can be adapted to further comprise monitoring through electrical measurements to detect and monitor electroporation.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

(FIG. 3A) External Electrodes are charged with either 1500V (top) or set to ground (bottom), and (FIG. 3B) Central venula of each lobule is charged to 1500V while external electrodes are grounded.

FIGS. 6A-C are schematic diagrams of the numerical model used to determine treatment electric field thresholds, with numerical results depicting an electric field of 379±142 V/cm within the treatment margin.

FIGS. 7A-B are graphs showing that lesions that developed after pulses applied at 1 Hz were statistically larger ($\alpha$=0.1) than lesions which developed at rates of 0.25 and 4 Hz.

FIGS. 9A-C are micrographs showing (FIG. 9A) A section of untreated liver after 24 hours of perfusion. Sections of the same liver treated with 90, 1500V/cm, 100 µs pulses at 4 Hz using needle electrodes after 24 hours of perfusion at (FIG. 9B) 10× and (FIG. 9C) 20× magnification.

DETAILED DESCRIPTION OF VARIOUS EMBODIMENTS OF THE INVENTION

Figure 1:
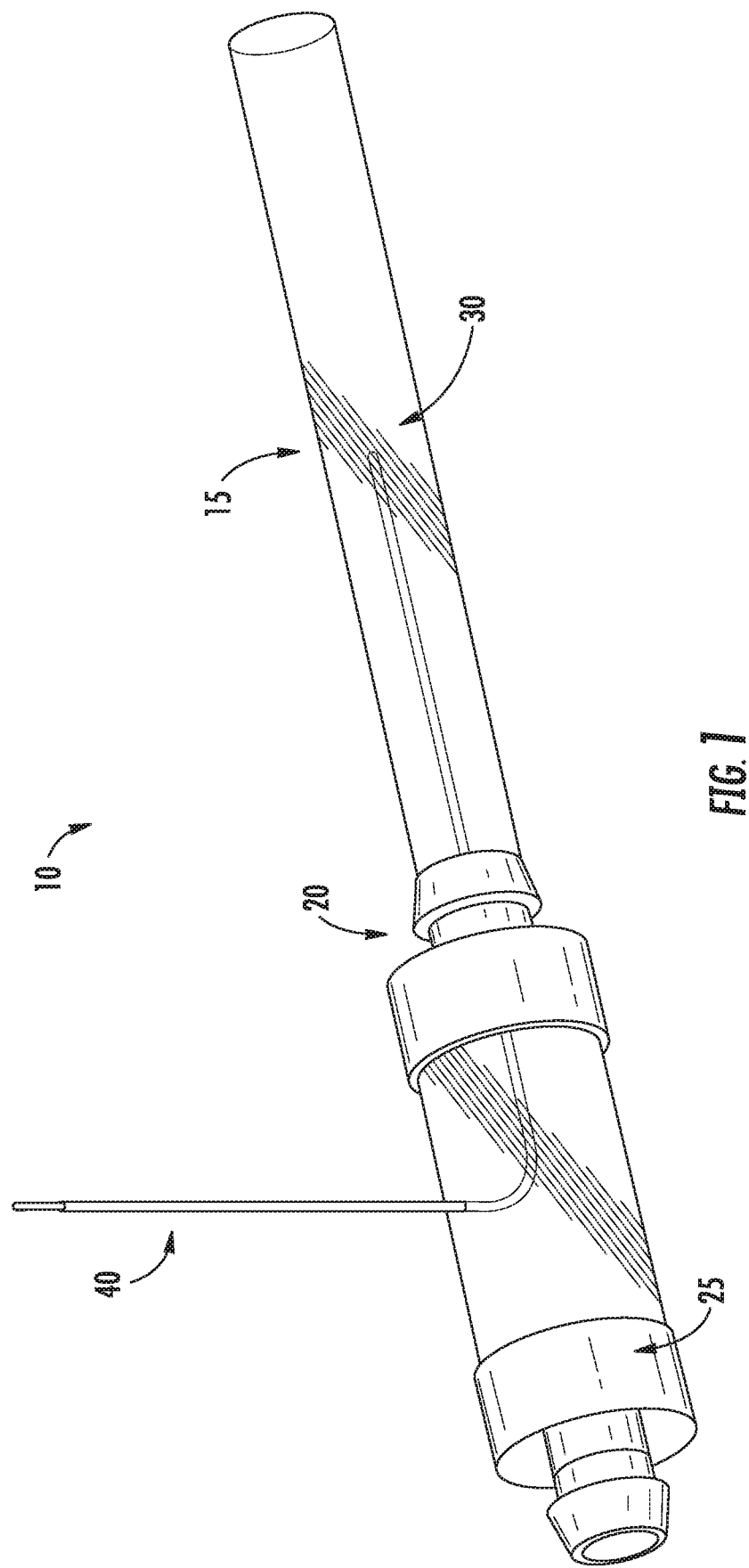
FIG. 1 is a schematic diagram of an embodiment of an IRE-mechanical perfusion connection device according to the invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

According to embodiments of the invention, viable decellularized tissue scaffolds can be attained using non-thermal irreversible electroporation (N-TIRE) on organs under continuous perfusion. Electroporation (reversible and/or irreversible) can be delivered to tissues and organs using any known techniques, including plate electrodes or needle electrodes, or even delivering the electrical charge through the vasculature of an organ or tissue.

More specifically, electroporation can be used as a therapy to treat numerous medical conditions. Irreversible Electroporation, including non-thermal IRE, is a method to kill undesirable cells using electric fields in tissue while preserving the ECM, blood vessels, and nerves. Certain electrical fields, when applied across a cell, have the ability to permeabilize the cell membrane through a process that has come to be called "electroporation." When electrical fields permeabilize the cell membrane temporarily, after which the cells survive, the process is known as "reversible electroporation." Reversible electroporation has become an important tool in biotechnology and medicine. Other electrical fields can cause the cell membrane to become permeabilized, after which the cells die. This deadly process is known as "irreversible electroporation." Non-thermal irreversible electroporation is a new, minimally invasive surgical technique to ablate undesirable tissue, for example, tumor tissue. The technique is easy to apply, can be monitored and controlled, is not affected by local blood flow, and does not require the use of adjuvant drugs. The minimally invasive procedure involves placing needle-like electrodes into or around the targeted area to deliver a series of short and intense electric pulses that induce structural changes in the cell membranes that promote cell death. The voltages are applied in order to electroporate tissue without inducing significant joule heating that would significantly damage major blood vessels and the ECM. For a specific tissue type and set of pulse conditions, the primary parameter determining the volume irreversibly electroporated is the electric field distribution within the tissue. Recent IRE animal experiments have verified the many beneficial effects resulting from this special mode of non-thermal cell ablation, such as preservation of major structures including the extracellular matrix, major blood vessels, and myelin sheaths, no scar formation, as well as its promotion of a beneficial immune response.

Electroporation is a non-linear biophysical process in which the application of pulsed electric fields leads to an increase in permeability of cells, presumably through the creation of nanoscale pores in the lipid bilayer. Weaver, J. C., Electroporation of biological membranes from multicellular to nano scales, *IEEE Trns. Dielectr. Electr. Insul.* 10, 754-768 (2003). If the length and intensity of the pulses do not exceed certain criteria, this permeability is reversible and cellular health and function is maintained. Once a critical electric field intensity threshold is surpassed (approx. 500 to 700V/cm for a typical set of pulse parameters) the cell membrane is unable to recover and cell death is induced. See Garcia, P. et al. Intracranial nonthermal irreversible electroporation: in vivo analysis. *J Membr Biol* 236, 127-136 (2010); Sel, D. et al. Sequential finite element model of tissue electropermeabilization. *Ieee Transactions on Biomedical Engineering* 52, 816-827, doi: 10.1109/tbme.2005.845212 (2005); and Lee, E. W. et al. Advanced Hepatic Ablation Technique for Creating Complete Cell Death: Irreversible Electroporation. *Radiology* 255, 426-433, doi: 10.1148/radiol.10090337 (2010) ("Lee 2010").

The application of pulses that permanently destabilize the membranes of the cells, inducing death in a precise and controllable manner with sub-millimeter resolution (Edd, J. F., Horowitz, L., Davalos, R. V., Mir, L. M. & Rubinsky, B. In vivo results of a new focal tissue ablation technique: Irreversible electroporation. *Ieee Transactions on Biomedical Engineering* 53, 1409-1415, doi: 10.1109/tmbe.2006.873745 (2006)) is a process referred to as non-thermal irreversible electroporation (N-TIRE) (Davalos, R. V., Mir, L. M. & Rubinsky, B. Tissue ablation with irreversible electroporation. *Annals of Biomedical Engineering* 33, 223-231, doi: 10.1007/s10439-005-8981-8 (2005) ("Davalos 2005")). The technique does not rely on thermal mechanisms (Davalos 2005) and has been shown to preserve the structure of the underlying extracellular matrix. Studies show that nerve conduits and bile ducts are not damaged within the ablation zones. Maor, E., Ivorra, A., Leor, J. & Rubinsky, B. The effect of irreversible electroporation on blood vessels. *Technology in Cancer Research & Treatment* 6, 307-312 (2007). Additionally, in vivo liver ablation regions showed minimal damage and minor vasculitis in small vessels. (Lee 2010).

Hypothermic oxygenated perfusion (HOPE), is a method of whole organ preservation which mechanically delivers an oxygenated, nutrient-rich blood substitute to an entire organ at sub-physiological temperatures. See Dutkowski, P., de Rougemont, O. & Clavien. P. A. Machine perfusion for 'Marginal' liver grafts. *Am. J. Transplant.* 8, 917-924, doi: 10.1111/j.1600-6143.2008.02165.x (2008); and Monbaliu. D. & Brassil, J. Machine perfusion of the liver: past, present and future. *Curr. Opin. Organ Transpl.* 15, 160-166, doi: 10.1097/MOT.0b013e328337342b (2010). This method has been successfully demonstrated to improve the preservation quality and transplant success rates of kidneys which have undergone warm ischemia (see Olschewski, P. et al. The influence of storage temperature during machine perfusion on preservation quality of marginal donor livers. *Cryobiology* 60, 337-343, doi: 10.1016/j.cryobiol.2010.03.005 (2010); and Stegemann, J., Hirner. A., Rauen, U. & Minor, T. Use of a New Modified HTK Solution for Machine Preservation of Marginal Liver Grafts. *Journal of Surgical Research* 160, 155-162, doi::10.1016/j.jss.2008.10.021 (2010)) with research striving to reach 72 hour preservation times (Yamamoto, N. et al. 72-Hour Preservation of Porcine Liver by Continuous Hypothermic Perfusion with UW Solution in Comparison with Simple Cold Storage, *Journal of Surgical Research* 51, 288-292 (1991). Schon et al. and Brockmann et al. have demonstrated the ability to prolong organ quality using normothermic perfusion, a process in which the perfused fluid is held at or near physiological temperatures. See Schon, M. R. et al. Liver transplantation after organ preservation with normothermic extracorporeal perfusion. *Annals of Surgery* 233, 114-123 (2001); and Brockmann, J. et al. Normothermic Perfusion A New Paradigm for Organ Preservation. *Annals of Surgery* 250, 1-6, doi: 10.1097/SLA.0b013e3181a63c10 (2009).

These methods of organ preservation can be used to isolate N-TIRE tissue ablation effects from the immune response observed in vivo and the natural degradation of tissue post mortem. Recently, it has been determined through the use of translational laboratory models that capitalizing on the ability of N-TIRE to destroy cells without destroying the extracellular matrix (Davalos, R. V. Irreversible Electroporation to Create Tissue Scaffolds. United States patent (2009); and Phillips, M., Maor, E. & Rubinsky, B. Non-Thermal Irreversible Electroporation for Tissue Decellularization. *J. Biomech. Eng*, doi: 10.1115/1.4001882 (2010)) renders N-TIRE a viable means for scaffold creation by way of organ decellularization.

N-TIRE treatment outcomes can be predicted through numerical modeling tissue ablation/decellularization, which is clinically relevant and could be widely applied for tissue engineering. See Davalos, R. V. & Rubinsky. B. Temperature considerations during irreversible electroporation. *International Journal of Heat and Mass Transfer* 51, 5617-5622, doi: 10.1016/j.ijheatmasstransfer.2008.04.046 (2008); Edd, J. F. & Davalos, R. V. Mathematical Modeling of irreversible Electroporation for treatment planning. *Technology in Cancer Research & Treatment* 6, 275-286 (2007); and Neal. R. E., II & Davalos, R. V., The Feasibility of Irreversible Electroporation for the Treatment of Breast Cancer and Other Heterogeneous Systems. *Annals of Biomedical Engineering* 37, doi::10.1007/s10439-009-9796-9 (2009).

Engineered scaffolds could then be reseeded with a recipient's cells, resulting in a functional organ construct. Such methods of organ regeneration might be used to decrease the shortage in supply of organs for transplant.

Embodiments of the present invention relate to methods, systems, and devices for the delivery of Irreversible Electroporation (IRE) through the vasculature of organs. IRE administered in this manner whether ex vivo or in vive can be used to treat tumors embedded deep within vascularized organs. Applications of embodiments of the invention also include use of IRE through the vasculature of tissues and organs to decellularize organs and produce a scaffold from existing tissue with the extracellular matrix intact and cellular debris removed.

Generally, ablation procedures involve delivering a series of low energy (intense but short) electric pulses to the targeted tissue. These pulses irrecoverably destabilize the cell membranes of the targeted tissue, thereby killing the cells affected by the electrical field. The treatment is non-thermal, essentially only affects the cell membranes of the targeted tissue, and does not affect the nerves or blood vessels within the treated tissue.

The present invention provides decellularized scaffolds, which can be created using non-thermal irreversible electroporation (IRE). The organ or tissue can be perfused during and/or after the procedure, which is a routine technique in the medical arts.

Following preparation of a scaffold, tissue engineering can involve ex vivo seeding and attachment of human cells onto a scaffold. To date, the most successful scaffolds for tissue engineering have been natural and made by chemically and/or mechanically decellularizing organs of large animals (e.g., pigs).

Embodiments of the invention provide methods of making a decellularized tissue scaffold. In general, tissue comprising cells and an underlying scaffold can be treated in vivo or ex vivo with an electrical field of sufficient power and duration to kill cells of the tissue. The electrical field is administered directly into the vasculature of the organ. The electrical field is guided through the vasculature of the organ by the walls of the vascular system. Preferably, the electrical pulses are administered in a manner to avoid disruption to the underlying scaffold and vasculature of the organ or tissue.

The methods are suitable for producing a tissue scaffold for use in tissue engineering. Although the source of the tissue is not limited, in exemplary embodiments, the tissue is from a relatively large animal or an animal recognized as having a similar anatomy (with regard to the tissue of interest) as a human, such as a pig, a cow, a horse, a monkey, or an ape. In embodiments, the source of the tissue is human, use of which can reduce the possibility of rejection of engineered tissues based on the scaffold.

In preferred embodiments, the method leaves intact vascular structures of the tissue, such as capillaries. In embodiments, the method leaves intact neural tubes present in the tissue before treatment with the electrical field. As used herein, the term "intact" refers to a state of being whereby an element is capable of performing its original function to a substantial extent. Thus, for example, an intact capillary is a capillary that is capable of carrying blood and an intact neural tube is a tube that can accommodate a neuron. In embodiments, cells of the vascular system and neural system remain intact, as well as other glandular structures, including examples such as bile or lactiferous ducts. In such embodiments, the cells can remain as part of the scaffold and engineered tissue, or may be removed by suitable treatment techniques or by cells that are seeded onto a scaffold or by cells of a body that receives the engineered tissue.

According to method embodiments of the invention, a tissue is exposed to an electrical field that is adequate in time and power to cause killing of cells of the tissue, but not adequate to significantly destroy the scaffolding upon and within which the cells exist. Furthermore, in preferred embodiments the electrical field does not cause irreversible tissue damage as a result of heating of the tissue. Various ways of providing such an electrical field are possible. In typical embodiments, one or more electrical pulses are applied to the tissue to cause cell membrane disruption as a result of the electricity and not substantially as a result of heat. Where two or more pulses are used, the pulses are separated by a period of time that allows, among other things, the tissue to cool so that thermal damage does not occur to a significant extent. For example, one or more electrical pulses can be applied to the tissue of interest for a duration in a range from about 5 microseconds ($\mu$s) to about 200 seconds and pulses may be applied at lower repetition rates over periods of 1 to 24 hours. For convenience, a short period of treatment might be desired. As such, in preferred embodiments, electrical pulses are applied for a period of about 1-10000 $\mu$s. Further, although there is no limit on the number of pulses to be delivered to the tissues, in preferred embodiments, from about 1 to about 100 pulses are applied to the tissue. For example, in an exemplary embodiment, about 10-1000 pulses of about 100 $\mu$s each in duration are applied to the tissue to cause cellular ablation.

Organs can then be treated to create a decellularized scaffold by adjusting perfusion parameters to remove cellular debris. Mechanical cleansing of cellular debris can be performed for any amount of time necessary to achieve the desired results of removal of the debris, for example, over periods of 4, 12, 24, 48, or 72 hours. Perfusion parameters including systolic pressure, diastolic pressure, and temperature can be manipulated to improve the efficiency of removal of cellular debris. Further, mild detergents may be added if necessary to enhance or facilitate removal of the cellular debris. Preferred embodiments provide for perfusion protocols which result in the removal of 99% of cellular debris and DNA constituents.

Embodiments of the invention provide methods wherein the application of varying amounts of energy (both reversible and irreversible electroporation) can be modulated to produce a wide range of desirable tissue ablation effects, including selective removal of normal and neoplastic cells.

According to the invention, the effects of energy application can be controlled and manipulated by varying numerous parameters including, e.g.: the voltage, amperage, duration, and frequency of the energy; the design and positioning of the energizing system; the design and use of sophisticated, precision-controlled vascular perfusion systems; the physiology-emulating characteristics of sophisticated, precision-controlled vascular perfusion systems; the conditions of perfusion and preservation of ex vivo organs and tissues; the conditions of perfusion and preservation of in vivo organs and tissues; and/or the composition of intravascular fluids that function partially or wholly as extensions of the energy application system and protocols.

In this effort, there are several parameters that can be monitored and adjusted in using non-thermal IRE for preparation of tissue scaffolds, or for treating tumors in vivo or ex vivo, or for ensuring adequate macromolecule biotransport in diseased or otherwise targeted tissues. For example, embodiments of the invention can be used in gene therapy for islets of pancreas in Type I diabetics to spur production of insulin, i.e., a situation where there is non-cancerous diseased tissue. The invention can also be applicable to immunomodulation by introducing genes into tissue such as muscle to produce desired antibodies, i.e., healthy tissue used as vessel for therapy. Parameters that can be varied for particular applications include voltage gradient. In embodiments, the pulses produce a voltage gradient in a range of from about 10 volt/cm to about 10,000 volt/cm. Voltage gradient (electric field) is a function of the distance between electrodes and electrode geometry, which will vary depending on the size of the tissue sample, tissue properties, and other factors. In some embodiments, two electrodes are used, and they are placed about 5 mm to 10 cm apart. Typical electrode diameters range from 0.25-1.5 mm and typically 2 or 4 electrodes are used. In embodiments, one bipolar electrode is used. Also, the "electrode" can have parts of it insulating (including using a non-conductive sheath) and parts of it conductive (e.g., at the tip) to ensure proper application of the electrical current and to minimize production of excessive heat in parts of the tissue.

Appropriate electrical fields and durations of exposure are those that have been reported in the literature as being suitable for medical treatment of tissues for tumor ablation. Exemplary exposure parameters include: ninety 90 microsecond (μs) pulses at 1.5 kV/cm at a frequency of 1 Hz or 4 Hz; eighty 100 μs pulses at 2.5 kV/cm at a frequency of 1 Hz or 4 Hz; one 20 millisecond pulse at 400V/cm; ten 100 μs pulses at 3800 V/cm at a frequency of 10 pulses per second; ninety 100 μs pulses ranging from 1000 to 1667 V/cm at a frequency of about 1 Hz or 4 Hz; and eighty pulses of 100 μs ranging from 1000 to 3000 V/cm at about 1 Hz or 4 Hz. In general, the frequency of pulsing can be as low as half the pulse width and can be quite a bit farther apart. Any suitable frequency that allows for electroporation without significant thermal damage to the tissue is acceptable. Electrical current can be supplied as either DC or AC. Indeed, it is within the skill of the art to adjust these parameters as applicable to achieve a particular desired result. Any number of pulses can be administered, for example, from 1-1000. The pulses can have a duration of any amount of time, such as from 1 microsecond to 1 second. The voltage can be any amount to achieve reversible or irreversible electroporation depending on the desired effect and can include for example from 500V/cm to 5000 V/cm. e.g., 1500 V/cm. Indeed, to achieve IRE at the capillary bed, much less voltage is required, e.g., on the order of about 1 V/cm up to about 1000 V/cm.

The shape and size of the electrodes are not critical to practice of the invention. Those of skill in the art may choose any shape and size that is suitable for transmitting the desired electrical field into the tissue. For example, the electrodes may be plate type, wire type, or needle type and may be circular in shape, ovoid, square, rectangular, diamond-shaped, hexagonal, octagonal, etc. For wire type electrodes, a diameter smaller than the vasculature in which the wire is to be inserted is desired, such that the electrode does not occlude vasculature. In some designs and manifestations, it may be desirable to use electrodes that are part of an occlusive device providing isolation of a portion of the circulation of an organ or tissue. Likewise, the surface area of the electrodes is not critical to practice of the invention. Thus, for example, the surface area may be about 0.5 square centimeter, about 1 square centimeter, or greater. For electrodes inserted directly into the vasculature of an organ or tissue, preferably the electrodes are elongated wire type electrodes of a sufficient length to provide the electrode a sufficient distance within the vasculature. The diameter of the wire type electrode can also be adapted for insertion into various types of organ vasculature such that the electrode preferably avoids contact or has minimal contact with the interior walls of the vasculature. In some embodiments, there is at least some separation between the electrodes and the walls of the vasculature. In the wire type electrode, it is possible to temporarily occlude the vessels "upstream" and "downstream" of the targeted region to reduce the potential for electrical current and associated energy losses traveling beyond the bounds of the targeted region between the electrodes. Such an embodiment performed in vivo should deliver the pulses within a time period that will not induce unacceptable ischemic effects to the targeted and any "downstream" regions. More particularly, such techniques can include clamping the vessels above and below the targeted organ or tissue so that the rest of the vessels do not conduct the current (as clamping with the insulating vessel walls should "open" the circuit). This is more relevant for gene or drug delivery applications, where killing cells is not the goal, and there should be a suitable window to perform this without damaging the tissue. Such methods of the invention can be employed, for example, for plaque removal, e.g., occlude the carotid artery for about 10 minutes while removing plaque therefrom.

Exposing tissue to electrical fields in some circumstances generates heat. To ensure that tissue damage due to heat is avoided, the amount of energy transmitted to the tissue is set below a threshold level per unit time. Time and temperature parameters are known in the art for IRE, and any suitable combination may be used. For example, the temperature of the tissue can be monitored during treatment for ablation, and the electrical pulses adjusted to maintain the temperature at 100° C. or less, such as 60° C. or less, or at body temperature. In embodiments, the temperature can be maintained at a physiological temperature normal to a particular organ or subject. In some embodiments, the temperature is maintained at 50° C. or less.

In some embodiments, the method includes adjusting the applied voltage, length of the pulses, and/or number of pulses to obtain irreversible electroporation averaged over the biological cells of the tissue, thereby achieving irreversible electroporation of the biological cells in the tissue at a level that minimizes damage to non-target tissue. Protocols may include the same or varied parameters throughout administration of the electrical charge. Likewise, in some embodiments, the duration of the applied voltage is adjusted in accordance with the current-to-voltage ratio to achieve irreversible electroporation of identified tissue cells, whereby cell membranes are disrupted in a manner resulting in cell death. Additional exemplary parameters are disclosed below.

Example I—Multiphysics Modeling

Preliminary multiphysics modeling was conducted to establish the feasibility of using the vascular system as a pathway for electrical pulse delivery. The electric field distribution, which is the key factor for the development of pores (reversible or irreversible) in the cell membrane, was modeled using a finite element method. Three liver tissue models were developed representing the liver structure with different levels of detail. The Comsol Multiphysics was used to solve for the electric potential ($\phi$) which obeys the Laplace Equation:

$$\Lambda \cdot (\sigma \Lambda \phi) = 0$$

where $\sigma$ is the electrical conductivity.

Figure 2:
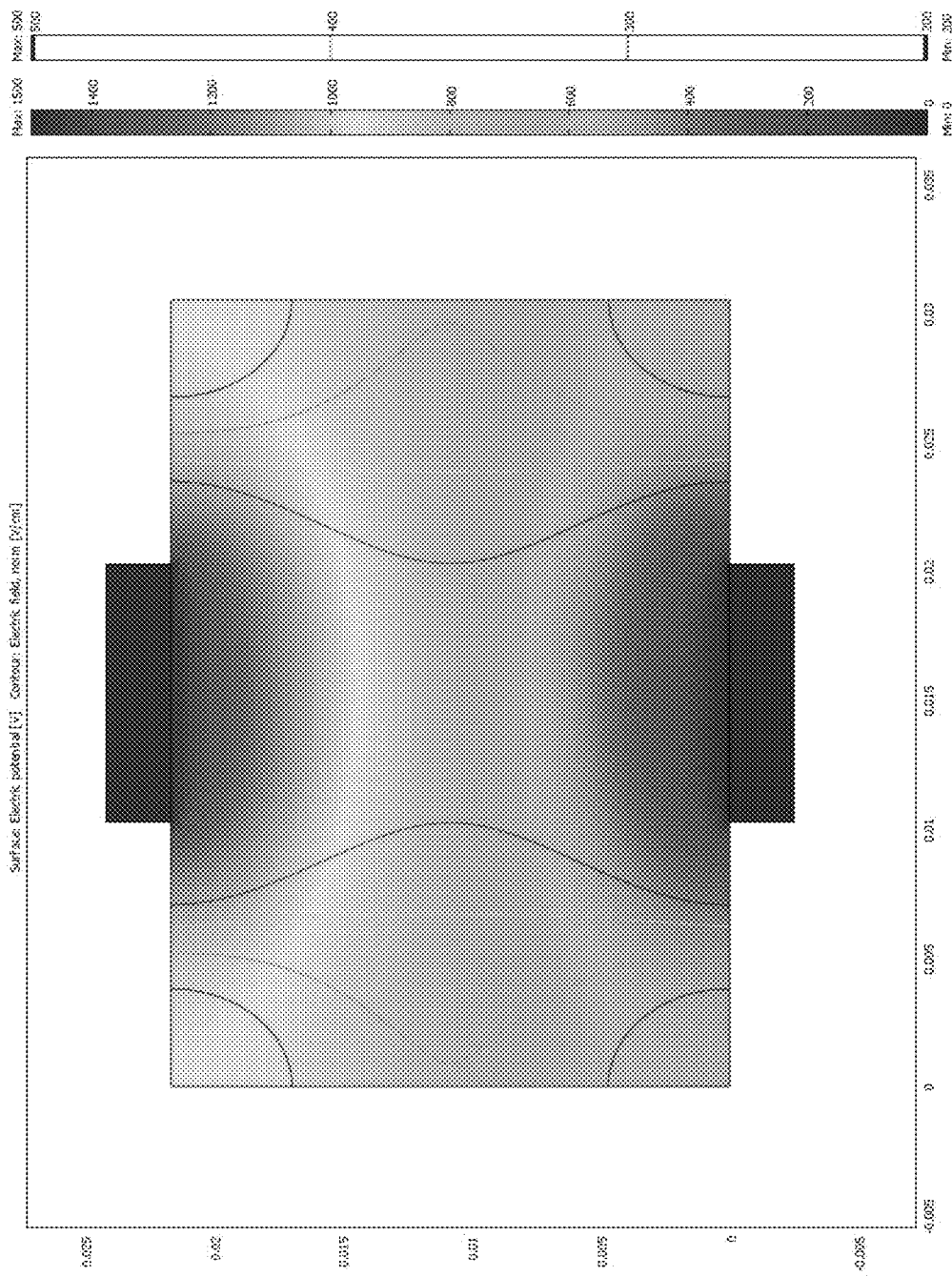
FIG. 2 is a graph showing electric potential and electric field contours developed in a numerical representation of previous experiments.

Model 1:

Initially, the liver was modeled as a 2 cm thick homogenous structure with 1 cm diameter plate electrodes on either side of the tissue. This model was used to correlate experimental lesions to electric field intensities. A single 10 microsecond 1500V/cm pulse was delivered to the top electrode while the bottom electrode was grounded. As shown in FIG. 2, the results of this model show that for the electrical parameters used, simulated electric field strength of approximately 400V/cm is required to generate a lesion of similar width to experimental results.

TABLE 1

Electrical conductivity values for elements used in all models.

| Element | Conductivity (S/m) |
| --- | --- |
| Liver | 4.10E−01 |
| Connective tissue | 4.10E−02 |

TABLE 1-continued

Electrical conductivity values for elements used in all models.

| Element | Conductivity (S/m) |
|---|---|
| Perfusate | 1.40E+00 |
| External Electrodes | 5.998E+07 |

Model 2:

The liver is a complex organ populated by numerous sets of vasculature branches, lymph and bile ducts. Branches of the hepatic portal vein and hepatic artery deliver blood to basic functional units, lobules which are structurally functioned to filter blood, remove bacteria, and produce bile. Blood driven through the lobules eventually reach a large central venula which drain into the hepatic vein and return blood to the circulatory system. While under perfusion, a perfusate replaces blood as the fluid traveling through the vasculature. It is noted, however, that bile production has been observed to continue for up to 24 hours. A second multi-scale model was produced to understand how the complex vasculature affects the electric field distribution when two different modalities of voltage application are used. The first modality used traditional electrodes placed outside of the tissue, while the second used the central venula as the voltage source and external electrodes as grounds. Each lobule was modeled as a hexagon with an equivalent radius of 1 mm surrounded by a 5 micron connective tissue layer and a 200 micron diameter central venula which is consistent with swine histology. A single 10 microsecond 1500V/cm pulse was again simulated.

Figures 3A, 3B:
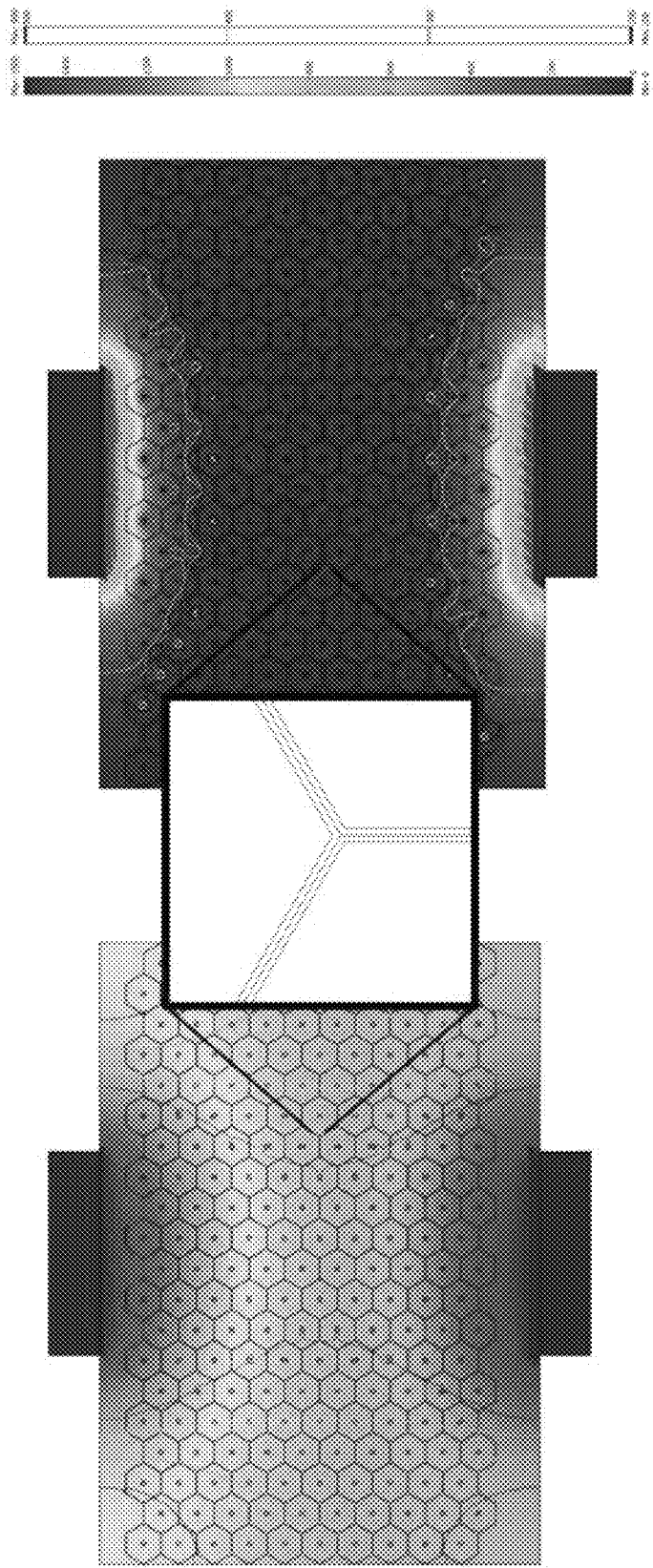
FIGS. 3A-B are graphs showing numerical results of two different simulations with lobule level details (Model 2) where.

The electric field distribution within the tissue did not vary significantly with the additional inhomogeneity caused by the lobule epithelial layers when external electrodes are used. The most significant alterations occurred in proximity to the more highly conductive central venula. When the central venula of each lobule is charged to 1500V, a significantly different electric field distribution is formed. Regions of tissue which reach a high enough electric field to become irreversibly electroporated extend only approximately 0.5 cm into the tissue. Though this modality of electric field application is not sufficient for total decellularization, it may be an effective means by which tumors close to the surface of highly vascularized organs may be treated. The model presented in FIG. 3A shows the external electrodes charged with either 1500V (top) or set to ground (bottom), which demonstrated that the electric field distribution using this modality did not significantly change with the added inhomogeneity. The model presented in FIG. 3B shows the central venula of each lobule charged to 1500V while external electrodes are grounded. It is noted that the models presented in FIGS. 3A-B are not completely physiologically exact as fluid readily flows from the portal arterioles and venules through the lobule into the central venula.

Model 3:

Model 3 incorporates the portal arterioles, portal venules, and bile ducts at the vertices of a single lobule. The central vein is surrounded by bulk liver tissue. The magnitude of the applied 10 microsecond pulse was varied until an electric field distribution, in the range of that seen in bulk liver tissue, developed.

Figure 4A:
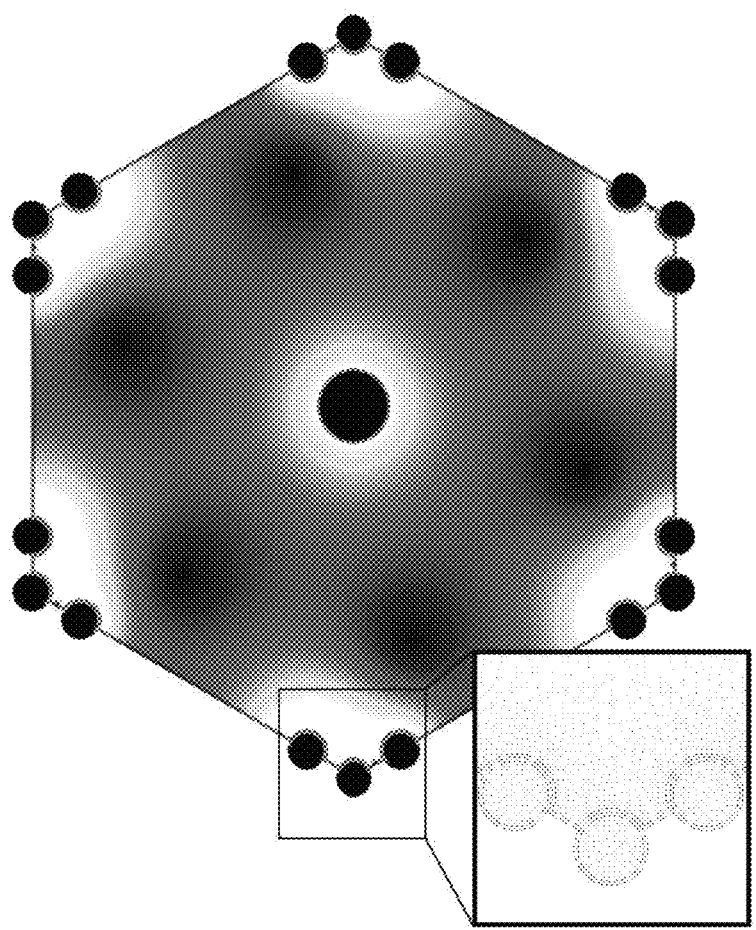
FIG. 4A is a diagram showing simulated electric field distribution with a single lobule when a 50V 100 microsecond pulse is administered to the bile duct and the central venule, portal venule and portal arteriole are grounded.
Figure 4B:
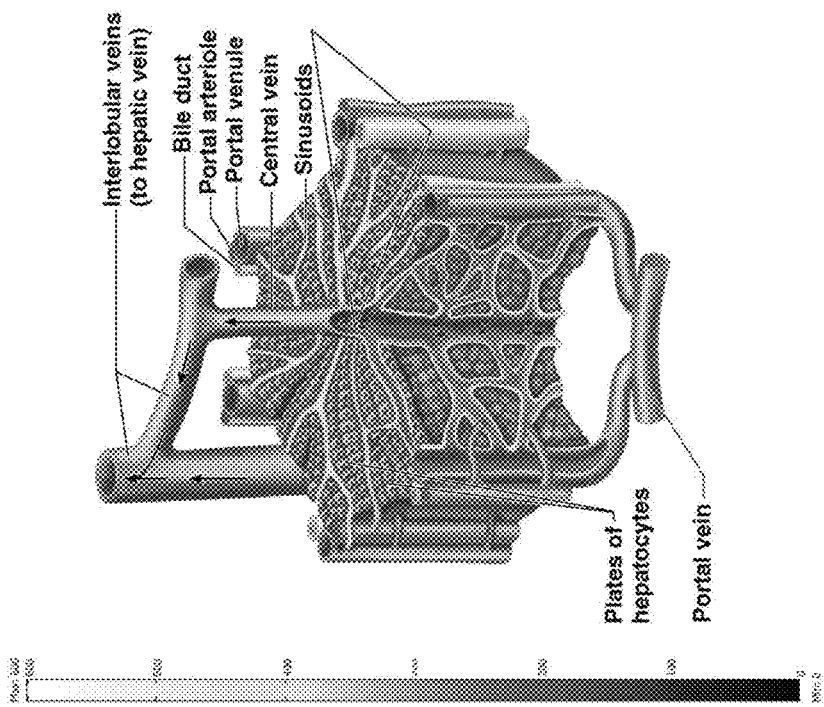
FIG. 4B is a schematic representation of a liver lobule illustrating the complex vascular network of these functional units (see Slieman, T. A. The Digestive System, http://tonyslieman.com/phgy_230_lecture_digestive.htm).

Results from this simulation are shown in FIG. 4A. The results from this simulation show that the development of an IRE inducing electric field within a single lobule is feasible using the organ's vasculature. Additionally, it was found that a 50V pulse is significant enough to raise the electric field to IRE inducing levels. This is far below the 1500V pulse necessary to induce IRE when the electric field is applied across the entire tissue construct. It can be seen from FIG. 4B and histological samples that there is a complex microvasculature network which connects the portal arterioles and venules from the central vein. Between the vasculature there are hepatocytes which secrete bile into the bile ducts. Models 1 and 2 assume that these microvasculature networks present a significant resistance to the flow of current and the internal constituents of the lobule can be modeled as a heterogeneous tissue. This is a reasonable assumption to make where vascular occlusion may occur if erythrocytes (in vivo) or epithelial cells are damaged by the electric field.

TABLE 2

Resistance of vessels of decreasing diameter with a 10:1 length to diameter ratio and a fluid conductivity of 1.4 S/m.

| Diameter (m) | Area (m$^2$) | Length (m) | Resistance (ohms) |
|---|---|---|---|
| 1.0E−02 | 7.85E−05 | 1.0E−01 | 9.09E+02 |
| 1.0E−03 | 7.85E−07 | 1.0E−02 | 9.09E+03 |
| 1.0E−04 | 7.85E−09 | 1.0E−03 | 9.09E+04 |
| 1.0E−05 | 7.85E−11 | 1.0E−04 | 9.09E+05 |

An approximation of the resistance (R) of vasculature and microvasculature can be easily achieved if the fluid conductivity (ρ) is known by solving the constitutive relation:

$$R = \frac{\rho L}{A}$$

where L and A are the length of the vessel and the vessel's cross sectional area respectively. The results presented in Table 2 show that the resistance of a 10 μm diameter vessel 100 μm long can be as high as 90 kΩ when the vessel is filled with phosphate buffered solution. While significant, this resistance is not high enough to prevent current flow through microvasculature. Additionally, the immense number of microvessels which are connected in parallel throughout the organ should drastically reduce the overall electrical resistance.

One embodiment of the invention is the preparation of scaffolds by administering IRE during active perfusion of the organ or tissue. Electrodes can be placed into or near the vicinity of the tissue with the application of electrical pulses causing irreversible (or reversible) electroporation of the cells through the target region. One way to administer the electrical pulses is through the vasculature of the organ itself. Placement of the electrodes defines the treated region; thus, the treated region may be only a portion of an entire tissue or organ that is used as the starting material. The electric pulses irreversibly or reversibly permeate the membranes of treated cells, thereby invoking cell death (if irreversible). The length of time of the electrical pulses, the voltage applied, and the resulting membrane permeability are all controlled within defined ranges. Application of electric pulses that result in cell death can still preserve some or all of the vascular structures of the organ, preferably including those involved in microcirculation and macrocirculation. In some embodiments, microcirculation structures may be partially or totally damaged, but larger structures maintained.

For in vitro and ex vivo practice of embodiments of the invention, secondary techniques for removing cellular material can be used. For example, any of the known physical, chemical, or enzymatic techniques can be used to remove cellular debris from the irreversibly permeabilized cells. Likewise, the treated tissue can be attached to an artificial perfusion system, which can pump a liquid composition (e.g., a detergent-containing aqueous composition) through the treated tissue, resulting in removal of cell debris from the scaffold. Importantly, such secondary treatments, where applied, can be applied under relatively gentle conditions, which allow for removal of cellular debris but also retention of the scaffolding structure (including vascular and neural structures). The use of non-thermal IRE allows for such gentle procedures, and improves the scaffold that is ultimately produced, as compared to procedures not relying on non-thermal IRE.

For in vivo practice of the method, the debris remaining from the irreversibly permeabilized cells may be left in situ and may be removed by natural processes, such as the body's own circulation and immune system.

The concept of irreversible electroporation to decellularize tissues is different from other forms decellularization used in the art. Irreversible electroporation is different from chemical and physical methods or cell lysis using osmotic imbalance because it uses electricity to kill the cells. Irreversible electroporation is a more benign method because it destroys only the cell membrane of cells in the targeted tissue and does not damage to the underlying extracellular matrix (ECM). In contrast, chemical and physical methods can damage vital structures, such as the ECM, blood vessels, and nerves. IRE of the type described here, uses electrical pulses to serve as the active means for inducing cell death by a specific means. i.e., by fatally disrupting the cell membrane.

Irreversible electroporation may be used for the decellularizing tissue in a minimally invasive procedure that does not or does not substantially affect the ECM. Its non-selective mode of decellularization is acceptable in the field of tissue engineering and provides results that in some ways are comparable to sonication, inducing an osmotic imbalance, freezing, or chemical decellularization.

One exemplary embodiment of the invention includes a method whereby cells of tissue are irreversibly electroporated by applying pulses of very precisely determined length and voltage during active perfusion of the organ or tissue. This may be done while measuring and/or observing changes in electrical impedance in real time and noting decreases at the onset of electroporation and adjusting the current in real time to obtain irreversible cellular damage without thermal damage. The method thus may include use of a computing device and sensors to monitor the effects of the electrical treatment. In embodiments where voltage is applied, the monitoring of the impedance affords the user knowledge of the presence or absence of pores. This measurement shows the progress of the pore formation and indicates whether irreversible pore formation, leading to cell death, has occurred.

Yet another embodiment includes a method whereby the onset and extent of electroporation of cells in tissue can be correlated to changes in the electrical impedance (which term is used herein to mean the voltage over current) of the tissue. At a given point, the electroporation becomes irreversible. A decrease in the resistivity of a group of biological cells occurs when membranes of the cells become permeable due to pore formation. By monitoring the impedance of the biological cells in a tissue, one can detect the average point in time in which pore formation of the cells occurs, as well as the relative degree of cell membrane permeability due to the pore formation. By gradually increasing voltage and testing cells in a given tissue, one can determine a point where irreversible electroporation occurs. This information can then be used to establish that the cells of the tissue have undergone irreversible electroporation. This information can also be used to control the electroporation process by governing the selection of the voltage magnitude. Other imaging techniques can be employed to monitor how much area has been treated (e.g., ultrasound, MRI, CT, etc.).

The invention provides the simultaneous irreversible electroporation of multitudes of cells providing a direct indication of the actual occurrence of electroporation and an indication of the degree of electroporation averaged over the multitude. The discovery is likewise useful in the irreversible electroporation of biological tissue (masses of biological cells with contiguous membranes) for the same reasons. The benefits of this process include a high level of control over the beginning point of irreversible electroporation.

One feature of embodiments of the invention is that the magnitude of electrical current during electroporation of the tissue becomes dependent on the degree of electroporation so that current and pulse length are adjusted within a range predetermined to obtain irreversible electroporation of targeted cells of the tissue while minimizing cellular damage to surrounding cells and tissue. Yet another feature of embodiments of the invention is that pulse length and current are precisely adjusted within ranges to provide more than mere intracellular electro-manipulation which results in cell death and less than that which would cause thermal damages to the surrounding tissues. Another feature of embodiments is that measuring current (in real time) through a circuit gives a measurement of the average overall degree of electroporation that the cells in the tissue achieve.

Yet other features of embodiments include that the precise electrical resistance of the tissue can be calculated from cross-time voltage measurement with probe electrodes and cross-current measurement with the circuit attached to electroporation electrodes; the precise electrical resistance of the tissue is calculated from cross-time voltage measurement with probe electrodes and cross-current measurement with the circuit attached to electroporation electrodes; and electrical measurements of the tissue can be used to map the electroporation distribution of the tissue. It is noted that, in irreversible electroporation it is possible and perhaps even preferred to perform the current or EIT measurements a substantial time (several minutes or more) after the electroporation to verify that it is indeed irreversible.

In embodiments of the method, it is preferred to remove cellular debris from the decellularized scaffolding after primary cell destruction with non-thermal IRE. In such embodiments, any known technique for doing so may be used, including any of the known physical, chemical, and/or enzymatic methods. In one exemplary embodiment, removal of cellular material is accomplished, at least in part, through perfusion of the tissue scaffolding with an appropriate agent (e.g., water, pH-adjusted water, an aqueous solution of one or more chelating agents, etc.), using general diffusion, transmittal via remaining intact vasculature, or a mixture of the two.

For in vitro methods, it is preferred that the scaffold be sterilized, especially where the scaffold is to be used to prepare engineered tissues and organs for implantation into a host. Sterilization and/or removal of debris after decellularization is usually conducted for scaffolds that will be used as implants to reduce the risk of patient rejection (for example, due to DNA fragments). When a scaffold requires some type of sterilization, methods published in the literature for sterilization of scaffolds can be employed.

For in vitro methods, the method of making a decellularized tissue scaffold results in a decellularized tissue scaffold that is isolated from its natural environment. For in vivo methods, the method of making a decellularized tissue scaffold results in a tissue scaffold that is devoid of normal cellular material. Thus, in an aspect of the invention, an engineered tissue scaffold is provided. The engineered tissue scaffold comprises a natural scaffold that is removed from its natural environment and/or from which cellular material has been removed. The engineered tissue scaffold of the invention contains at least some, preferably most, and more preferably substantially all or all, of the vascular structures (i.e., arteries, veins, capillaries) and conducting structures (i.e., ducts) present in the tissue in its natural state. In embodiments, the tissue scaffold comprises at least some, preferably most, and more preferably substantially all or all of the neural structures present in the tissue in its natural state. In embodiments, the scaffold further comprises the cells that constitute these vascular structures and/or these neural structures. Preferably, the engineered tissue scaffold contains a reduced number of the cells naturally populating the scaffold. A majority of the original cells, more preferably substantially all of the original cells, and most preferably all of the original cells, are absent from the engineered scaffold. In embodiments, the remaining cells are cells that comprise vascular or neural structures. In preferred embodiments, some, most, or all of the cellular debris from the cells is absent from the engineered scaffold. Likewise, in embodiments, the tissue scaffold contains some or all of the neurons originally present in the tissue. However, in embodiments, the neurons are destroyed but the neural tubes in which the neurons existed remain intact.

In some embodiments, the engineered scaffold comprises cell debris from cells originally (i.e., naturally) populating the scaffold. As discussed above, in such embodiments, the cell debris can be removed using known means. Alternatively, some or all of the cell debris may be left in and on the scaffold. In embodiments where cell debris is left on the scaffold, it can be later removed by the action of new cells seeded onto the scaffold and/or during the process of seeding, infiltration, and growth of new cells. For example, where new cells are seeded onto a scaffold comprising cell debris, the action of the new cells infiltrating and growing, alone or in combination with a perfusion means for feeding and supporting the new cells, can result in removal of the cell debris.

The present invention provides engineered tissue scaffolds that comprise vascular structures that can function in providing nutrients and gases to cells growing on and in the scaffolds. The use of non-thermal IRE to create the engineered scaffolds permits retention of these important structures, and thus provides for improved scaffolds for use in medical, veterinary, and research activities. The invention thus provides engineered scaffolds capable of having relatively large dimensions. That is, because re-seeded cells growing within the inventive scaffolds need not be close (i.e., within 1 mm) to an external surface in order to obtain nutrients and gas, the engineered scaffolds may be thicker than scaffolds previously known in the art. Engineered scaffolds may have thicknesses of any desirable range, the only limitation being the ability to generate the appropriate electrical field to cause decellularization. However, such a limitation is not a significant physical constraint, as placement of electrodes to affect IRE is easily adjusted and manipulated according to the desires of the practitioners of the invention.

Engineered scaffolds of the invention can have thicknesses that approach or mimic the thicknesses of the tissues and organs from which they are derived. Exemplary thicknesses range from relatively thin (i.e., 1 mm or less) to moderately thick (i.e., about 5 mm to 1 cm) to relatively thick (i.e., 5 cm or more, such as 10-20 cm or more).

Examples of providing engineered scaffolds from IRE of tissues during active perfusion according to methods of the invention are provided below. Ideally IRE performed ex vivo should be done as the tissue is perfused in a bioreactor. Perfusion of tissue in a bioreactor has been published in the literature, and the parameters disclosed therein can be generally applied within the present context. IRE is a special mode for cell ablation perfectly suitable to creating scaffolds because it kills the cells in the targeted area while sparing major blood vessels, connective tissue, nerves, and the surrounding tissue. Typically, mild enzymes or chemicals (non-ionic detergents, zwitterionic detergents, chelating agents, enzymatic methods) can be used to facilitate removal of DNA fragments after decellularization (for IRE in vivo, the removal of cells can be accomplished by the body's natural system).

One approach to implementing IRE ex vivo with a bioreactor perfusion system includes: (a) attaching a freshly excised organ to a bioreactor perfusion system to maintain physiological environment or under other temperature conditions to achieve a particular result; (b) inserting electrodes into targeted area, such as within the vasculature of the organ; (c) subjecting the organ to perfusion with saline or another appropriate perfusate; and (d) administering electrical pulses through one or more electrode to administer reversible or irreversible electroporation through the vasculature. Once undesired cells are ablated, the cellular debris can be removed using chemical (e.g., non-ionic detergent) or physical techniques to remove cellular content/debris (especially if ex vivo). The scaffold can then be seeded with seed cells into the targeted/treated area. Additional perfusion of the organ can be performed to administer nutrients and/or growth media to the seeded cells (demonstration of perfusion during IRE in Edd et al., 2006) and the bioreactor perfusion system can be maintained at optimal conditions for cell growth (37° C.). Any one or more of these method steps can be performed and in any order to achieve a desired volume of treated tissue. For example, to treat several areas of an organ or to treat the entire organ, electroporation can be repeated over several smaller areas of the organ and intermittent with substantial resting periods where perfusion is allowed to flush cell debris from the organ, or a substantial period of perfusion without IRE can be allowed to take place after IRE is performed. Likewise, if using plate or needle type electrodes, perfusion can be allowed to take place prior to placement of or insertion of the electrodes, whereas with wire type electrodes placed within the vasculature, it may be desired to place the electrodes appropriately then begin the active perfusion. Indeed, any one or more these steps can be omitted, modified, rearranged with other steps, or substituted for other steps as appropriate.

Example II—IRE During Active Perfusion

Young mixed breed pigs were sacrificed by way of barbiturate overdose. Livers were harvested and placed on ice within 15 minutes of death. Vascular anastomosis with the perfusion system was created by inserting Luer lock syringe connections into the portal vein, hepatic artery, and major hepatic vein, which were then secured with zip ties.

The livers were flushed with lactated Ringer's solution (LRS) to remove blood/clots before placement on the perfusion system.

The VasoWave™ Perfusion System (Smart Perfusion, Denver, N.C.) was used to perfuse the livers for 4 and 24 hours. This system produces a cardioemulating pulse wave to generate physiological systolic and diastolic pressures and flow rates within the organ. The system is capable of controlling the oxygen content of the perfusate above and below physiological norms. A perfusate, consisting of modified LRS, was delivered to the portal vein and hepatic artery and recycled back into the system through the hepatic vein. All livers were under active machine perfusion within one hour post-mortem.

While under perfusion, the ECM 830 Square Wave BTX Electroporation System (Harvard Apparatus, Cambridge, Mass.) was used to deliver low-energy pulses to the liver tissue. Two metal plate electrodes, 2 cm in diameter, were attached to a pair of ratcheting vice grips (38 mm, Irwin Quick-Grips) using Velcro. High voltage wire was used to connect the electrodes to the BTX unit. The electrodes were clamped gently to the liver and the center-to-center distance between the electrodes was measured. The voltage output on the BTX unit was adjusted such that the approximate applied electric field was 1000 V/cm.

Figure 5A:
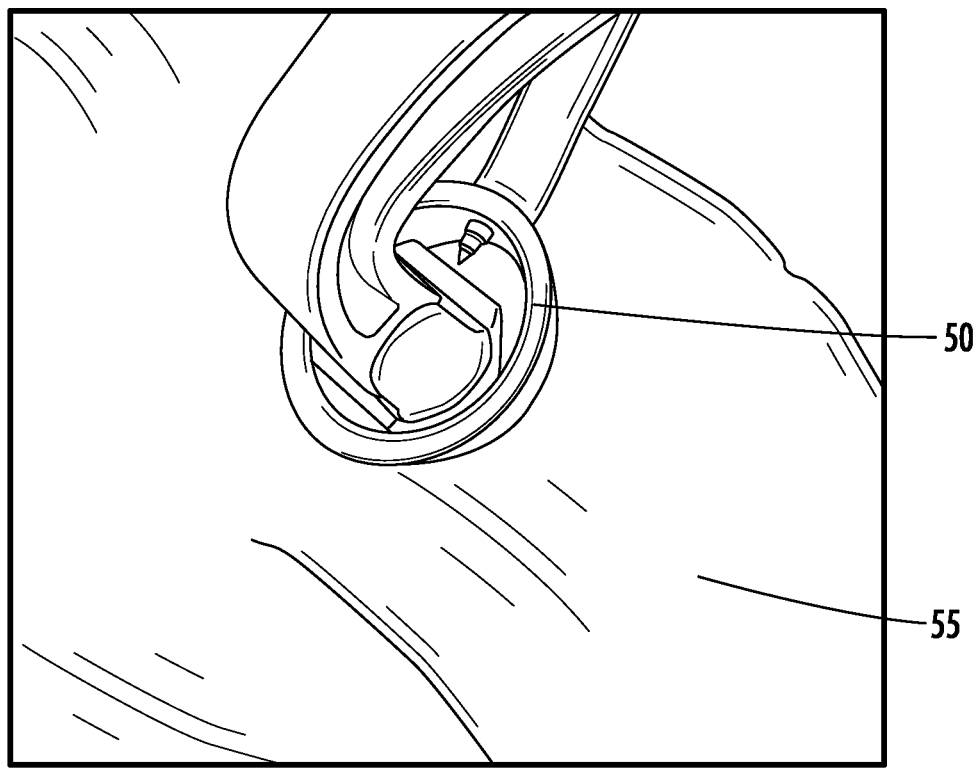
FIGS. 5A-B are drawings of (FIG. 5A) placement of the electrodes on actively perfused liver tissue and (FIG. 5B) the resultant lesion after treatment with 99, 100 µs, 1500V/cm pulses and 4 hours of perfusion, with the approximate area of the electrode is outlined in black.
Figure 5B:
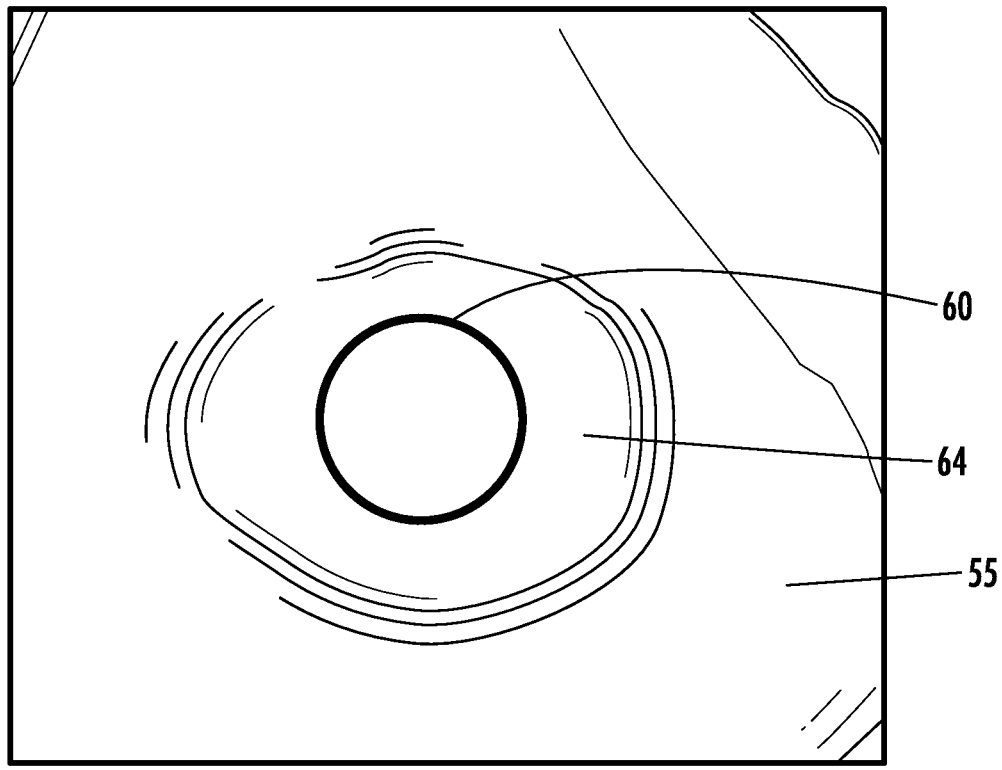

Ninety-nine individual 100-μs square pulses were administered at repetition rates of 0.25, 0.5, 1.0 and 4.0 Hz. Repetition rates trials were performed at random and repeated a minimum of three times. Sham controls were performed by placing the electrodes over the tissue without delivering any pulses. Two additional trials were performed using needle electrodes placed on a 0.5 cm gap using a voltage-to-distance ratio of 1500 V/cm at rates of 1 Hz and 4 Hz. The set up for this protocol is found in FIG. 5A. All N-TIRE treatments were completed within two hours post mortem. The surface lesion created at each treatment site was measured at the end of the 24 hour perfusion period. FIGS. 5A-B are drawings of (FIG. 5A) placement of the electrodes (one of which is shown by reference number 50) on actively perfused liver tissue 55 and (FIG. 5B) the resultant lesion 64 after treatment with 99, 100 μs, 1500V/cm pulses and 4 hours of perfusion, with the approximate area of the electrode outlined by region 60.

Following N-TIRE treatment and machine perfusion, livers were disconnected from the VasoWave™ system, sectioned to preserve lesions, and tissues were fixed by immersion in 10% neutral buffered formalin solution. After fixation, tissues were trimmed and processed for routine paraffin embedding, then sectioned at 4 micrometers, and stained with hematoxylin-eosin (H&E) and trichrome stains. Tissue sections were evaluated by a veterinary pathologist who had no knowledge of the N-TIRE treatment parameters.

Numerical modeling can be used to predict the electric field distribution, and thus provide insight into the N-TIRE treatment regions in tissue. Edd, J. F. & Davalos, R. V. Mathematical modeling of irreversible electroporation for treatment planning. *Technology in Cancer Research and Treatment* 6, 275-286 (2007) ("Edd 2007"). This has been chosen as the method to correlate lesion volume with an effective electric field threshold for the lesions created in the liver. The methods for predicting N-TIRE areas are similar to the ones described by Edd and Davalos. (Edd 2007). In order to understand the effective electric field threshold to induce N-TIRE in the liver, finite element simulations were conducted using Comsol Multiphysics 3.5a (Comsol, Stockholm, Sweden). The numerical model was constructed using 2 cm diameter plates, each 1 mm thick, placed above and below the tissue. The model was solved as prescribed by Garcia et al. (Garcia, P. et al. Intracranial nonthermal irreversible electroporation: in vivo analysis. *J Membr Biol* 236, 127-136 (2010)). The electric field distribution is given by solving the Laplace equation:

$$\nabla \cdot (\sigma \nabla \varphi) = 0$$

where σ is the electric conductivity of the tissue and φ is the potential.

The electrical boundary condition along the tissue that is in contact with the energized electrode is $\varphi = V_0$. The electrical boundary condition at the interface of the other electrode is $\varphi = 0$. The boundaries where the analyzed domain is not in contact with an electrode are treated as electrical insulation. The electrical boundary condition along the tissue that is in contact with the energized electrode is $\varphi = V_0$. The electrical boundary condition at the interface of the other electrode is $\varphi = 0$. The boundaries where the analyzed domain is not in contact with an electrode are treated as electrically insulative.

Conductivity changes due to electroporation and temperature have been modeled to calculate the dynamic conductivity according to the following equation: $\sigma_{dynamic}(\text{normE\_dc}) = \sigma_0 [1 + \text{flc2hs}(\text{norE\_dc} - E_{delta}, E_{range})]$ where $\sigma_0$ is the baseline conductivity, flc2hs is a smoothed heavyside function with a continuous second derivative that ensures convergence of the numerical solution. This function is defined in Comsol, and it changes from zero to one when $\text{normE\_dc} - E_{delta} = 0$ over the range $E_{range}$. In the function, normE_dc is the magnitude of the electric field, and $E_{delta}$ is the magnitude of the electric field at which the transition occurs over the range, $E_{range}$. In the simulations, the following were used: $E_{delta} = 500$ V/cm and $E_{range} = 100$ V/cm. The baseline tissue conductivity was of 0.286 S/m, and N-TIRE affected tissue was considered to double as used by Sel et al., reaching a final conductivity of 0.572 S/m. (See Boone, K., Barber, D. & Brown, B. Review—Imaging with electricity: report of the European Concerted Action on Impedance Tomography. *J. Med. Eng. Technol.* 21, 201-232 (1997); Sel, D., Lebar, A. M. & Miklavcic, D. Feasibility of employing model-based optimization of pulse amplitude and electrode distance for effective tumor electropermeabilization. *IEEE Trans Biomed Eng* 54, 773-781 (2007); Sel, D. et al. Sequential finite element model of tissue electropermeabilization. *IEEE Trans Biomed Eng* 52, 816-827, doi:10.1109/TBME.2005.845212 (2005); and Pavselj. N. et al. The course of tissue permeabilization studied on a mathematical model of a subcutaneous tumor in small animals. *IEEE Trans Biomed Eng* 52, 1373-1381 (2005)).

This numerical model was solved for the pulse parameters used on the livers in order to obtain a simulation of the electric field to which the tissue was exposed. The N-TIRE electric field thresholds were then found by measuring lesion dimensions and determining the electric field value at this region in the model.

Surface lesions develop during perfusion within 30 minutes initiating of treatment. The area of these on the liver surface created by plate electrodes were larger than, but the same type as that from the needle electrodes. In FIG. 5B, a 3.3 cm surface lesion produced from an applied voltage of 1500 V may be seen, taken 4 hours after treatment. Numerically modeled, this lesion size was produced within the region of tissue experiencing an electric field of 379±142 V/cm or greater. The results of the numerical model for this trial may be seen in FIGS. 6A-C.

The average applied voltage to distance ratio between the plates for the frequency trials was 962 V/cm. Lesions from these trials developed over 22 hours post-treatment, and were 2.5 cm in diameter on average (125% electrode diameter); with a minimum lesion of 2 cm occurring at 0.25 Hz and 936 V/cm, and maximum lesion of 3.2 cm occurring at 1.0 Hz and 950 V/cm. Though not dramatically significant, the results suggest that lesion sizes were on average greatest at 1 Hz and decreased as the frequency increased or decreased. The lesions which developed after treatments applied at 0.25 and 4 Hz were statistically smaller ($\alpha=0.1$) than those which developed for treatments applied at 1 Hz (FIGS. 7A-B).

Analysis of the treated tissue reveals a uniform treatment region that extended cylindrically through the tissue. This resulted in calculated treated volumes between 1.97 cm$^3$ and 6.37 cm$^3$ for corresponding tissue thicknesses of 0.628 and 0.792 cm.

Figures 8A, 8B:
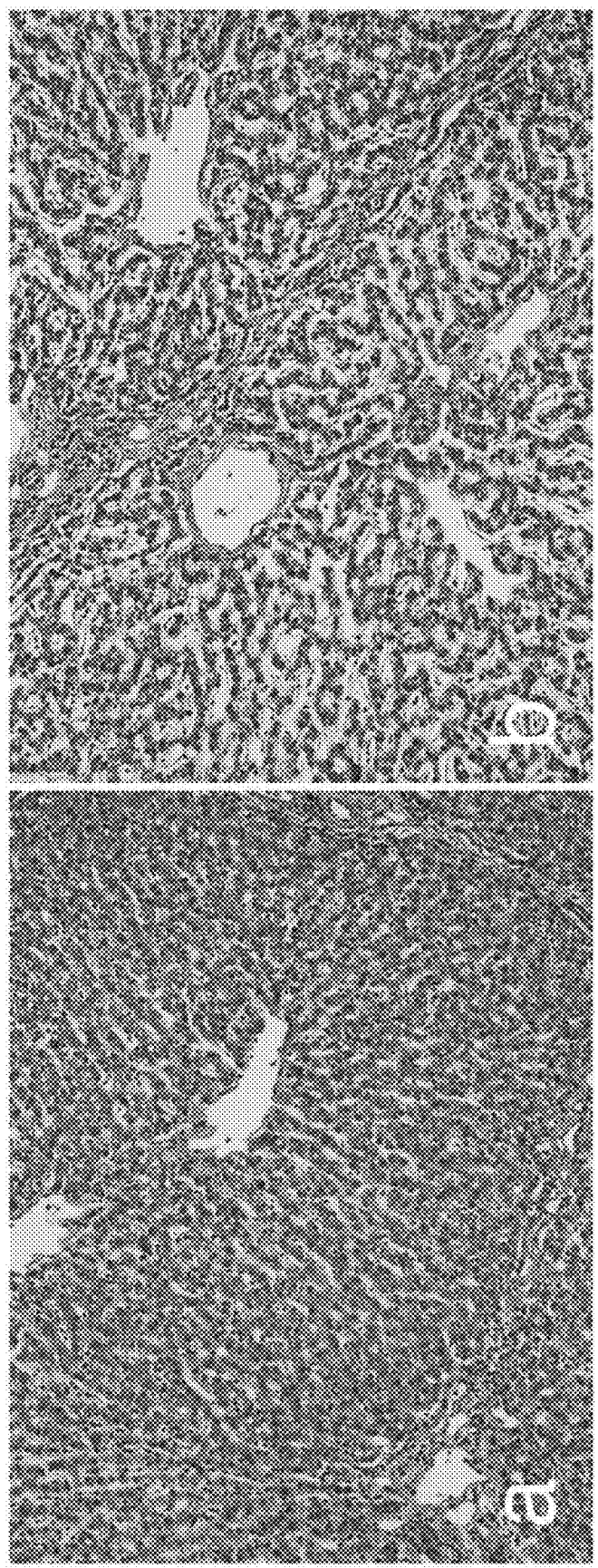
FIGS. 8A-B are micrographs showing a histological comparison of untreated liver tissue to areas which have undergone mild IRE treatments showing preservation of connective tissue and blood vessels.

On histological examination from 24 hours post-treatment, the treated regions exhibit cell death (FIG. 8B) compared to controls (FIG. 8A). More specifically, FIGS. 8A-B show the histological comparison of untreated liver tissue to areas which have undergone mild IRE treatments showing preservation of connective tissue and blood vessels. Samples stained with H&E from (FIG. 8A) untreated and (FIG. 8B) ninety nine, 100 µs, 100 µs, 100 Vcm pulses using plate electrodes 24 hours of cardio emulation perfusion at 10×.

Hepatic acini in pigs are bordered by connective tissue, which contains blood vessels and biliary structures, and have a prominent cord architecture terminating in a hepatic venule. In areas adjacent to energy delivery, hepatic cell cords were well preserved, with mildly vacuolated hepatocytes (an expected finding at 24-hour ex vivo machine perfusion cycle). Sinusoidal structure in untreated areas is open, reflecting the flow of perfusate between hepatic artery/portal vein and hepatic vein. N-TIRE treatment disrupts hepatic cords and induces cell degeneration (FIG. 8B). Preservation of major acinar features, including connective tissue borders and blood vessels, is seen. In zones of N-TIRE treatment, cell cords were indistinct and membranes lining sinusoids are fragmented to varying degrees.

Pigs, like humans, have substantial separation of liver acini by thin bands of fibrous connective tissue that run between portal triads. This macrostructure had an effect on the distribution of lesions induced by electroporation. Lesions are confined within structural acini in a manner that at the edges of the electroporation field, acini with lesions could border normal or nearly normal acini. Thus, the bands of connective tissue act as insulation for the electrical pulsing, an important observation when considering procedures for treating focal liver lesions with electroporation or for evolving an intact connective tissue/duct/vascular matrix for subsequent tissue engineering.

FIGS. 9A-C are micrographs showing (FIG. 9A) A section of untreated liver after 24 hours of perfusion. Sections of the same liver treated with 90, 1500V/cm, 100 µs pulses at 4 Hz using needle electrodes after 24 hours of perfusion at (FIG. 9B) 10× and (FIG. 9C) 20× magnification.

FIG. 9A shows a portion of untreated porcine liver with normal sinusoidal cell cords arrayed from portal tracts to central vein. Cell morphology is well preserved. Some vascular congestion with red blood cells is noted and there is also mild centrilobular biliary stasis. Mildly damaged porcine acini are observed in regions subjected to plate electroporation (FIG. 9B). The center of the acinus shows disruption of cord architecture and some cell degeneration and clumping. A higher magnification view of this area is shown in FIG. 9C, where cellular changes are more readily appreciated. These treated regions display mild lesions consisting of hepatocytic cord disruption and cells delaminating from cord basal laminae. Mild biliay stasis is noted (dark pigment).

Administration of N-TIRE treatment, either with needle electrodes or with plate electrodes produced lesions in some hepatic acini that are distinctive. The severity of lesions within individual acini ranges from mild to moderately severe. Mild lesions consisted of small clumps of hepatocytes that detach from basal membranes. These cells show a loss of organization of fine intracellular structure and clumping of cytoplasm/organelles (FIGS. 9A-C).

Figures 10A, 10B:
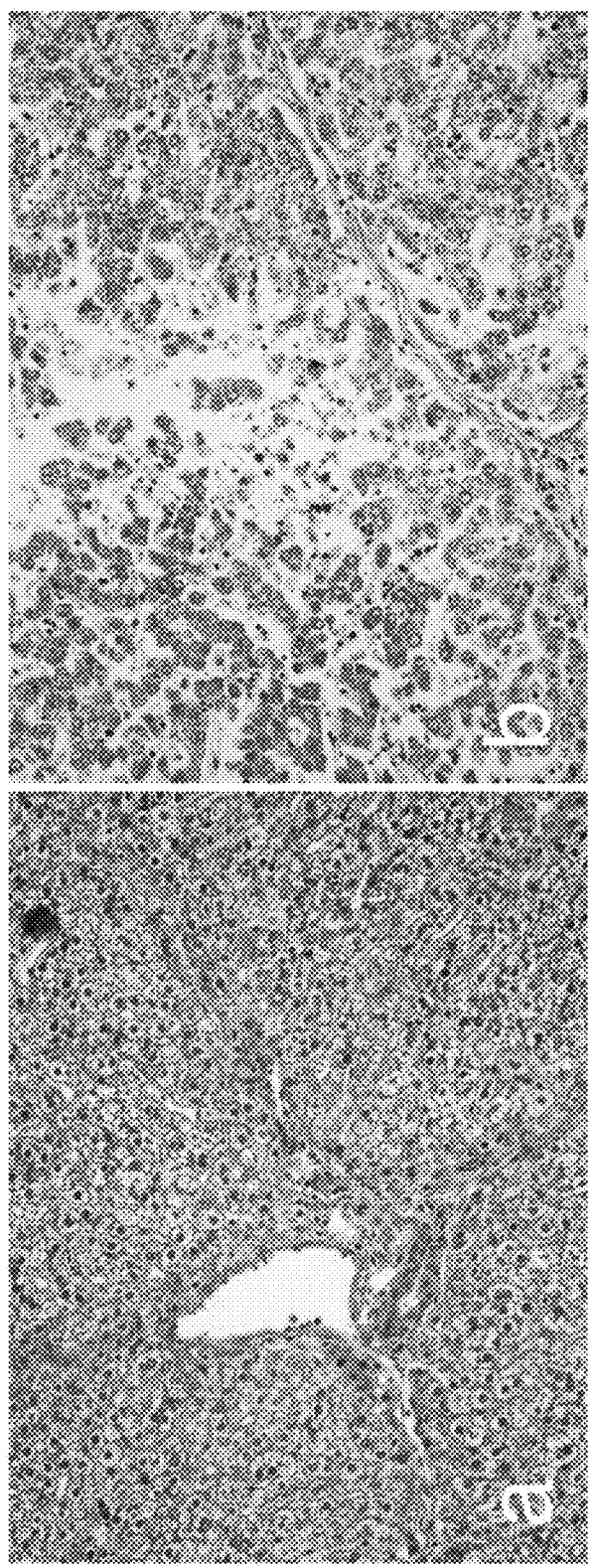
FIGS. 10A-B are micrographs showing (FIG. 10A) A section of untreated liver after 24 hours of perfusion and (FIG. 10B) the same liver treated with 100, 1500V/cm, 100 µs pulses at 1 Hz using needle electrodes after 24 hours of perfusion at 20× magnification.

Moderately severe lesions are readily discerned (FIGS. 10A-B). Cells affected by the N-TIRE procedure show varying degrees of cell swelling and karyolysis (FIG. 10B). Within individual acini, most cells are affected. In some acini, frank nuclear pyknosis and cellular degeneration is seen, with small clumps of hyperchromic cells unattached from basal membranes. In some acini, centrilobular biliary stasis is noted, with aggregation of bile pigments in distal sinusoidal spaces. In all cases, as noted, bridging bands of connective tissue, with intact bile ducts and vascular structures are seen, even immediately bordering acini with significant N-TIRE-induced tissue damage.

This work reports the effect of non-thermal irreversible electroporation in an actively perfused organ for use in creating decellularized tissue scaffolds for organ transplantation. The results reported here were localized to volumes of tissue up to 6.37 cm$^3$ for a single N-TIRE treatment. This can readily be expanded into much larger volumes by performing multiple treatments with the goal of creating decellularized structures for partial and full liver transplants. After 24 hours of perfusion, a quantity of cellular debris usually remained within the tissue construct. Removal of this debris is essential in minimizing immune response of recipients and can be accomplished through longer and more efficient perfusion protocols and/or using the body's own mechanisms of perfusion to maximize the removal of cellular constituents.

In addition to producing decellularized tissue scaffolds, these methods provide an ideal platform to study the effects of pulse parameters such as pulse length, repetition rate, and field strength on whole organ structures. Additionally, since there is direct control over the electrical properties of the perfusate, this could serve as a model for examining the effects of N-TIRE on diseased or cancerous organs with unique electrical or physical properties. Methods of the invention can be applied to treat portions of diseased tissue or organs to remove unwanted or diseased tissue, then re-seeding of the organ or tissue can be performed. For example, a patient with liver disease could be treated to address just the damaged regions of the liver through the vasculature and allow the body to decellularize and reseed that section on its own.

The resulting scaffolds from N-TIRE plus perfusion maintain the vasculature necessary for perfusion into structures far beyond the nutrient diffusion limit that exists for non-vascularized structures. Since the temperature of the perfusate used can be as low as 4° C., thermal aspects associated with Joule heating are negligible. This provides an ideal platform in which to explore the effects on the cells and tissue of electric fields in isolation from the effects of thermal damage. Additionally, the low temperature of the organ compared to in vivo applications may allow for the application of much higher voltages to attain appropriate electric fields for decellularizing thicker structures without inducing thermal damage. This is important since the thickness of a human liver can exceed 10 cm in some regions.

As shown and described herein, when planning to decellularize tissues and organs undergoing active perfusion, the treatment region of decellularized tissue may be predicted through numerical modeling. From the lesion sizes and numerical model used here, when decellularizing an entire organ for a transplantable scaffold, the protocol should expose all of the tissue to an electric field of 379±142 V/cm. This will ensure complete cell death, allowing comprehensive reseeding of the scaffold with the desired cells, thus minimizing the effects of recipient rejection. It is noted that the threshold found here is slightly lower than ones in previous investigations, which may be a result of the unique pulse parameters used or an inherent increased sensitivity of the cells to the pulses when under perfusion.

Continuous active machine perfusion in the decellularization process may also be advantageous for recellularization. Once the decellularization process is complete, it should be possible to reseed the scaffold without risking damage attendant with removing the newly-created scaffold from the perfusion system. Since the arterial and venous supplies are individually addressable, multiple cell types can be delivered simultaneously to different regions of the organ. Similarly, retrograde perfusion through the biliary system may be the ideal pathway in which to deliver hepatocytes for the reseeding process.

Lesions seen microscopically are clearly indicative of a mechanism and morphology for cellular stripping using electroporation. It is very interesting that even at 24 hours, when using the electroporation parameters described here, there is only a modest loss of acinar architecture. More stringent conditions of energy delivery could likely alter this, but this might induce damage to important connective tissue and vascular structures. Addition of adjuvant cytotoxic agents, enzymes, and detergents in the perfusion fluid also might modulate the severity and temporal nature of cell stripping. Logically, it is much better to build on mild conditions, preserving important architecture for tissue engineering purposes, than to rapidly obliterate cells and stroma. The ability to manage the period of perfusion and conditions of perfusion with the cardioemulation system has clear advantages for this gradual, evolutionary approach to decellularization and eventual recellularization of liver.

Example II—Vasculature Administered IRE with Active Perfusion

A normal kidney was procured, through standard and approved means, from a pig after death. When obtained, the renal artery and vein of the kidney were isolated and connected with fittings to allow anastomosis to a cardiovascular emulation system (CVES) (VasoWave 2.3™, Smart Perfusion LLC, Denver, N.C.). The organ was connected to the CVES and the kidney was flushed with 1.5 liters of Krebs-Hensleit/Glutathione physiologic solution over a period of 5 minutes.

The kidney was then anastomosed on the arterial and vascular connectors to the CVES and perfusion was started (arterial systolic pressure: 110 mm Hg, diastolic pressure 60 mm Hg, with a physiologic pulse train delivered at 60 beats per minute). Perfusion was performed at 25° C. The renal vein was left disconnected but the end of the tubing was elevated to generate a low backpressure (this approximated 1 mm Hg). Perfusion was stabilized over a 15 minute interval. The Krebs solution conductivity was measured at 0.72 S/m.

Figure 11:
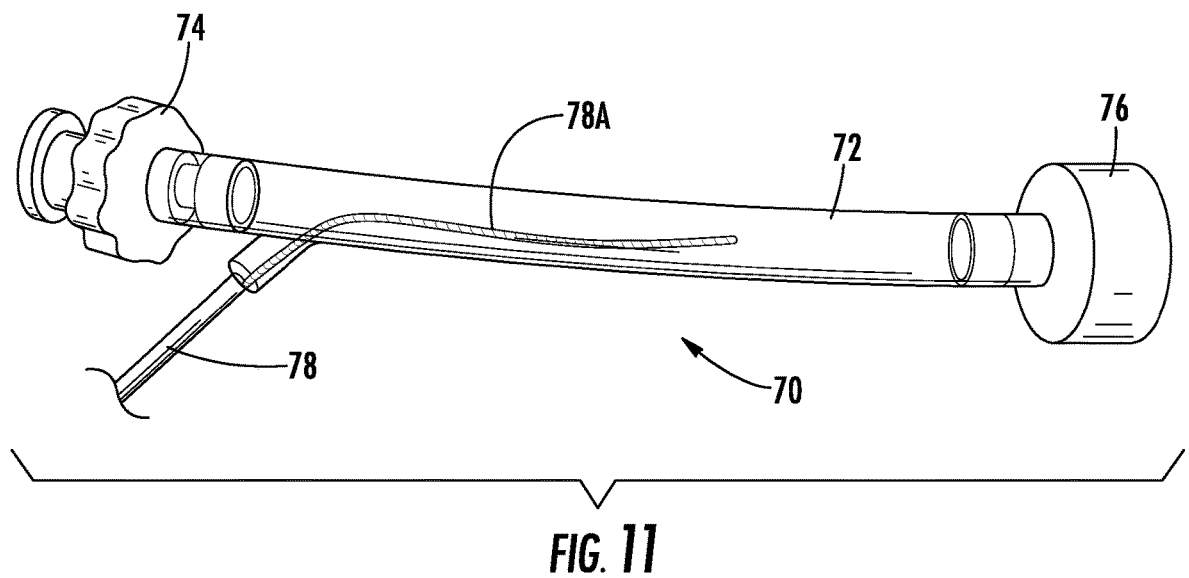
FIG. 11 is a drawing of a perfusion electrode according to the invention.

As shown in FIG. 11, customized energy application electrodes can be fabricated for a particular application. In this example, an electroporation device 70 was created by piercing a small section of flexible tubing 72 near its center point, inserting an insulated wire electrode 78 with an exposed tip 78A (e.g., some portion of bare wire or enamel coated wire with an exposed tip) through the hole and sealing the site with adhesive. The enamel on ends of the wire was removed to create electrical connections within the tubing and externally while providing an insulating coating around the majority of the wire for safety. In addition, shrink wrap tubing was applied along the length of the tubing for further electrical insulation. Luer lock connections 74, 76 were then inserted into the ends of the tubing to facilitate connection to the perfusion system. This electrode configuration presented less than 1 ohm of resistance between the pulse generation system and the perfused fluid. As shown in FIG. 11, a small diameter wire is situated inside the tubing and is accessible from the outside, which allows for pulses to be delivered simultaneous with perfusion.

Figure 12:
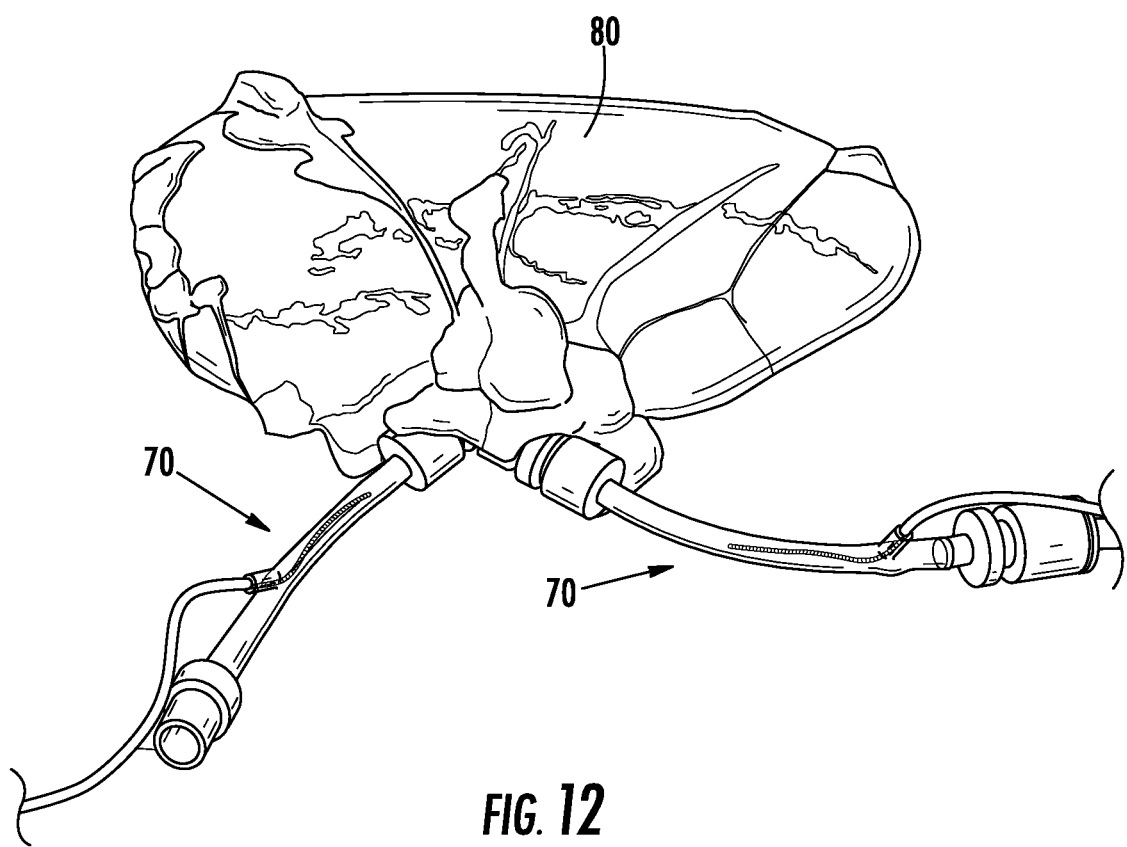
FIG. 12 is a drawing showing a kidney simultaneously attached to the prototype electrodes and perfusion system by way of the renal vein and artery.

FIG. 12 is a drawing showing a kidney 80 simultaneously attached to the prototype electrodes 70 and perfusion system by way of the renal vein and artery. One electrode was placed in-line between the arterial supply from the CVES and the kidney vascular connector. The venous electrode was connected to the renal vein vascular connector on one end, while the other end of the electrode tubing was propped up with a syringe to create the backpressure. This also prevented the electrical current from finding a path of least resistance through the perfusate backwards through the CVES or sending a partial current through the system and the kidney.

The resistance and capacitance of the vascular network was measured with an LCR meter. At low frequencies (100 Hz) the resistance and capacitance values measured were 372.6 k Ohms and 0.248 nano-Farads, respectively. This yields an RC time constant of 92.4 microseconds and a complete decay time (5*RC) of approximately 462 microseconds.

Figure 13:
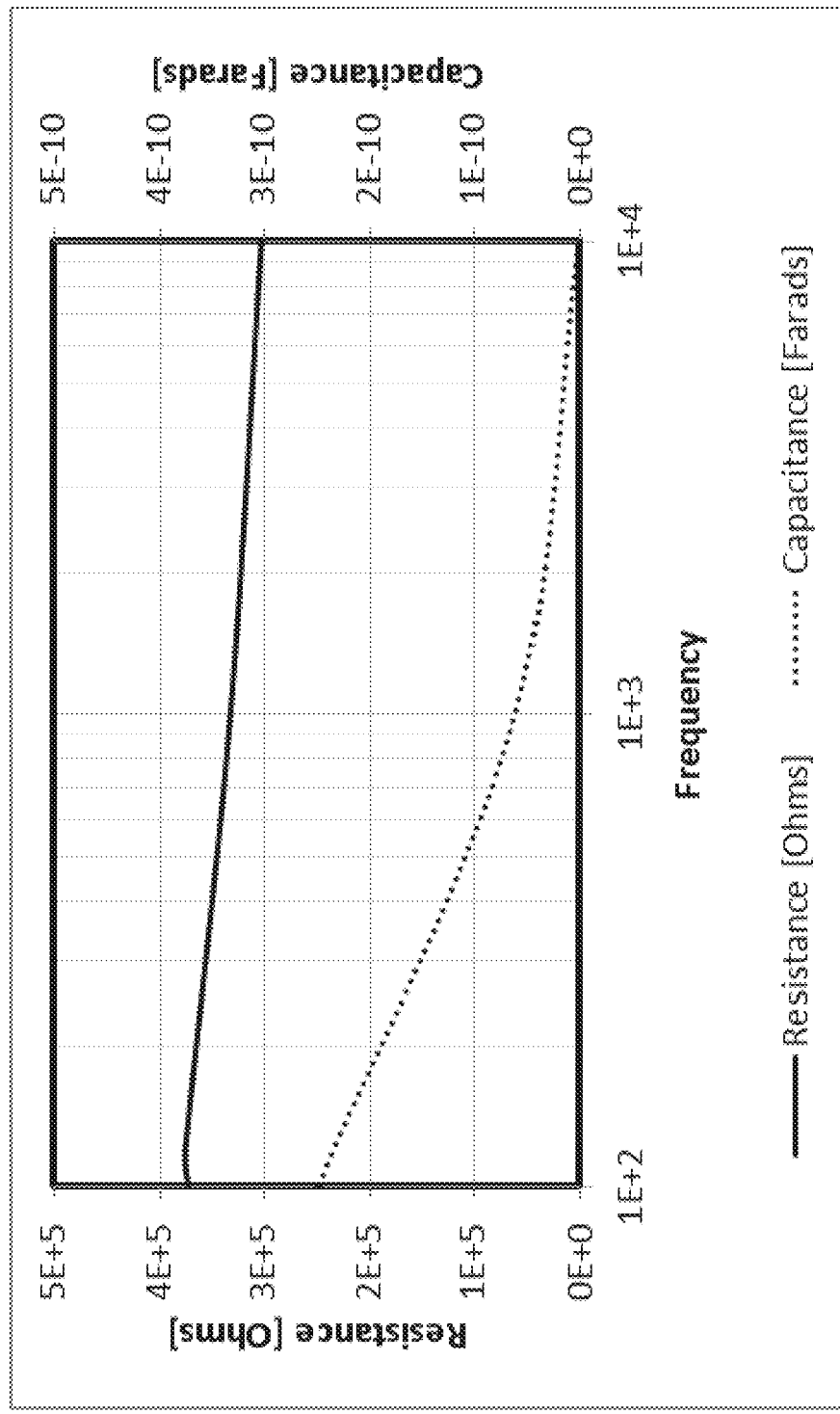
FIG. 13 is a graph showing impedance measurements from the kidney prior to pulsing, which presented a significant electrical resistance and capacitance.

As demonstrated in FIG. 13, which provides impedance measurements from the kidney prior to pulsing, the organ presented a significant electrical resistance and capacitance. The trend observed between 100 and 10,000 Hz (FIG. 13) indicates that for square wave pulses which have a large direct current DC component, the RC time constant should be larger. A single 50 micro-second pulse was delivered through the vasculature at voltages of 100, 500, 750, 1000, 1500, and 2000 V using a BTX pulse generator (Harvard Apparatus). The current delivered and the decay time of the pulse was recorded. In all cases, the decay time was less than predicted.

Figure 14:
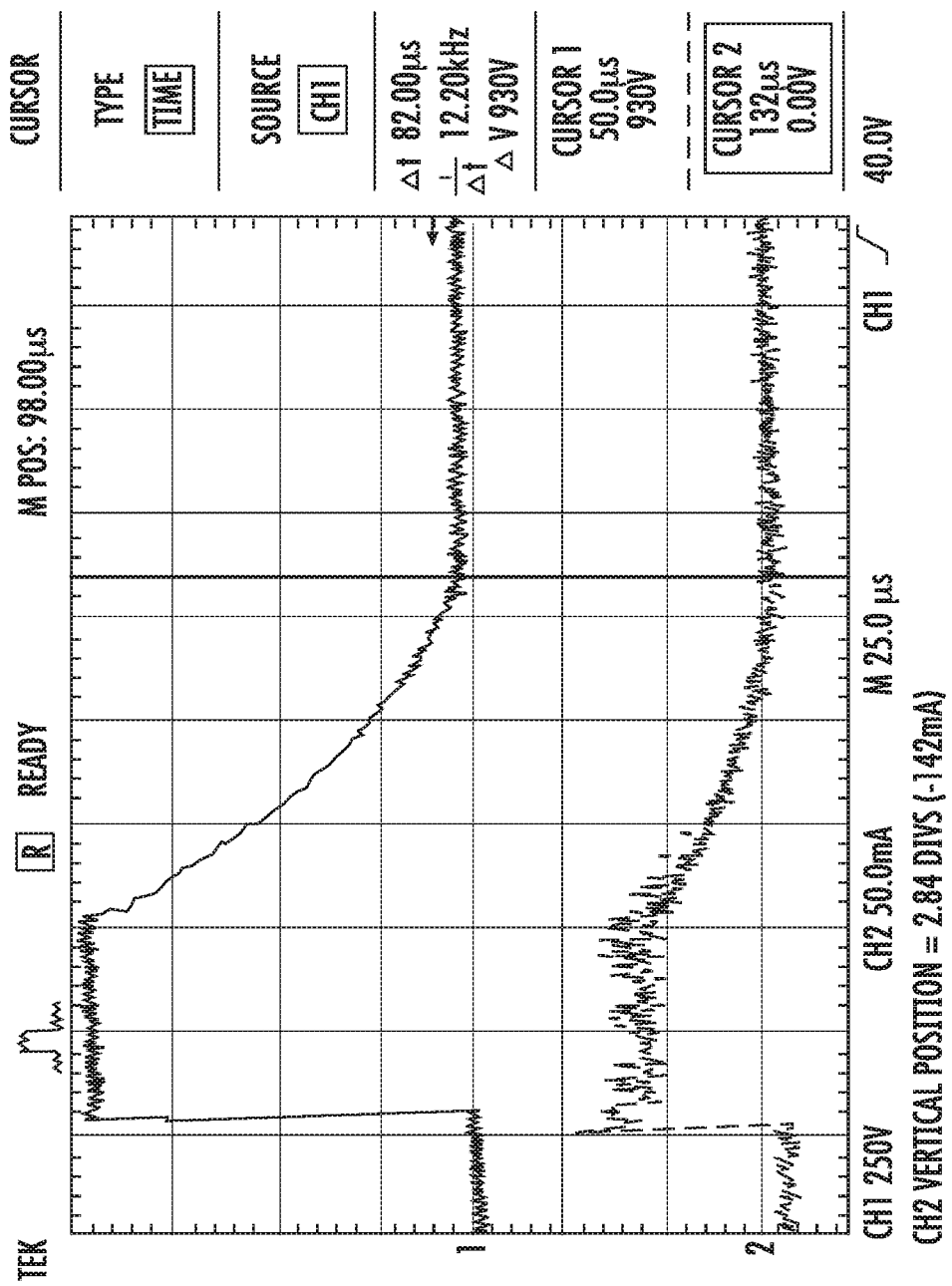
FIG. 14 is a drawing of a monitor output showing a resultant waveform from a 50 microsecond pulse with amplitude of 1000V.

The resultant waveform is shown in FIG. 14. More particularly, FIG. 14 provides the resultant waveform from a 50 microsecond pulse with amplitude of 1000 V. Decay of the pulse is characteristic of a tissue with both resistive and capacitive components. A representative pulse voltage and current plots can be seen in FIG. 14. The decay time decreased significantly between 100 V and 500 V and remained relatively constant at voltages between 500 and 2000 V. In all cases, the delivered current was (23-53%) greater than expected based on calculations.

Figure 15:
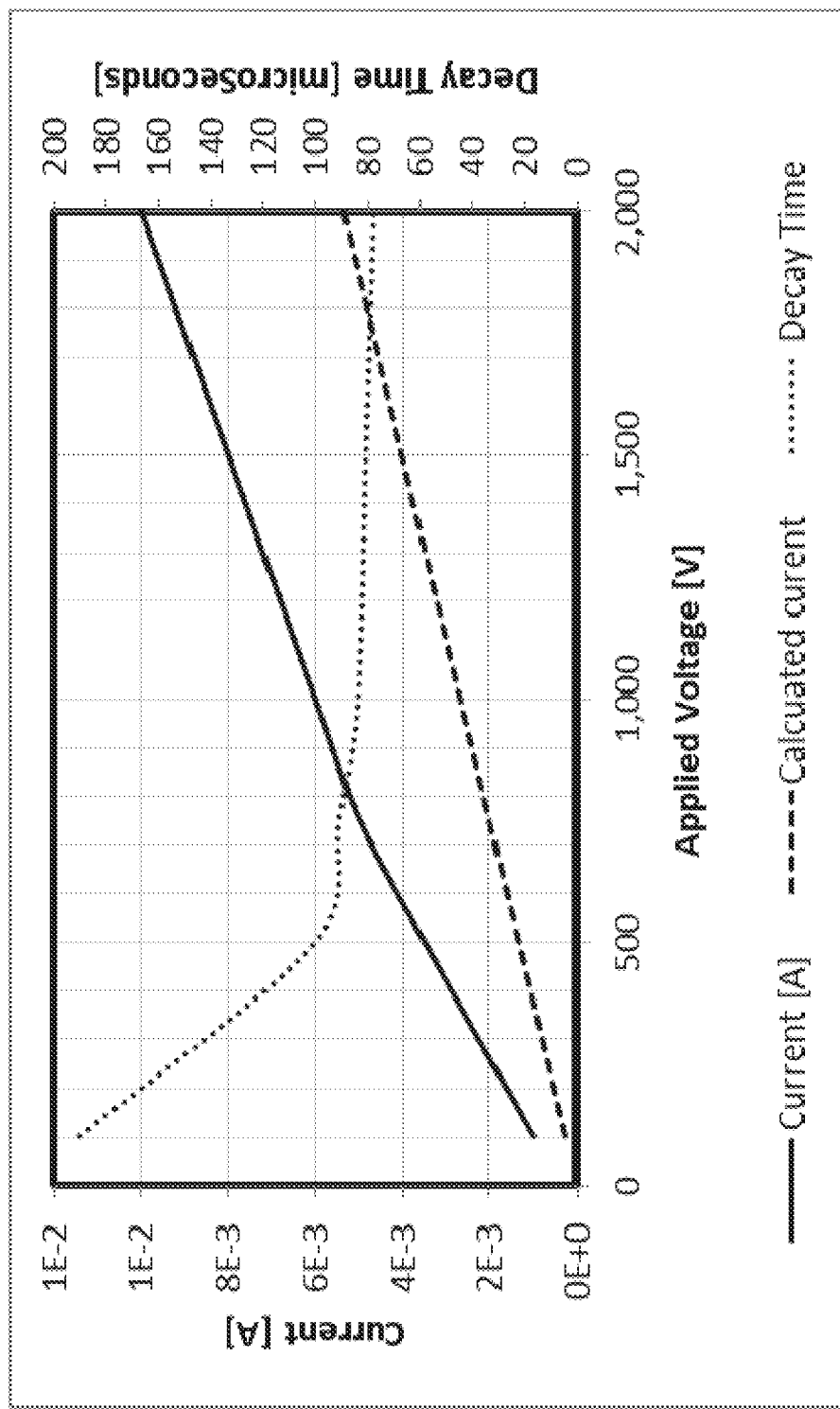
FIG. 15 is a graph showing the maximum current delivered and decay time for pulses delivered with amplitudes between 100 and 2000 V.

FIG. 15 is a graph showing the maximum current delivered and decay time for pulses delivered with amplitudes between 100 and 2000 V. Trends indicate that for pulses of 500 V and above, the resistance of the tissue has decreased due to electroporation. The organ was then subjected to 200 pulses at 1000 V, with a repetition rate of one pulse every second.

Figure 16:
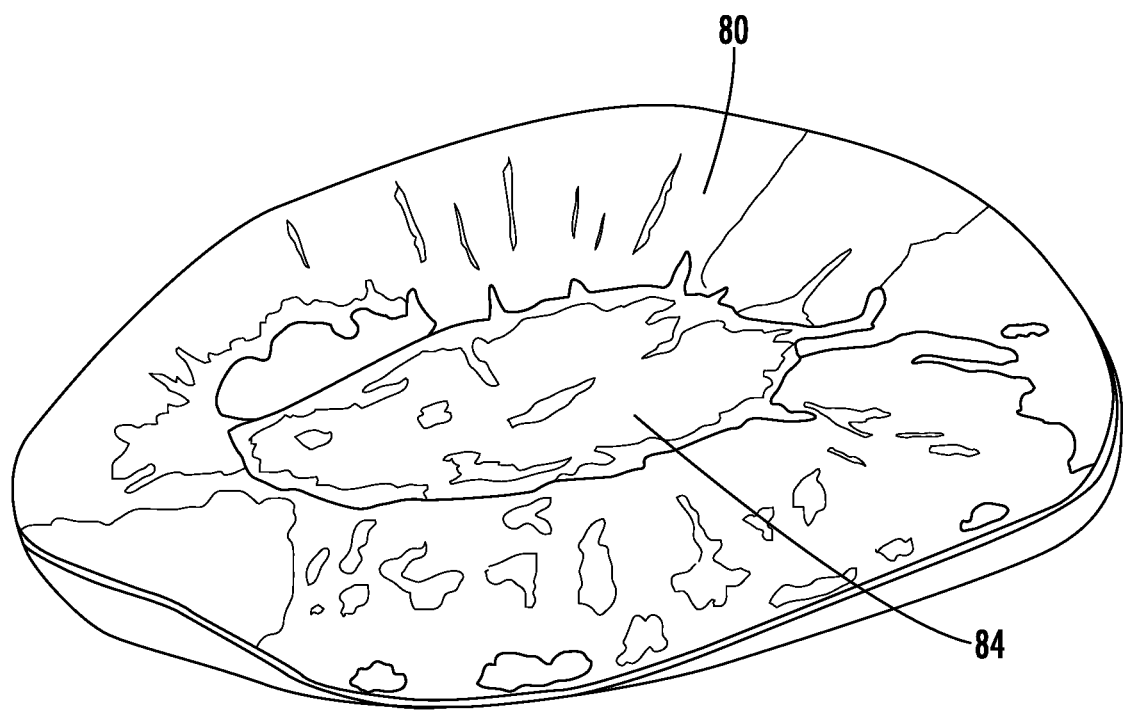
FIG. 16 is a drawing showing a kidney section 30 minutes after pulsing, wherein area 80 indicates live tissue and area 84 indicates regions ablated by the IRE pulses.

TTC stain (2% in Krebs solution) was administered by perfusion for 15 minutes after pulsing was completed and the organ remained on the perfusion system for another 30 minutes. The TTC stain is used to delineate viable and non-viable tissue, via the formation of a colored reaction product (a red formazan) through the activity of tissue dehydrogenases. Viable tissue, capable of oxidative respiration, is shown at 80; devitalized or ischemic tissue is pale in comparison, shown at 84. As shown in FIG. 16, Kidney sections a kidney section 30 minutes after pulsing shows areas indicative of live tissue, region 80, and areas indicative of regions ablated by the IRE pulses, region 84. The sectioned organ was placed in formalin for fixation and histology. It is obvious from this figure that a large volume of the kidney underwent irreversible electroporation. Blood clots in the vasculature may have prevented the entire organ from undergoing electroporation. This issue can be resolved by flushing the vasculature of the organ immediately after surgical resection.

Figure 17:
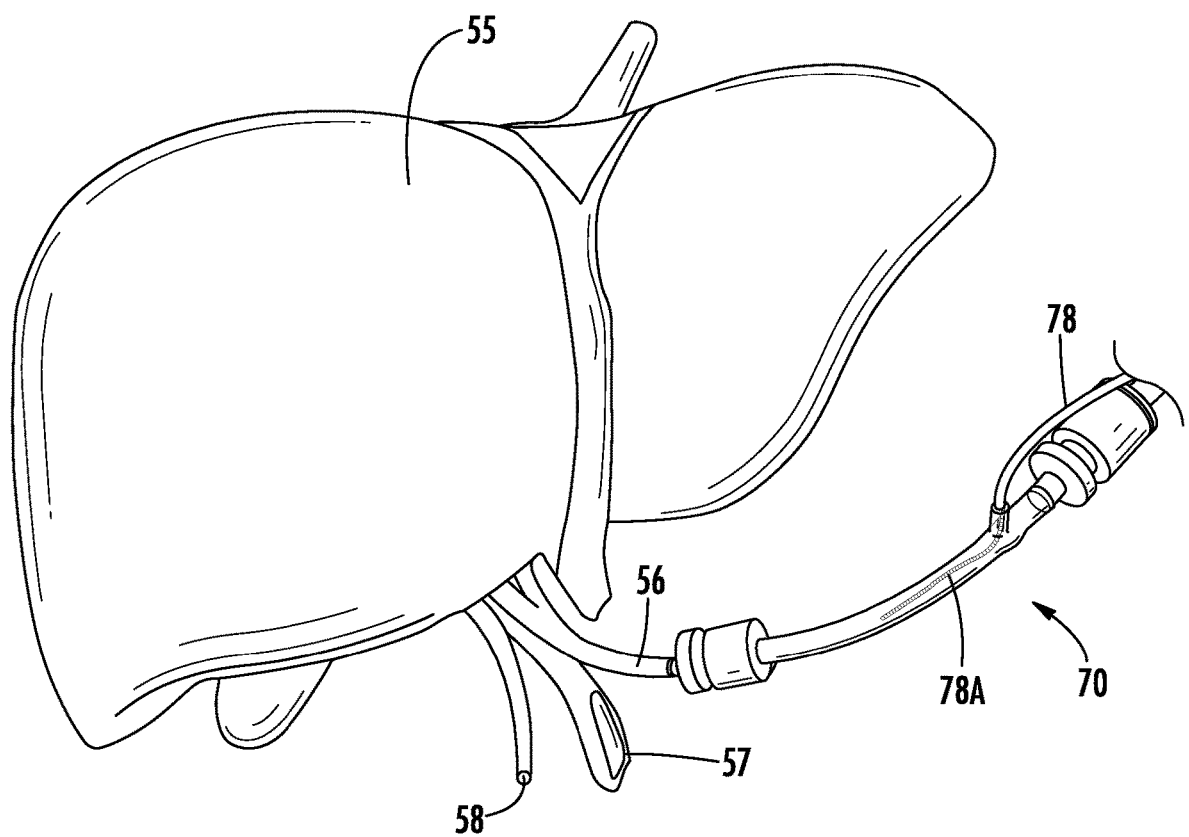
FIG. 17 is a drawing depicting placement of one electrode, where one device is disposed in an artery.
Figure 18:
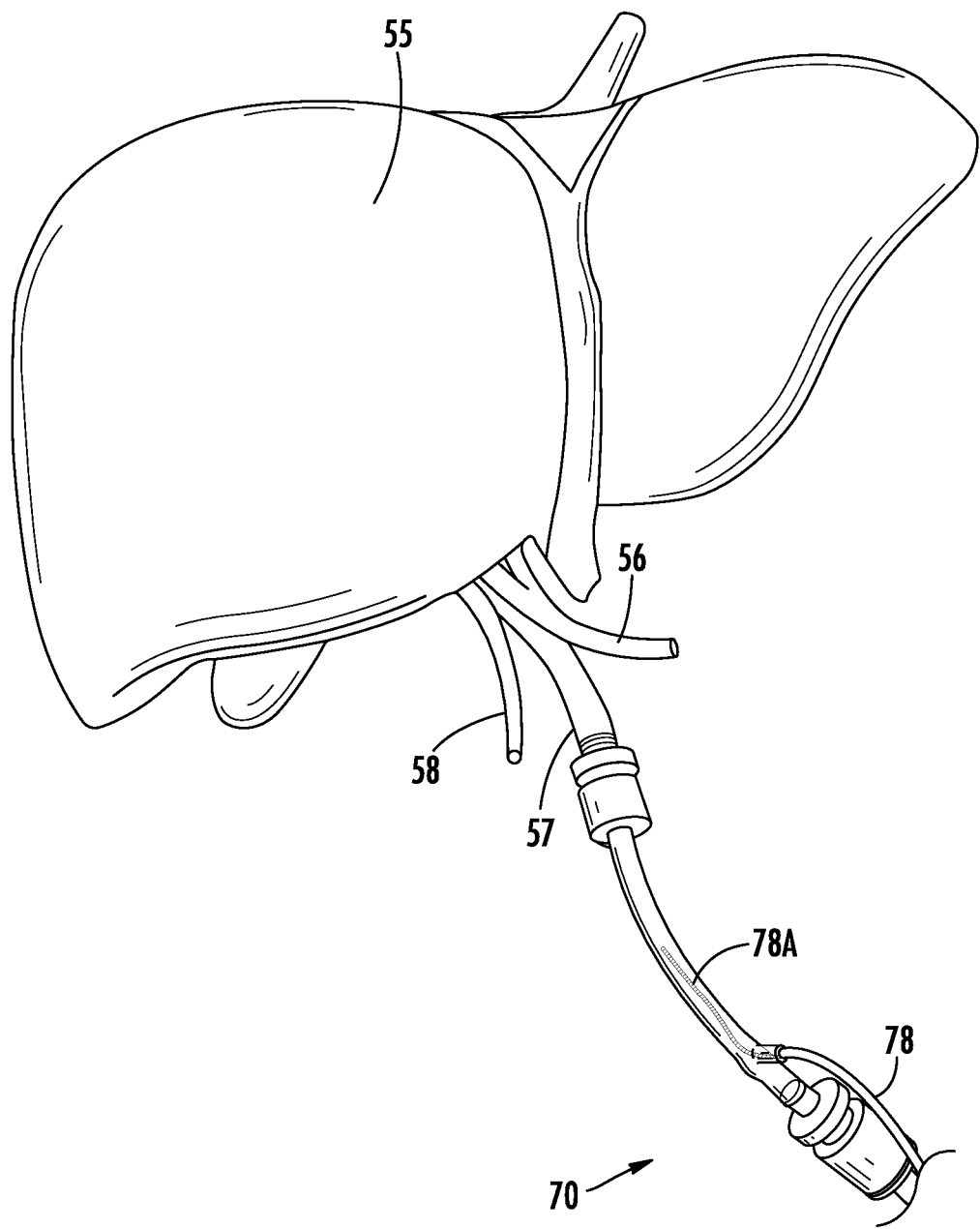
FIG. 18 is a drawing depicting placement of one electrode, where one device is disposed in a vein.
Figure 19:
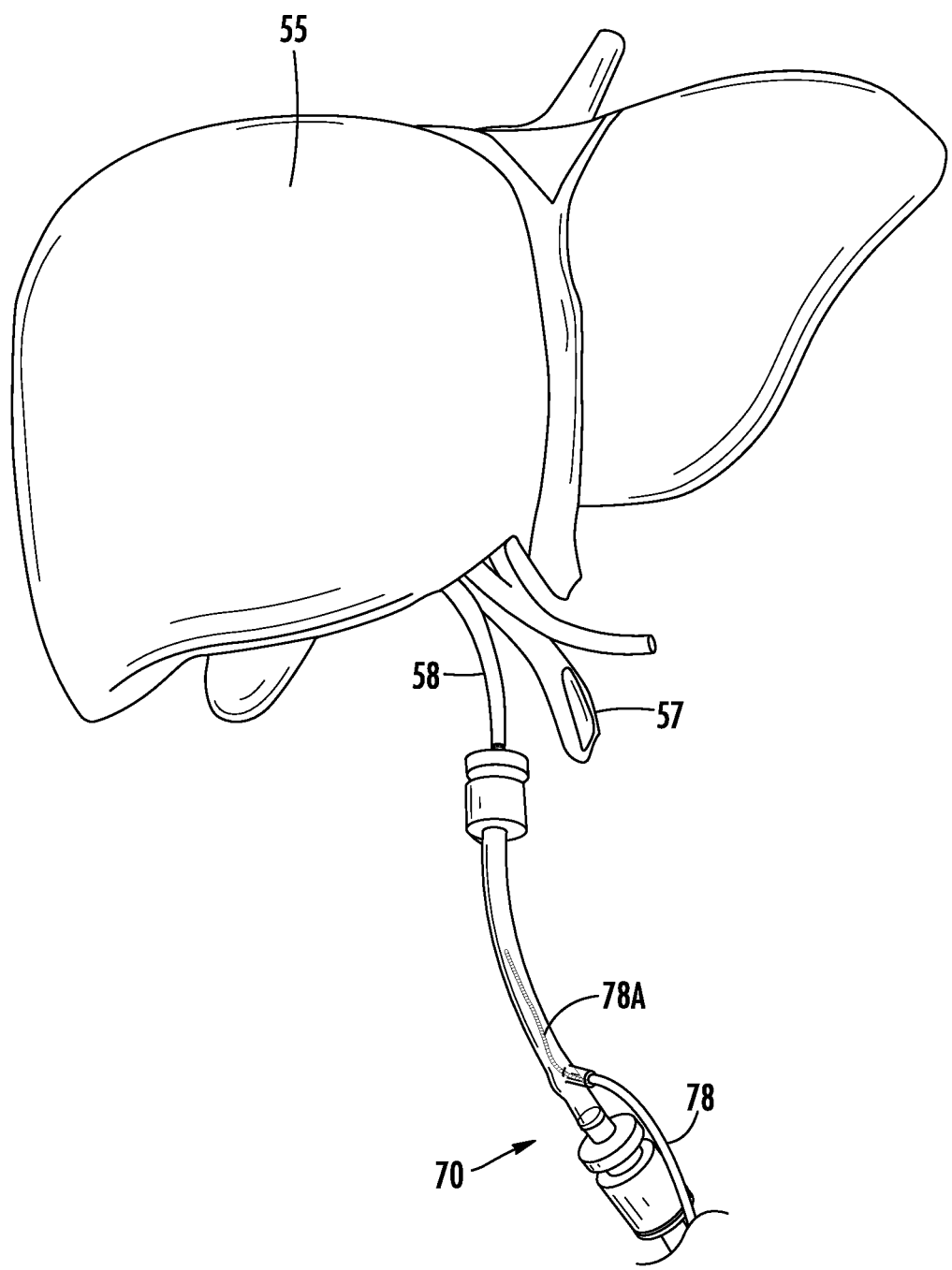
FIG. 19 is a drawing depicting placement of one electrode, where one device is disposed in a bile duct.

FIGS. 17-19 are drawings showing that electroporation devices and systems of the invention can be disposed in communication with blood vessels and conductance structures of organs, such as the liver. FIG. 17 shows device 70 (with electrode 78 comprising an exposed tip 78A) placed in hepatic artery 56 of liver 55. For reference, portal vein 57 and bile duct 58 are also shown. FIG. 18 is a drawing depicting one electroporation device 70 disposed in portal vein 57 of liver 55. FIG. 19 is a drawing depicting one device with electrode placed into the bile duct 58 of a liver.

The vasculature and microvasculature of an organ can be used to deliver brief but intense electrical pulses to bulk tissue resulting in non-thermal cell death while maintaining the structure and function of the underlying extracellular matrix. Histological staining will be used to evaluate the overall health of the tissue (H&E), damage and removal of endothelial cells (vWF), and the structure of the extracellular matrix (trichrome) and the resultant decellularization of these preliminary experiments. The 4 hour total perfusion protocol can be used as a baseline for decellularization protocols and has extensions outside of tissue engineering, such as to treat solid tumors which are embedded deep inside vascularized organs.

Once engineered scaffolds are prepared, the scaffolds can be further engineered to regenerate within a living body or engineered into tissues and organs acceptable for transplantation into a living body. Methods of making engineered tissues can comprise: seeding an engineered scaffold according to the invention with a cell of interest, and exposing the seeded scaffold to conditions whereby the seeded cells can infiltrate the scaffold matrix and grow. Seeding of the scaffold can be by any technique known in the art. Likewise, exposing the seeded scaffold to conditions whereby the cells can infiltrate the scaffold and grow can be any technique known in the art for achieving the result. For example, it can comprise incubating the seeded scaffold in vitro in a commercial incubator at about 37° C. in commercial growth media, which can be supplemented with appropriate growth factors, antibiotics, etc., if desired. Those of skill in the art are fully capable of selecting appropriate seeding and proliferation techniques and parameters without a detailed description herein. In other words, with respect to seeding and growth of cells, the scaffolds of the present invention generally behave in a similar manner to other natural scaffolds known in the art. Although the present scaffolds have beneficial properties not possessed by other scaffolds, these properties do not significantly affect seeding and growth of cells.

Engineered tissues have been developed as replacements for injured, diseased, or otherwise defective tissues. An important goal in the field of tissue engineering is to develop tissues for medical/therapeutic use in human health. In view of the difficulty and ethical issues surrounding use of human tissues as a source of scaffolds, tissues from large animals are typically used for the source material for natural scaffolds. The xenotypic scaffolds are then seeded with human cells for use in vivo in humans. While the presently disclosed engineered tissues are not limited to human tissues based on animal scaffolds, it is envisioned that a primary configuration of the engineered tissues will have that makeup. Thus, in embodiments, the engineered tissues of the invention are tissues comprising human cells on and within a scaffold derived from an animal tissue other than human tissue.

For certain in vivo uses, animal tissue is subjected in vivo to non-thermal IRE, and the treated tissue cleared of cell debris by the host animal's body. Thus, in certain in vivo embodiments, no secondary cell debris removal step is required, as the host animal's body itself is capable of such removal (this concept applies to in vivo creation of scaffolds in humans as well). The treated tissue is then seeded in vivo, for example with human cells, and the seeded cells allowed to infiltrate the scaffold and grow. Upon suitable infiltration and growth, the regenerated tissue is removed, preferably cleaned of possible contaminating host cells, and implanted into a recipient animal, for example a human. In such a situation, it is preferred that the host animal is one that has an impaired immune system that is incapable or poorly capable of recognizing the seeded cells as foreign cells. For example, a genetically modified animal having an impaired immune system can be used as the host animal. Alternatively, for example, the host animal can be given immune-suppressing agents to reduce or eliminate the animal's immune response to the seeded cells.

The recipient or host animal can be any animal, including humans, companion animals (i.e., a pet, such as a dog or cat), farm animals (e.g., a bovine, porcine, ovine), or sporting animals (e.g., a horse). The invention thus has applicability to both human and veterinary health care and research fields.

Whether in vivo or in vitro or ex vivo, the choice of cells to be seeded will be left to the practitioner. Many cell types can be obtained, and those of skill in the tissue engineering field can easily determine which type of cell to use for seeding of tissues. For example, one may elect to use fibroblasts, chondrocytes, or hepatocytes. In embodiments, embryonic or adult stem cells, such as mesenchymal stem cells, are used to seed the scaffolds. The source of seeded cells is not particularly limited. Thus, the seeded cells may be autologous, syngenic or isogenic, allogenic, or xenogenic. Because a feature of the present invention is the production of scaffolds and tissues that have reduced immunogenicity (as compared to scaffolds and tissues currently known in the art), it is preferred that the seeded cells be autologous (with relation to the recipient of the engineered tissue). In certain embodiments, it is preferred that the seeded cells be stem cells or other cells that are able to differentiate into the proper cell type for the tissue of interest.

Alternatively or additionally, the in vivo method of creating a scaffold and the in vivo method of creating an engineered tissue can include treating tissue near the non-thermal IRE treated cells with reversible electroporation. As part of the reversible electroporation, one or more genetic elements, proteins, or other substances (e.g., drugs) may be inserted into the treated cells. The genetic elements can include coding regions or other information that, when expressed, reduces interaction of the cells with the seeded cells, or otherwise produces anti-inflammatory or other anti-immunity substances. Short-term expression of such genetic elements can enhance the ability to grow engineered tissues in vivo without damage or rejection. Proteins and other substances can have an effect directly, either within the reversibly electroporated cells or as products released from the cells after electroporation.

Certain embodiments of the invention relate to use of human scaffolds for use in preparation of engineered human tissues. As with other engineered tissues, such engineered tissues can be created in vitro, in vivo, or partially in vitro and partially in vivo. For example, tissue donors may have part or all of a tissue subjected to non-thermal IRE to produce a scaffold for tissue engineering for implantation of a recipient's cells, then growth of those cells. Upon infiltration and growth of the implanted cells, the tissue can be removed and implanted into the recipient in need of it. Of course, due to ethical concerns, the donor tissue should be tissue that is not critical for the life and health of the donor. For example, the tissue can be a portion of a liver. The engineered tissue, upon removal from the host and implanted in the recipient, can regenerate an entire functional liver, while the remaining portion of the host's liver can regenerate the portion removed.

Up to this point, the invention has been described in terms of engineered tissue scaffolds, engineered tissues, and methods of making them. It is important to note that the invention includes engineered organs and methods of making them as well. It is generally regarded that organs are defined portions of a multicellular animal that perform a discrete function or set of functions for the animal. It is further generally regarded that organs are made from tissues, and can be made from multiple types of tissues. Because the present invention is generally applicable to both tissues and organs, and the distinction between the two is not critical for understanding or practice of the invention, the terms "tissue" and "organ" are used herein interchangeably and with no intent to differentiate between the two.

Among the many concepts encompassed by the present invention, mention may be made of several exemplary concepts relating to engineered tissues. For example, in creating engineered organs, the initial organ can be completely removed of cells using irreversible electroporation prior to reseeding (this is especially relevant for organs having at least one dimension that is less than 1 mm); the organ can be irreversibly electroporated in sections and reseeded to allow the human cells to infiltrate small sections at a time; the organ can be irreversibly electroporated in incremental slices introducing the cells in stages, so that no human viable cells are in contact with the viable animal cells they are replacing; the organ can be irreversibly electroporated entirely or in sections and the human cells can be injected into targeted locations in the organ; the entire organ can be irreversibly electroporated to kill the animal cells, then human cells can be replanted on top of the organ to infiltrate the scaffold and replace the other cells (as the animal cells die, the human cells will fill in and substitute, thereby creating a new organ.)

Having provided isolated engineered tissues and organs, it is possible to provide methods of using them. The invention contemplates use of the engineered tissues in both in vitro and in vivo settings. Thus, the invention provides for use of the engineered tissues for research purposes and for therapeutic or medical/veterinary purposes. In research settings, an enormous number of practical applications exist for the technology. One example of such applications is use of the engineered tissues in an ex vivo cancer model, such as one to test the effectiveness of various ablation techniques (including, for example, radiation treatment, chemotherapy treatment, or a combination) in a lab, thus avoiding use of ill patients to optimize a treatment method. For example, one can attach a recently removed liver (e.g., pig liver) to a bioreactor or scaffold and treat the liver to ablate tissue. In addition, due to the absence of significant numbers of immune cells, tumors can be grown in the removed organs either by spontaneous means (carcinogens) or the introduction of tumorigenic cell lines into the tissue. These tumors may then be treated to improve understanding and promote optimization of a therapeutic technique in a more physiologically relevant, orthotopic setting. Another example of an in vivo use is for tissue engineering.

The engineered tissues of the present invention have use in vivo. Among the various uses, mention can be made of methods of in vivo treatment of subjects (used interchangeably herein with "patients", and meant to encompass both human and animals). In general, for certain embodiments, methods of treating subjects comprise implanting an engineered tissue according to the invention into or on the surface of a subject, where implanting of the tissue results in a detectable change in the subject. The detectable change can be any change that can be detected using the natural senses or using man-made devices. While any type of treatment is envisioned by the present invention (e.g., therapeutic treatment of a disease or disorder, cosmetic treatment of skin blemishes, etc.), in many embodiments, the treatment will be therapeutic treatment of a disease, disorder, or other affliction of a subject. As such, a detectable change may be detection of a change, preferably an improvement, in at least one clinical symptom of a disease or disorder affecting the subject. Exemplary in vivo therapeutic methods include regeneration of organs after treatment for a tumor, preparation of a surgical site for implantation of a medical device, skin grafting, and replacement of part or all of a tissue or organ, such as one damaged or destroyed by a disease or disorder (e.g., the liver). Exemplary organs or tissues include: heart, lung, liver, kidney, urinary bladder, spleen, pancreas, prostate, ovary, brain, ear, eye, or skin. In view of the fact that a subject may be a human or animal, the present invention has both medical and veterinary applications.

For example, the method of treating may be a method of regenerating a diseased or dysfunctional tissue in a subject. The method can comprise exposing a tissue to non-thermal IRE to kill cells of the treated tissue and create a tissue scaffold. The method can further comprise seeding the tissue scaffold with cells from outside of the subject, and allowing the seeded cells to proliferate in and on the tissue scaffold. Proliferation produces a regenerated tissue that contains healthy and functional cells. Such a method does not require removal of the tissue scaffold from the subject. Rather, the scaffold is created from the original tissue, then is re-seeded with healthy, functional cells. The entire process of scaffold creation, engineered tissue creation, and treatment of the subject is performed in vivo, with the possible exception of expansion of the cells to be seeded, which can be performed, if desired, in vitro.

In yet another exemplary embodiment, a tissue scaffold is created using non-thermal IRE to ablate a tissue in a donor animal. The treated tissue is allowed to remain in the donor's body to allow the body to clear cellular debris from the tissue scaffold. After an adequate amount of time, the treated tissue is removed from the donor's body and implanted into the recipient's body. The transplanted scaffold is not reseeded with external cells. Rather, the scaffold is naturally reseeded by the recipient's body to produce a functional tissue.

In yet another embodiment of the invention, the wire electrodes may be used to facilitate pulsed or continuous electric fields to induce reversible electroporation or thermal damage to a targeted region, either in vivo or ex vivo. Where it was shown in this example that irreversible electroporation was possible to a majority of the organ undergoing active perfusion, it has been proven that a tissue/organ's native vasculature serves as an adequate electrical conduit for delivery of the electric pulses to the tissue. Where reversible electroporation is a phenomenon that occurs at lower energy pulse parameters than irreversible electroporation, it is clear that reversible electroporation through the vasculature is also possible. This technique may be very useful when the practitioner desires not to ablate the targeted region, but introduce therapeutic macromolecules, such as genes or drugs, to the targeted region. The macromolecule used and desired therapeutic effect is left up to the practitioner. Furthermore, radiofrequency ablation is a commonly used thermal focal ablation technique which uses continuous alternating electric fields to heat tissue, whose utility in medicine may be enhanced and invasiveness reduced by incorporating the vascular electrode techniques described in this invention.

The present invention eliminates some of the major problems currently encountered with transplants. The methods described herein reduce the risk of rejection (as compared to traditional organ transplants) because the only cells remaining from the donor organ, if any, are cells involved in forming blood vessels and nerves. Yet at the same time, vascular, neural, and glandular structures are maintained. The present invention provides a relatively rapid, effective, and straightforward way to produce engineered tissues having substantially natural structure and function, and having reduced immunogenicity. As such, the engineered tissues of the present invention are highly suitable for therapeutic and cosmetic use, while having a relatively low probability of rejection. In embodiments where human organs are used as the source of the scaffold (e.g., from live organ donors or cadavers), the risk of rejection is very small.

In summary, the inventors have demonstrated a novel process, using newly-fabricated tools (electrodes and perfusion systems), that can be used for highly selective ablation of unwanted soft tissue, including cells, tissues and organs. Unique embodiments include application of pulsed electrical energy in fluids contained within tubing or vascular beds, control of perfusion fluid content and flow parameters, schemes of pulsed energy delivery, and use of other manipulations to confine and define therapeutic effects. It has further been demonstrated that cellular removal from intact tissues is possible and that this may be useful for creation of novel tissue matrices for a variety of uses. The results presented here are based on experiments conducted ex-vivo. However, the perfused fluid was similar in composition and conductivity to blood. This indicates that these experimental results are indicative of the responses which will be seen in-vivo.

The methods of energy delivery described in this specification, e.g., directly through the vasculature of the organ, can also be used to induce other therapeutic responses. Sub-lethal electric pulses (reversible electroporation) can be used to introduce genes or drugs into a specific organ or region of an organ to treat localized diseases. Similarly, radiofrequency ablation techniques could use the vasculature to deliver radiofrequency energy to destroy diseased tissue or tumors through acute hyperthermia. These modalities could be enhanced by delivering physiologically acceptable fluids (by way of co-perfusion) with different electrical properties to enhance these effects.

Because this energy is applied through the vasculature, large, yet controllable treatment volumes can be achieved. The overall structure of the organs is not disturbed because the energy is not being delivered by needle electrodes and organ puncture is not necessary. In addition, as predicted theoretically and validated experimentally, the delivered energy is being dissipated directly across the vascular or capillary bed rather than across bulk tissue. Typical treatments using needle or plate electrodes use similar voltages, deliver currents in excess of 1 Amp, and affect small volumes. In contrast, delivery of energy using vascular network of kidney results in currents on the order of 50 mA (200 times less power) while treating significantly larger volumes.

Example IV—Measuring Vascular Capability to Conduct Electric Current

Rationale: Accurate measurement of vasculature resistance to electrical current can play an important role in the development of accurate models and treatment protocols.

Exemplary Design: Sixteen porcine livers are harvested from mixed breed young pigs within two minutes of euthanasia induced via overdose of barbiturates. These tissues are immediately flushed with University of Wisconsin (UW) solution at 8° C. and placed on ice. Vascular anastomosis with a cardioemulation perfusion system (VasoWave™ 2.0, Smart Perfusion, Denver, N.C.) can be achieved by inserting Luer lock connectors into the portal vein (PV), hepatic artery (HA), and major hepatic vein (MHV) within 15 minutes of euthanasia. Access to the biliary system can be achieved by attaching a similar connection to the common bile duct (CBD). The livers can be perfused for one hour prior to experimentation to guarantee homogeneous distribution of the perfused fluid (perfusate) and complete removal of blood cells and other plasma constituents. The complex impedance (Z) of the vasculature can be measured by applying small sine-wave voltage signals with frequencies oscillating between 3 and 25 kHz. The voltage drop across the driving electrodes and current through a known resistor in the current path can be measured. The complex impedance between the following pairs can be calculated through Ohm's Law $$\left(Z = \frac{V}{I}\right);$$

1) PV—HA 2) PV—MHV 3) HA—MHV 4) PV—CBD 5) HA—CBD 6) MHV—CBD.

Overall Summary and Significance: The results from these experiments can provide the electrical characteristics of the vasculature system and the ability of each constituent to deliver charge. Impedance between the portal vein and hepatic artery is expected to be the least significant since these pathways merge at the lobule level. Impedance between the portal vein—major hepatic vein and hepatic artery major hepatic vein pairs is expected to be greater since the microvasculature which connects these structures at the lobule level should provide significant resistances individually. The impedance between each of the vasculature tracts and the common bile duct is expected to be the greatest since there should be no direct fluid path between these systems.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. As used in this specification, the singular forms "a," "an," and "the" include plural referents unless the context clearly dictates otherwise. Thus, for example, reference to "a pulse" includes a plurality of such pulses and reference to "the sample" includes reference to one or more samples and equivalents thereof known to those skilled in the art. It is intended that the specification and examples be considered as exemplary in nature and that variations that do not depart from the essence of the invention are intended to be within the scope of the invention. Further, the references cited in this disclosure are incorporated by reference herein in their entireties.

The invention claimed is:

1. A device for ablating target tissue cells comprising:
   a first connection device adapted for connection with a first blood vessel;
   a first electrode having an exposed portion disposed within the first connection device and adapted to be in contact with fluid inside the first blood vessel;
   a voltage source adapted to apply a plurality of electrical pulses to the first electrode so as to deliver ablation energy to target tissue cells using the fluid inside the first blood vessel an electrical conduit;
   a second connection device adapted for connection with a second blood vessel; and
   a second electrode adapted to be in contact with fluid inside the second blood vessel;
   wherein the first blood vessel is an artery and the second blood vessel is a vein; and
   whereby the plurality of electrical pulses are applied between the first and second electrodes.

2. The device of claim 1, wherein the voltage source is adapted to generate the plurality of electrical pulses in an amount sufficient to ablate the target tissue cells by irreversible electroporation (IRE).

3. The device of claim 1, wherein the voltage source is adapted to generate a plurality of radio frequency (RF) pulses through the first electrode in an amount sufficient to thermally ablate the target tissue cells.

4. The device of claim 1, wherein the first electrode is a wire electrode.

5. The device of claim 1, further comprising an external electrode adapted to be placed outside of the first blood vessel, wherein the plurality of electrical pulses are applied between the first electrode and the external electrode.

6. The device of claim 1, further comprising a second electrode adapted for insertion into a biliary tract, whereby the plurality of electrical pulses are applied between the first and second electrodes.

7. The device of claim 1, wherein the first electrode is adapted to be separated from a wall of the first blood vessel to avoid contact with the first blood vessel wall.

8. The device of claim 1, further comprising a perfusion system adapted for delivering a perfusate through the first connection device into the first blood vessel.

9. The device of claim 1, further comprising an occluding device configured to occlude the first blood vessel to isolate the target tissue cells from non-target tissue cells.

10. The device of claim 9, wherein the occluding device is adapted to occlude the first blood vessel upstream and downstream of the occluding device.

11. A device for ablating target tissue cells comprising:
    a first electrode adapted for insertion into a first blood vessel associated with target tissue cells and adapted to be in contact with fluid inside the first blood vessel;
    a voltage source adapted to apply a plurality of electrical pulses to the first electrode so as to deliver ablation energy to the target tissue cells using the fluid inside the first blood vessel an electrical conduit;
    further comprising a second electrode whereby the plurality of electrical pulses are applied between the first and second electrodes, wherein:
       the voltage source is adapted to generate the plurality of electrical pulses in an amount sufficient to ablate the target tissue cells by irreversible electroporation (IRE);
       the first and second electrodes are adapted for insertion respectively into an artery and a vein; and
    further comprising a first connection device adapted for connection with the first blood vessel, the first connection device having a one-way valve adapted to electrically isolate the target tissue cells between heart beats.

12. The device of claim 11, further comprising an occluding device to occlude the first blood vessel to isolate the target tissue cells from non-target tissue cells.

13. The device of claim 11, wherein the first electrode is a wire electrode.

14. A device for ablating target tissue cells comprising:
    a first connection device adapted for connection with a first blood vessel;
    a first electrode having an exposed portion disposed within the first connection device and adapted to be in contact with fluid inside the first blood vessel; and
    a voltage source adapted to apply a plurality of electrical pulses to the first electrode so as to deliver ablation energy to target tissue cells using the fluid inside the first blood vessel an electrical conduit;
    wherein the first connection device comprises a one-way valve adapted to electrically isolate the target tissue cells between heart beats.

* * * * *